United States Patent
Liu et al.

(10) Patent No.: US 10,167,339 B2
(45) Date of Patent: Jan. 1, 2019

(54) ANTAGONISTIC ANTI-OX40L ANTIBODIES AND METHODS OF THEIR USE

(71) Applicant: BAYLOR RESEARCH INSTITUTE, Dallas, TX (US)

(72) Inventors: Yong-Jun Liu, Gaithersburg, MD (US); Sandra Zurawski, Midlothian, TX (US); SangKon Oh, Baltimore, MD (US); Shino Hanabuchi, Gaithersburg, MD (US); Haruyuki Fujita, Gaithersburg, MD (US); Hideki Ueno, Plano, TX (US); Patrick Blanco, Verdelais (FR); Hyemee Joo, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 15/501,526

(22) PCT Filed: Aug. 3, 2015

(86) PCT No.: PCT/US2015/043408
§ 371 (c)(1),
(2) Date: Feb. 3, 2017

(87) PCT Pub. No.: WO2016/022468
PCT Pub. Date: Feb. 11, 2016

(65) Prior Publication Data
US 2017/0349661 A1    Dec. 7, 2017

Related U.S. Application Data

(60) Provisional application No. 62/032,959, filed on Aug. 4, 2014.

(51) Int. Cl.
*A61K 39/395* (2006.01)
*A61K 39/00* (2006.01)
*C07K 16/28* (2006.01)

(52) U.S. Cl.
CPC .... *C07K 16/2875* (2013.01); *A61K 2039/505* (2013.01); *A61K 2039/545* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 7,501,496 B1 * | 3/2009 | Endl | C07K 16/2875 424/133.1 |
| 7,812,133 B2 * | 10/2010 | Martin | C07K 16/2875 424/130.1 |
| 8,551,477 B1 | 8/2013 | Croft et al. | 424/130.1 |
| 8,962,807 B2 * | 2/2015 | Verdonck | C07K 16/2875 530/387.3 |
| 2012/0020960 A1 | 1/2012 | Palucka et al. | 424/133.1 |

FOREIGN PATENT DOCUMENTS

| EP | 0978287 | 2/2000 |
| WO | WO 2007/133290 | 11/2007 |
| WO | WO 2011/073180 | 6/2011 |

OTHER PUBLICATIONS

Webb et al. 2015. Clinic Rev Allerg Immunol. 50:312-332.*
Akiba et al., "The Role of ICOS in the CXCR5+ Follicular B Helper T Cell Maintenance In Vivo," *J. Immunol.* 2005; 175: 2340-2348.
Arestides et al., "Costimulatory molecule OX40L is critical for both Th1 and Th2 responses in allergic inflammation," *European Journal of Immunology* 2002; 32: 2874-2880.
Barrat & Coffman, "Development of TLR inhibitors for the treatment of autoimmune diseases," *Immunological Reviews*, 2008; 223(1):271-283.
Blanco et al., "Induction of Dendritic Cell Differentiation by IFN-α in Systemic Lupus Erythematosus," *Science*, 2001; 294(5546): 1540-1543.
Boettler et al., "Exogenous OX40 Stimulation during Lymphocytic Chroriomeningitis Virus Infection Impairs Follicular Th Cell Differentiation and Diverts CD4 T Cells into the Effector Lineage by Upregulating Blimp-1," *J. Immunol.* 2013; 191: 5026-5035.
Brocker et al., "CD4 T cell traffic control: in vivo evidence that ligation of OX40 on CD4 T cells by OX40-ligand expressed on dendritic cells leads to the accumulation of CD4 T cells in B follicles," *European Journal of Immunology*, 1999; 29: 1610-1616.
Byun et al., "Inherited Human OX40 Deficiency Underlying Classic Kaposi Sarcoma of Childhood," *The Journal of Experimental Medicine*, 2013; 210: 1743-1759.
Croft, Michael. "Control of Immunity by the TNFR-Related Molecule OX40 (CD134)," *Annual Review of Immunology*, 2010; 28: 57-78.
Crotty, "Follicular Helper CD4 T Cells ($T_{FH}$)," *Annual Review of Immunology*, 2011; 29:621-663.
Cunninghame Graham et al., "Polymorphism at the TNF superfamily gene TNFSF4 confers susceptibility to systemic lupus erythematosus," *Nat. Genet.*, 2008; 40(1): 83-89.
Delagado-Vega et al., *Genes Immun.* 2009; 10: 248-253.
Fillatreau & Gray, *The Journal of Experimental Medicine*, 2003; 197: 195-206.

(Continued)

*Primary Examiner* — Shulamith H Shafer
(74) *Attorney, Agent, or Firm* — Norton Rose Fulbright US LLP

(57) ABSTRACT

Described herein are methods and compositions for treating autoimmunity and inflammatory conditions without non-specific suppression of the host immune system. In particular, the anti-OX40L antibodies described herein are unique in that they not only inhibit the differentiation of inflammatory T cells but also promote the generation and function of regulatory T cells by inducing IL-10 and inhibiting TNF-α and by reducing aberrant Th2 cell responses. Furthermore, the methods and compositions described herein eliminate or reduce aberrant T follicular helper cell—(Tfh) responses that may contribute to the pathogenicity of autoimmune disease.

16 Claims, 25 Drawing Sheets
Specification includes a Sequence Listing.

(56) References Cited

OTHER PUBLICATIONS

Flynn et al., "CD4 T Cell Cytokine Differentiation: the B Cell Activation Molecule, OX40 Ligand, Instructs CD4 T Cells to Express Interleukin 4 and Upregulates Expression of the Chemokine Receptor, Blr-1," *The Journal of Experimental Medicine*, 1998; 188: 297-304.

Hong et al. "Islet allograft rejection in sensitized mice is refractory to control by combination therapy of immune-modulating agents," *Transplant Immunology*, 2013; 28: 86-92.

International Search Report and Written Opinion issued in Application No. PCT/US2015/043408, dated Nov. 20, 2015.

Karulf et al., "OX40 Ligand Regulates Inflammation and Mortality in the Innate Immune response to Sepsis," *J. Immunol.* 2010; 185: 4856-4862.

Klechevsky et al., "Functional Specializations of Human Epidermal Langerhans Cells and CD14+ Dermal Dendritic Cells" *Immunity*, 2008; 29: 497-510.

Kopf et al., "OX40-deficient mice are defective in Th cell proliferation but are competent in generating B cell and CTL Responses after virus infection," *Immunity*, 1999; 11: 699-708.

Marriott et al., "OX40 controls effector CD4+ T-cell expansion, not follicular T helper cell generation in acute Listeria infection," *Eur J. Immunol.* 2014; 44(8): 2437-47. DOI: 10.1002/eji.201344211.

Murata et al., "Constitutive OX40/OX40 Ligand Interaction Induces Autoimmune-Like Diseases," *J. Immunol.* 2002; 169: 4628-4636.

Nordmark et al., "Association of EBF1, FAM167A(C8orf13)-BLK and TNFSF4 gene variants with primary Sjögren's syndrome," *Genes Immun.* 2011; 12: 100-109.

Pratama et al., "Roquin-2 Shares Functions with its Paralog Roquin-1 in the Repression of mRNAs Controlling T Follicular Helper Cells and Systematic Inflammation," *Immunity*, 2013; 38: 669-680.

Sanchez et al., "Phenotypic associations of genetic susceptibility loci in systemic lupus erythematosus ," *Ann Rheum Dis.* 2011; 70: 1752-1757.

Shen et al., "Sex-specific association of X-linked Toll-like receptor 7 (TLR7) with male systemic lupus erythematosus," *Proceedings of the National Academy of Sciences*, 2010; 107: 15838-15843.

Stuber et al. "Involvement of OX40-OX40L Interactions in the Intestinal Manifestations of the Murine Acute Graft-Versus-Host Disease," *Gastroenterology* 1998; 115(5): 1205-1215.

Vogel, "Roquin Paralogs 1 and 2 Redundantly Repress the Icos and Ox40 Costimulator mRNAs and Control Follicular Helper T Cell Differentiation," *Immunity*, 2013; 38: 655-668.

Wu et al., "The Effect of OX40/OX40L and CD27/CD70 Pathways on Allogeneic Islet Graft Rejection," *Transplantation Proceedings*, 2001; 33: 217-218.

Zhang et al., "Upregulation of OX40 ligand on monocytes contributes to early virological control in patients with chronic hepatitis C," *European Journal of Immunology*, 2013; 43: 1953-1962.

Partial European Search Report Issued in Corresponding European Patent Application No. EP 15829426, dated Jan. 17, 2018.

Extended European Search Report Issued in Corresponding European Application No. 15829426.4, dated Apr. 25, 2018.

* cited by examiner

ANTAGONISTIC ANTI-OX40L ANTIBODIES AND METHODS OF THEIR USE

This application is a national phase under 35 U.S.C. § 371 of International Application No. PCT/US2015/043408, filed Aug. 3, 2015, which claims the benefit of priority to U.S. Provisional Patent Application Ser. No. 62/032,959, filed Aug. 4, 2014, the entire contents of each of which are hereby incorporated by reference in their entirety.

The invention was made with government support under Grant Nos. U19 AI057234, U19 AI082715, and U19 AI089987 awarded by the National Institutes of Health (NIH). The government has certain rights in the invention.

BACKGROUND OF THE INVENTION

1. Field of the Invention

The present invention relates generally to the field of medicine. More particularly, it concerns pharmaceutical compositions for treating autoimmune and inflammatory disorders and modifying immune responses.

2. Description of Related Art

Autoimmune diseases and some inflammatory disorders arise from an abnormal immune response of the body against substances and tissues normally present in the body (autoimmunity or auto-inflammatory). This may be restricted to certain organs (e.g. in autoimmune thyroiditis) or involve a particular tissue in different places (e.g. Goodpasture's disease which may affect the basement membrane in both the lung and the kidney). Autoimmune diseases affect up to 50 million people in America alone, and the cause of autoimmunity remains unknown. Furthermore, there are many inflammatory diseases that are not associated with autoimmunity and may be idiopathic or associated with a chronic or acute disorder.

The treatment of autoimmune and inflammatory diseases is typically with immunosuppression or anti-inflammatants—medication that decreases the immune and/or inflammation response. Conventional immunetherapies using immunosuppressants, such as cyclosporine, tacroliums, methotrexate or anti-TNFa/IL-6 non-specifically suppress the function of T cell including non-pathogenic T cells in the host. Therefore, treatment with these immunesuppressants often results in the development of severe infections and sometimes leads to the lethal consequences. There is a need in the art for therapeutics that treat autoimmune and/or inflammatory responses without global immunosuppression.

SUMMARY OF THE INVENTION

Described herein are methods and compositions for treating autoimmunity and inflammatory conditions without non-specific suppression of the host immune system. In particular, the anti-OX40L antibodies described herein are unique in that they not only inhibit the differentiation of inflammatory T cells but also promote the generation and function of regulatory T cells by inducing IL-10 and inhibiting TNF-α and by reducing aberrant Th2 cell responses. Furthermore, the methods and compositions described herein eliminate or reduce aberrant T follicular helper cell—(Tfh) responses that may contribute to the pathogenicity of autoimmune disease.

Disclosed is a pharmaceutical composition comprising an isolated anti-OX40L antibody or antigen-binding fragment thereof comprising a heavy chain variable domain comprising three complementarity determining region (CDR) amino acid sequences, wherein one or more of the CDRs comprise an amino acid sequence selected from SEQ ID NOs: 5-7, 19-21, 33-35, or an equivalent thereof. In some embodiments, an antibody of antigen binding fragment comprises three CDRs from a variable domain. In some embodiments, the three heavy chain variable domain CDRs comprise each of the amino acid sequences of SEQ ID NOs: 5-7 or an equivalent thereof. In other embodiments, the three heavy chain variable domain CDRs each comprise the amino acid sequence of SEQ ID NOs: 19-21 or an equivalent thereof. In other embodiments, the three heavy chain variable domain CDRs each comprise the amino acid sequence of SEQ ID NOs: 33-35 or an equivalent thereof. In further embodiments, the anti-OX40L antibody or antigen binding fragment thereof further comprises a light chain variable domain comprising three complementarity determining region (CDR) amino acid sequences, wherein one or more of the CDRs comprise an amino acid sequence selected from SEQ ID NOs: 12-14, 26-28, 40-42, or an equivalent thereof. In some embodiments, there are three light chain variable domain CDRs that each comprise the amino acid sequence of SEQ ID NOs: 12-14 or an equivalent thereof. In other embodiments, there are three light chain variable domain CDRs that each comprise the amino acid sequence of SEQ ID NOs: 26-28 or an equivalent thereof. In further embodiments, there are three light chain variable domain CDRs that each comprise the amino acid sequence of SEQ ID NOs: 40-42 or an equivalent thereof.

In certain embodiments described herein, the anti-OX40L antibody or antigen binding fragment thereof binds to human OX40L or an equivalent thereof. In a specific embodiment, the OX40L antibody is a neutralizing antibody that disrupts, prevents, or impedes a function or interaction (e.g. OX40-OX40L interaction) of the OX40L protein. In particular embodiments, the anti-OX40L antibody comprises the 5C6, 19A3, or 44F3 monoclonal antibody.

In other embodiments, the antibody is a human antibody, humanized antibody, recombinant antibody, chimeric antibody, an antibody derivative, a veneered antibody, a diabody, an engineered antibody, a multi-specific antibody, a DARPin (designed ankyrin repeat protein), a monoclonal antibody, or a polyclonal antibody. In some embodiments, the antibody is a humanized antibody.

In further embodiments, the OX40L antibody comprises a modification. In certain embodiments, the modification is a conservative amino acid mutation within the VH and/or VL CDR 1, CDR 2 and/or CDR 3 regions; of conservative amino acid mutations in the Fc hinge region; pegylation. conjugation to a serum protein; conjugation to human serum albumin; conjugation to a detectable label; conjugation to a diagnostic agent; conjugation to an enzyme; conjugation to a fluorescent, luminescent, or bioluminescent material; conjugation to a radioactive material; or conjugation to a therapeutic agent.

Certain embodiments relate to a pharmaceutical composition comprising an isolated humanized IgG anti-OX40L antibody or antigen-binding fragment thereof comprising a heavy chain variable domain comprising the complementarity determining region (CDR) amino acid sequences of SEQ ID NO: 5, SEQ ID NO: 6, and SEQ ID NO: 7 and a light chain variable domain comprising the complementarity determining region (CDR) amino acid sequences of SEQ ID NO: 12, SEQ ID NO: 13, and SEQ ID NO: 14.

Other embodiments relate to a pharmaceutical composition comprising an isolated humanized IgG anti-OX40L antibody or antigen-binding fragment thereof comprising a heavy chain variable domain comprising the complementarity determining region (CDR) amino acid sequences of SEQ ID NO: 19, SEQ ID NO: 20, and SEQ ID NO: 21 and a light chain variable domain comprising the complementarity determining region (CDR) amino acid sequences of SEQ ID NO: 26, SEQ ID NO: 27, and SEQ ID NO: 28.

Further embodiments relate to a pharmaceutical composition comprising an isolated humanized IgG anti-OX40L antibody or antigen-binding fragment thereof comprising a heavy chain variable domain comprising the complementarity determining region (CDR) amino acid sequences of SEQ ID NO: 33, SEQ ID NO: 34, and SEQ ID NO: 35 and a light chain variable domain comprising the complementarity determining region (CDR) amino acid sequences of SEQ ID NO: 40, SEQ ID NO: 41, and SEQ ID NO: 42.

Further aspects of the disclosure relate to an isolated polynucleotide comprising a nucleic acid sequence encoding a polypeptide chain of an anti-OX40L antibody or antigen-binding fragment thereof comprising a heavy chain variable domain comprising three complementarity determining region (CDR) amino acid sequences, wherein one or more of the CDRs comprise an amino acid sequence selected from SEQ ID NOs: 5-7, 19-21, 33-35, or an equivalent thereof. A further aspect relates to an isolated polynucleotide comprising a nucleic acid sequence encoding a polypeptide chain of an anti-OX40L antibody or antigen-binding fragment thereof comprising a light chain variable domain comprising three complementarity determining region (CDR) amino acid sequences, wherein one or more of the CDRs comprise an amino acid sequence selected from SEQ ID NOs: 12-14, 26-28, 40-42, or an equivalent thereof. Also disclosed is an expression vector comprising a polynucleotide described herein and a host cell comprising a polynucleotide described herein operably linked to a regulatory sequence.

Embodiments are provided in which the anti-OX40L antibody or antigen-binding fragment thereof comprises one or more CDR domains from an antibody that specifically binds to OX40L. In particular embodiments, the anti-OX40L antibody or antigen-binding fragment thereof comprises one, two, three, four, five, six, or more CDR domains from among the VH or VL domain of the 19A3, 5C6, and 44F3 monoclonal antibodies. In certain aspects, the anti-OX40L antibody or antigen-binding fragment thereof comprises six CDR domains from among the VH or VL domains of the 19A3, 5C6, and 44F3 monoclonal antibodies. In some embodiments, the anti-OX40L antibody or antigen-binding fragment thereof comprises a sequence at least or at most 70%, 75%, 80%, 85%, 90%, 95%, or 99% (or any range derivable therein) identical to the VH or VL domain of the 19A3, 5C6, and 44F3 monoclonal antibodies. Embodiments are provided in which the anti-OX40L antibody or antigen-binding fragment thereof comprises the VH domain from the 19A3, 5C6, or 44F3 monoclonal antibody and/or the VL domain the 19A3, 5C6, or 44F3 monoclonal antibody.

In certain embodiments, the antibody or antigen-binding fragment thereof is recombinant. In certain aspects, the recombinant polypeptide comprises at least 90%, 95%, or 99% of one or more CDR domains from the VH or VL domain of the 19A3, 5C6, and 44F3 monoclonal antibodies. In some embodiments, the recombinant polypeptide comprises two, three, four, five, six, or more CDR domains from the VH or VL domain of the 19A3, 5C6, and 44F3 monoclonal antibodies.

In some embodiments, a recombinant polypeptide comprises i) CDR1, CDR2, and/or CDR3 from the variable light chain of 19A3 (SEQ ID NOS:12-14); and/or ii) CDR1, CDR2, and/or CDR3 from the variable heavy chain of 19A3 (SEQ ID NOS:5-7). In some embodiments, a recombinant polypeptide comprises i) CDR1, CDR2, and/or CDR3 from the variable light chain of 5C6 (SEQ ID NOS:26-28); and/or ii) CDR1, CDR2, and/or CDR3 from the variable heavy chain of 5C6 (SEQ ID NOS:19-21). In some embodiments, a recombinant polypeptide comprises i) CDR1, CDR2, and/or CDR3 from the variable light chain of 44F3 (SEQ ID NOS:40-42); and/or ii) CDR1, CDR2, and/or CDR3 from the variable heavy chain of 44F3 (SEQ ID NOS:33-35). The sequences for these CDRs can be found in the disclosure that follows.

In some embodiments, there is a purified polypeptide comprising one or more anti-OX40L antibody CDR domains. As indicated above, the polypeptide may comprise 1, 2, 3, 4, 5, or 6 CDRs from the light and/or heavy chain variable regions of an anti-OX40L antibody. In certain embodiments, a polypeptide contains CDR1, CDR2, and/or CDR3 from the light chain variable region of a particular antibody. It is contemplated that while in some embodiments a polypeptide has a CDR1, CDR2, and CDR3 from the variable region of a light chain and/or the variable region of a heavy chain that the CDR1, CDR2, and CDR3 need not be from the same antibody. While some polypeptides have CDR1, CDR2, and CDR3 from the same antibody or based on the same antibody, it is contemplated that a CDR1 from one antibody may be substituted with a CDR from or based on another antibody. For example, a polypeptide may comprise a CDR1 from or based on the light chain variable region of 19A3, a CDR2 from or based on the light chain variable region of 19A3, but have a CDR3 from or based on the variable light chain region of 5C6. It is generally contemplated, however, that when a single set of CDR1, CDR2, and CDR3 are employed together that they all be from a light chain variable region or from a heavy chain variable region, but not a mix from both.

Alternatively, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:12, 26, and 40, which are CDR1 sequences from the light chain variable region of an anti-OX40L antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:13, 27, and 41, which are CDR2 sequences from the light chain variable region of an anti-OX40L antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:14, 28, and 42, which are CDR3 sequence from the light chain variable region of an anti-OX40L antibody. Alternatively or additionally, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs: 5, 19, and 33, which are CDR1 sequences from the heavy chain variable region of an anti-OX40L antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:6, 20, and 34, which are CDR2 sequences from the heavy chain variable region of an anti-OX40L antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:7, 21, and 35, which are CDR3 sequences from the heavy chain variable region of an anti-OX40L antibody.

Method aspects of the disclosure relate to a method for treating or preventing inflammation in a subject in need thereof comprising administering to the subject a therapeutically effective amount of an OX40L inhibitor.

Further aspects relate to a method for treating or preventing an autoimmune disease in a subject in need thereof comprising administering to the subject a therapeutically effective amount of an OX40L inhibitor.

In certain aspects, the method is for preventing inflammation associated with an autoimmune disease in a subject in need thereof comprising administering to the subject a therapeutically effective amount of an OX40L inhibitor.

Other aspects relate to a method for reducing inflammatory Th2 cell responses, for increasing IL-10 production and/or for reducing TNF-a production in a subject in need thereof comprising administering to the subject a therapeutically effective amount of an OX40L inhibitor. In some embodiments, the inflammatory Th2 cell responses comprise IL-10 low/TNF-α height producing inflammatory Th2 cells.

Other aspects relate to a method for decreasing pathogenic Tfh cell responses in a subject in need thereof comprising administering a therapeutically effective amount of an OX40L inhibitor.

In some embodiments, the subject being treated is one that has an autoimmune disease. In certain aspects, the autoimmune disorder in the subject is treated by the administration of an OX40L inhibitor, which decreases pathogenic Tfh cell responses in the subject.

In further embodiments, the subject has inflammation. The inflammation in the subject may be reduced or eliminated by administering an OX40L inhibitor, which increases IL-10 production and reduces TNF-a production in the subject. The OX40L inhibitor may also reduce inflammation by reducing inflammatory Th2 cell responses in the subject.

In some embodiments, the subject being treated has an autoimmune disorder or has inflammation as a result of an autoimmune disorder. In some embodiments, the autoimmune disease selected from the group allergic disease asthma, atopic dermatitis, experimental autoimmune encephalomyelitis, inflammatory bowel disease, contact hypersensitivity, asthmatic airway hyperreaction, autoimmune diabetes, atherosclerosis, systemic lupus erythematosus, Sjogren's syndrome, type 1 diabetes, rheumatoid arthritis, multiple sclerosis, ulcerative colitis, polymyositis, mixed connective tissue disease, systemic sclerosis, myasthenia gravis, thyroiditis, autoimmune hemolytic anemia, immune thrombocytopenic purpura, dermatomyositis, antineutrophil cytoplasmic autoantibody-mediated disease, IgA-mediated vasculitis, and Ig4-related disorders. In some embodiments, the autoimmune disease is systemic lupus erythematosus.

In further embodiments, the inflammation may be idiopathic. In yet further embodiments, the inflammation may be the result of a disease or condition that is not autoimmune related, such as an injury.

Further aspects relate to a method for treating or preventing graft versus host disease or graft rejection in a subject in need thereof comprising administering to the subject a therapeutically effective amount of an OX40L inhibitor.

Graft-versus-host disease (GVHD) is a common complication following an allogeneic tissue transplant. It is commonly associated with stem cell or bone marrow transplant but the term also applies to other forms of tissue graft. Immune cells (white blood cells) in the tissue (the graft) recognize the recipient (the host) as "foreign". The transplanted immune cells then attack the host's body cells. GVHD may also occur after a blood transfusion if the blood products used have not been irradiated.

Graft rejection occurs when transplanted tissue is rejected by the recipient's immune system, which destroys the transplanted tissue. Graft rejection may also be referred to as transplant rejection or host versus graft disease.

In some embodiments of any of the above-disclosed methods, the subject is one that will receive or has received transplanted tissues. In a related embodiment, the transplanted tissue is an allograft. An allograft (also known as allotransplantation, allogeneic transplant, or homograft) is the transplantation of cells, tissues, or organs, to a recipient from a genetically non-identical donor of the same species. In a related embodiment, the subject is one that has a complication from the transplanted tissue, wherein the complication is graft rejection or GVHD.

The term "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets. In one embodiment of the methods described herein, the subject is a human subject.

The OX40L inhibitor may be an siRNA, dsRNA, miRNA, ribozyme, molecular inhibitor, small molecule, antibody, or antigen binding fragment. In some embodiments, the OX40L inhibitor is an OX40L antibody or antigen-binding fragment thereof. In further embodiments, the OX40L inhibitor comprises a composition as described herein. In yet further embodiments, the OX40L inhibitor comprises a polypeptide, polynucleotide, antibody, host cell, or expression vector described herein.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

p<0.01. (D) Correlation between the frequency of OX40L+ cells within the CD14+ APCs and the frequency of CXCR5+ IL-21+ Th cells generated in the cultures. Spearman correlation test, n=10. (E) Expression of ICOS on blood Tfh cells in the three groups; aSLE, iSLE, and HD. A representative flow result is shown. (F) Correlation between the frequency of OX40L+ cells within blood myeloid APCs and the frequency of ICOS+ cells within blood Tfh cells in SLE patients. Spearman correlation test, n=19.

FIG. 14A-14E shows that RNP/anti-RNP ICs promote OX40L expression by myeloid APCs in a TLR7-dependent manner. (A) Expression of OX40L (MFI) by purified normal monocytes exposed to control sera (n=7) or SLE sera (n=21). Mann-Whitney U-test.  p<0.01. A representative staining is shown on the left panel. (B) OX40L expression upon stimulation of purified normal monocytes by TLR3, TLR7 or TLR9 agonists. A representative staining out of 4 different experiments is shown. (C) OX40L expression (MFI) in normal monocytes exposed to SLE sera (n=7) in the presence or not of a TLR7 inhibitor. Paired t-test.  p<0.01. A representative staining is shown on the left panel. (D) OX40L expression (MFI) in normal monocytes exposed to anti-RNP$^{neg}$ SLE sera (n=5) or anti-RNP$^{pos}$ SLE sera (n=16). Mann-Whitney U-test. ** p<0.01. (E) OX40L expression of purified normal monocytes exposed to anti-RNP$^{neg}$ SLE serum (upper panel), the serum supplemented with anti-RNP-containing IgG (medium panel), the serum spiked with anti-RNP-containing IgG in the presence of a TLR7 inhibitor (lower panel). A representative staining out of three independent experiments is shown.

Figure 15:
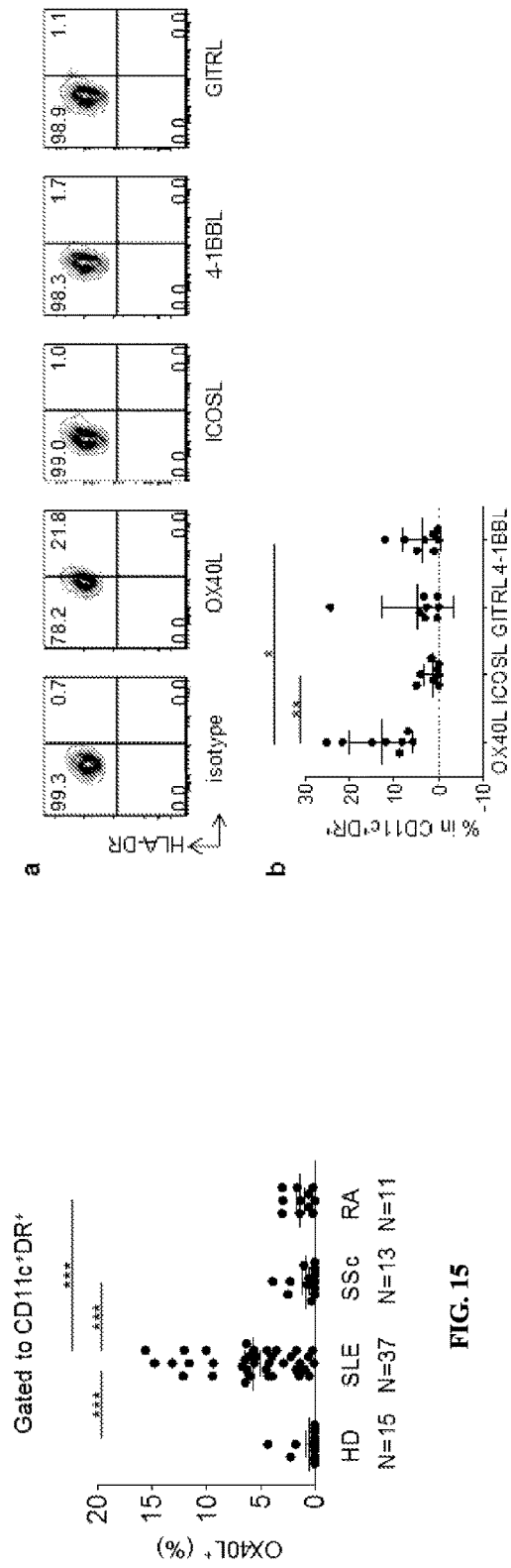

FIG. 15 shows that OX40L expression by myeloid APCs in SLE. Analysis of OX40L expression by blood CD11c+ HLA-DR+ cells in 15 healthy donor (HD), 37 SLE, 13 systemic sclerosis (SSc) and 11 rheumatoid arthritis (RA) patients. One-way ANOVA. *** P<0.001.

FIG. 16A-16B demonstrates that blood myeloid APCs in active SLE patients do not express ICOSL, 4-1BBL, or GITRL. Analysis of OX40L, GITRL, ICOSL, 4-1BBL expression by blood myeloid APCs in 8 active SLE patients. A representative flow result is shown in panel a. b. One-way ANOVA. ** P<0.01, * P<0.05.

Figure 17:
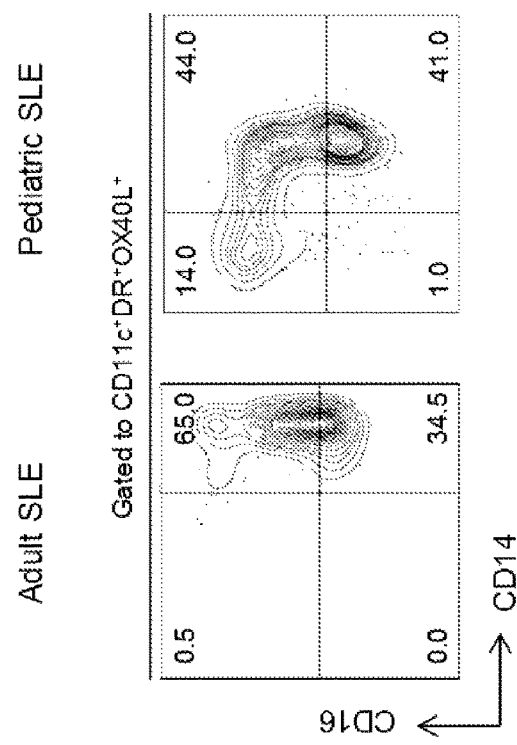

FIG. 17 demonstrates that a majority of blood OX40L+ myeloid APCs express CD14. CD14 and CD16 expression was analyzed on blood OX40L+ myeloid APCs in adult and pediatric SLE patients. A representative flow result from 11 adult SLE and 12 pediatric SLE patient samples is shown.

Figure 18:
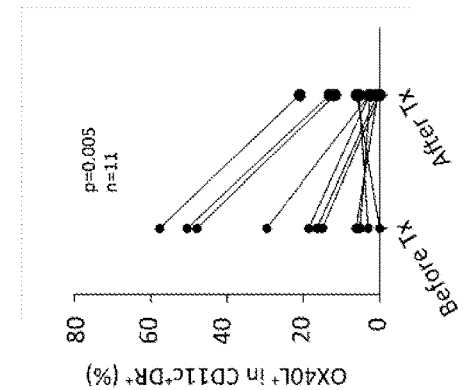

FIG. 18 shows that OX40L expression on blood myeloid APCs decreases after treatment in adult SLE patients. The expression of OX40L on blood myeloid APCs was analyzed in 11 flaring previously untreated adult SLE patients before and after treatment (Tx). The percentage of OX40L+ cells within blood myeloid APCs before and after treatment is shown. Paired t-test, n=11.

Figure 19:
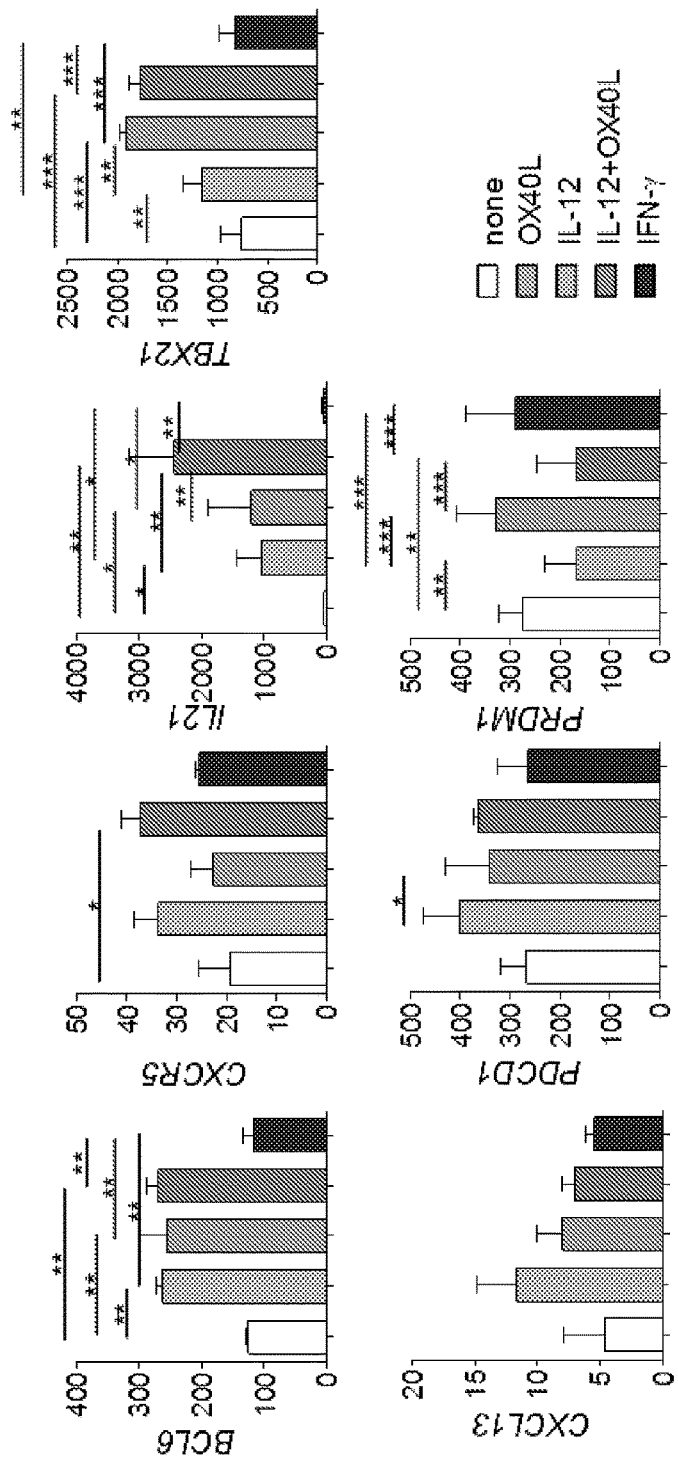

FIG. 19 demonstrates that OX40 signals induce naïve Th cells to express Tfh genes. Tfh gene expression profiles by naïve Th cells activated with anti-CD3 and anti-CD28 in the presence of indicated reagents for 48 h. The bars in each bar graph represent, from left to right, "none," "OX40L," "IL-2," "IL-2+OX40L," and "IFN-γ." Mean±s.d., n=3. One-way ANOVA. * P<0.05,  P<0.01, * P<0.001.

Figure 20:
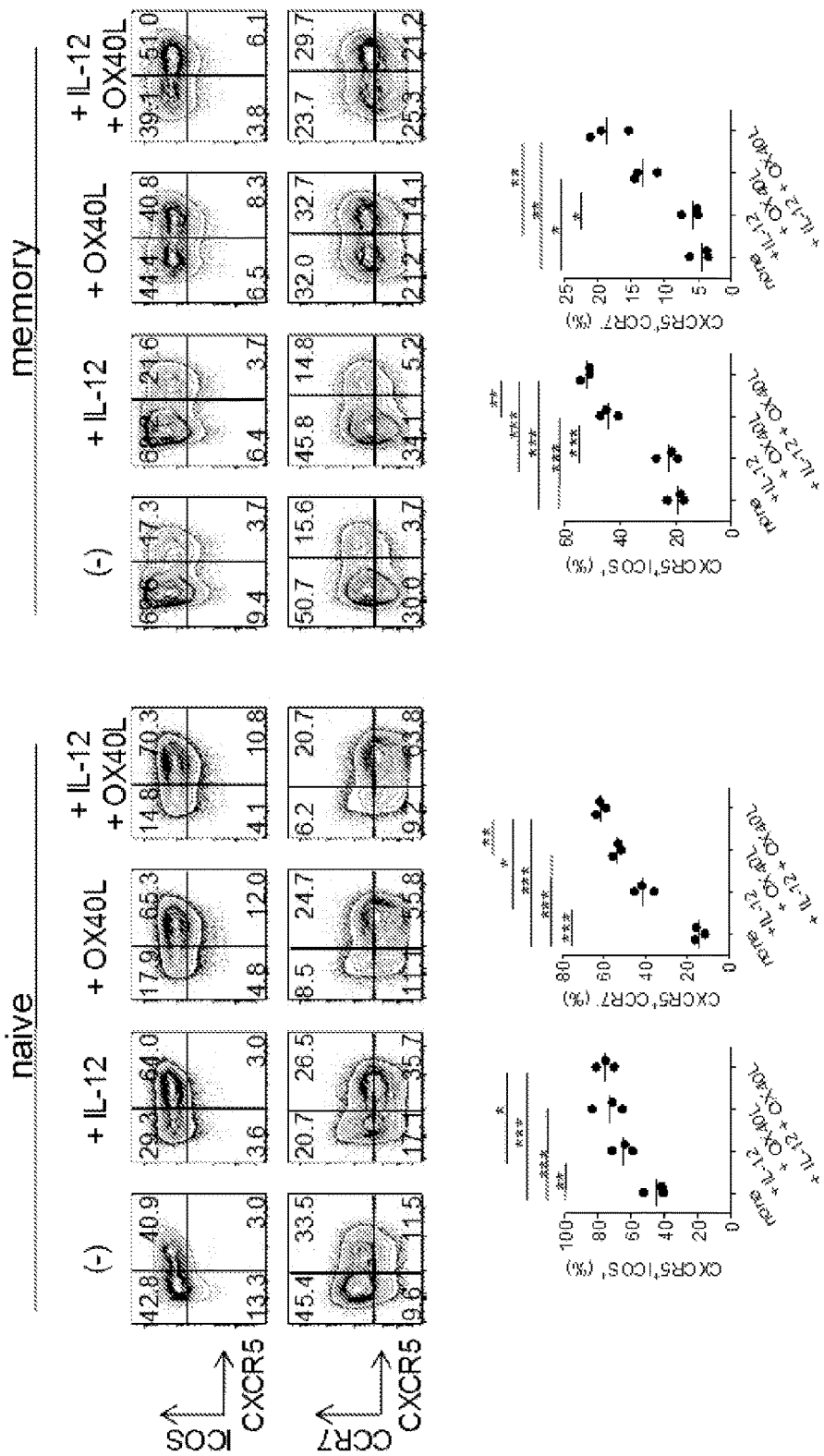

FIG. 20 shows that OX40L stimulation promotes naïve and memory Th cells to acquire the phenotype of Tfh cells. Naïve and memory Th cells were cultured with anti-CD3 and CD28 in the presence or absence of IL-12 and/or soluble OX40L. The phenotype of activated (FSChiSSChi) cells was analysed by flow cytometry at day 5. A representative flow result is shown in the top panel. The percentage of CXCR5+ICOS+ and CXCR5+CCR7− cells within activated cells in the different conditions is shown in the bottom panel. One-way ANOVA. * P<0.001,  P<0.01, * P<0.05.

Figure 21:
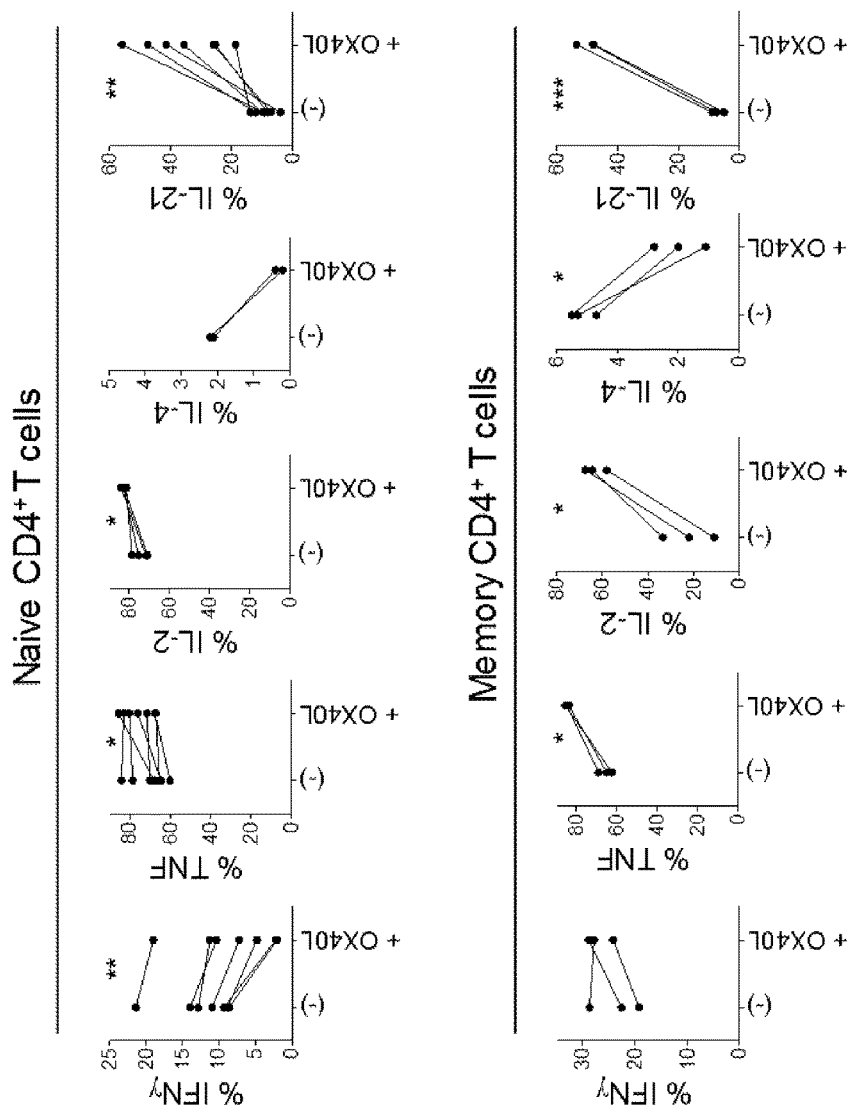

FIG. 21 shows that OX40L stimulation induces naïve and memory Th cells to express IL-21, IL-2 and TNF-α. CXCR5, IL-21 and CD40L expression of naïve and memory Th cells activated with anti-CD3 and anti-CD28 in the presence or absence of sOX40L. Cultured Th cells were re-stimulated for 6 h with PMA and ionomycin in the presence of brefeldin A and monensin to analyze the intracytplasmic cytokines. Paired t-test. * P<0.001,  P<0.01, * P<0.05.

Figure 22:
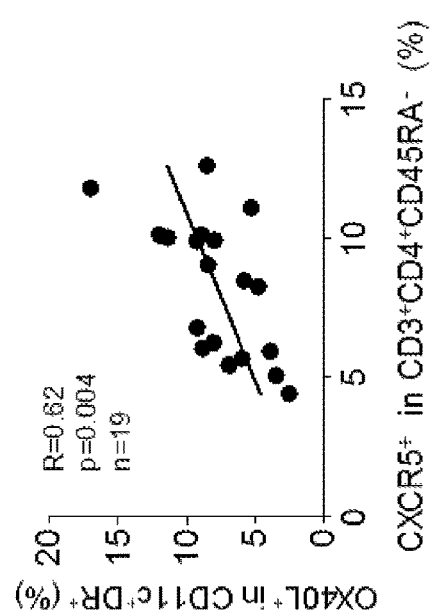

FIG. 22 shows that the percentage of OX40L+ cells within blood myeloid APCs correlate with the frequency of blood Tfh cells in SLE patients. The correlation between the frequency of OX40L+ cells within blood myeloid APCs and the frequency of blood Tfh cells was analyzed in 19 SLE patients. Statistical analysis was performed with the Spearman test.

Figure 23:
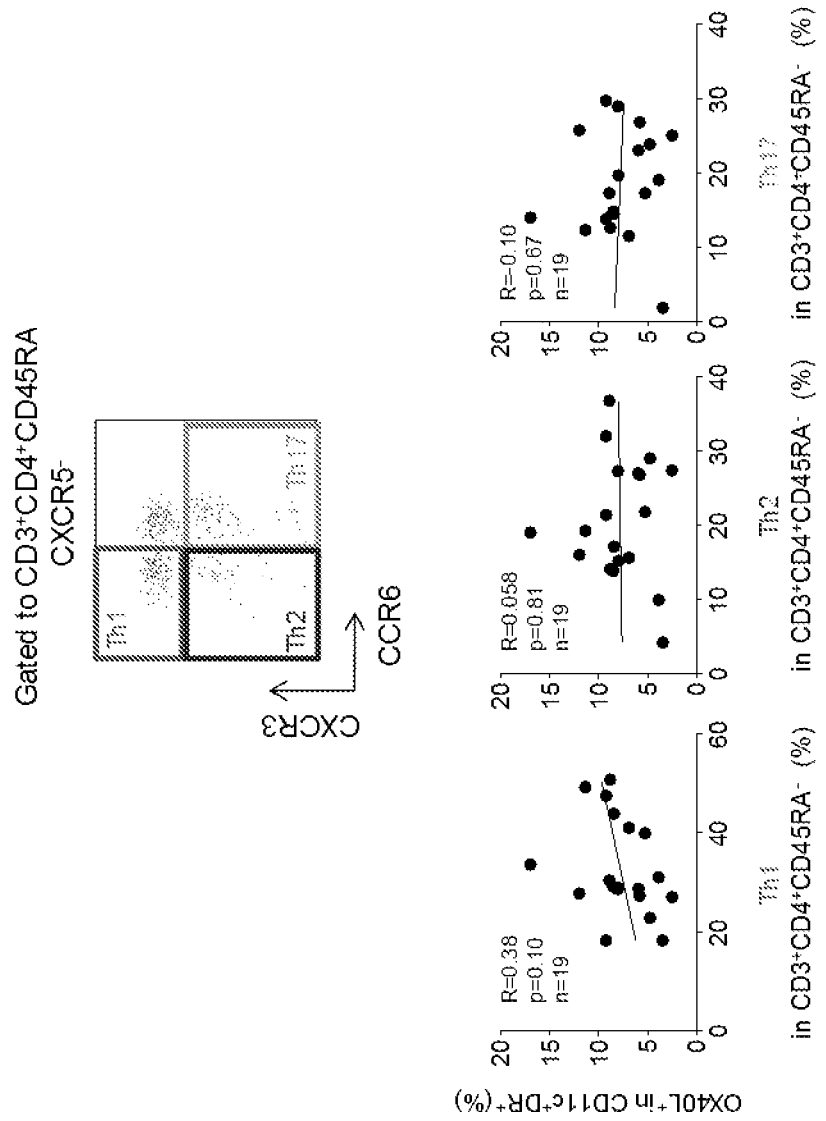

FIG. 23 shows that the percentage of OX40L+ cells within blood myeloid APCs does not correlate with the frequency of blood Th1, Th2, and Th17 cells in SLE patients. Gating strategy for the analysis of blood Th1, Th2, and Th17 cells (within memory CXCR5− Th cells) is shown in the top panel. The correlation between the frequency of OX40L+ cells within blood myeloid APCs and the frequency of blood Th1, Th2, and Th17 cells was analyzed in 19 SLE patients. Statistical analysis was performed with the Spearman test.

Figure 24:
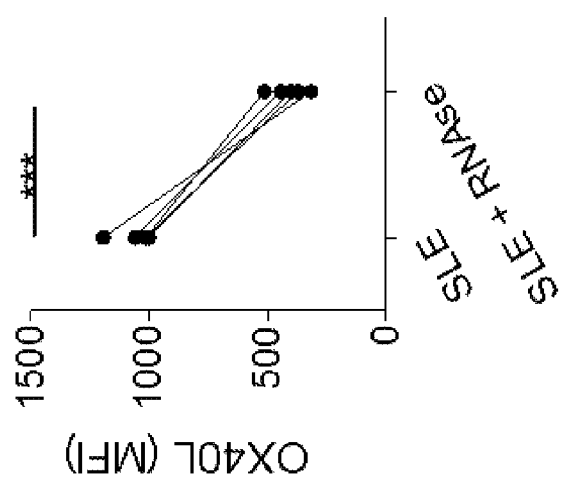

FIG. 24 shows that OX40L expression by SLE sera is dependent on RNA. OX40L expression by purified normal monocytes exposed to SLE sera in the presence or not of RNAse (0.1 mg/ml. Qiagen). Results with serum samples from 5 SLE patients. Paired t-test, *** P<0.001.

Figure 25:
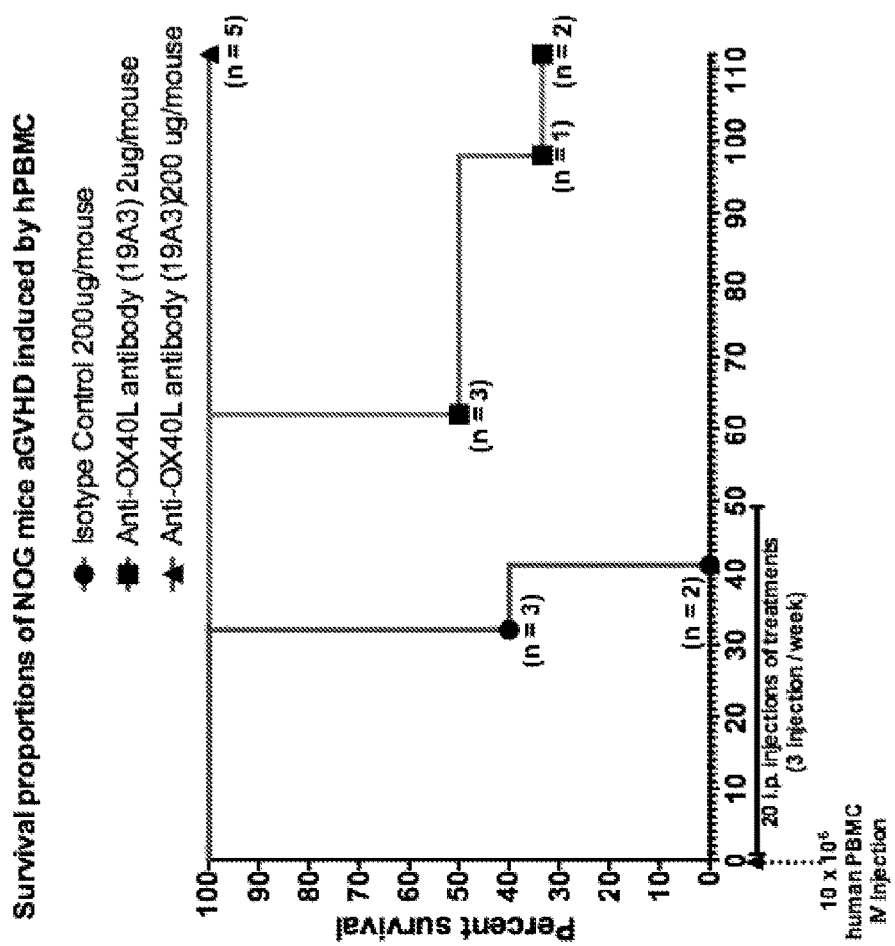

FIG. 25 shows the percent survival of animals after transplantation of graft tissue.

Figure 26A:
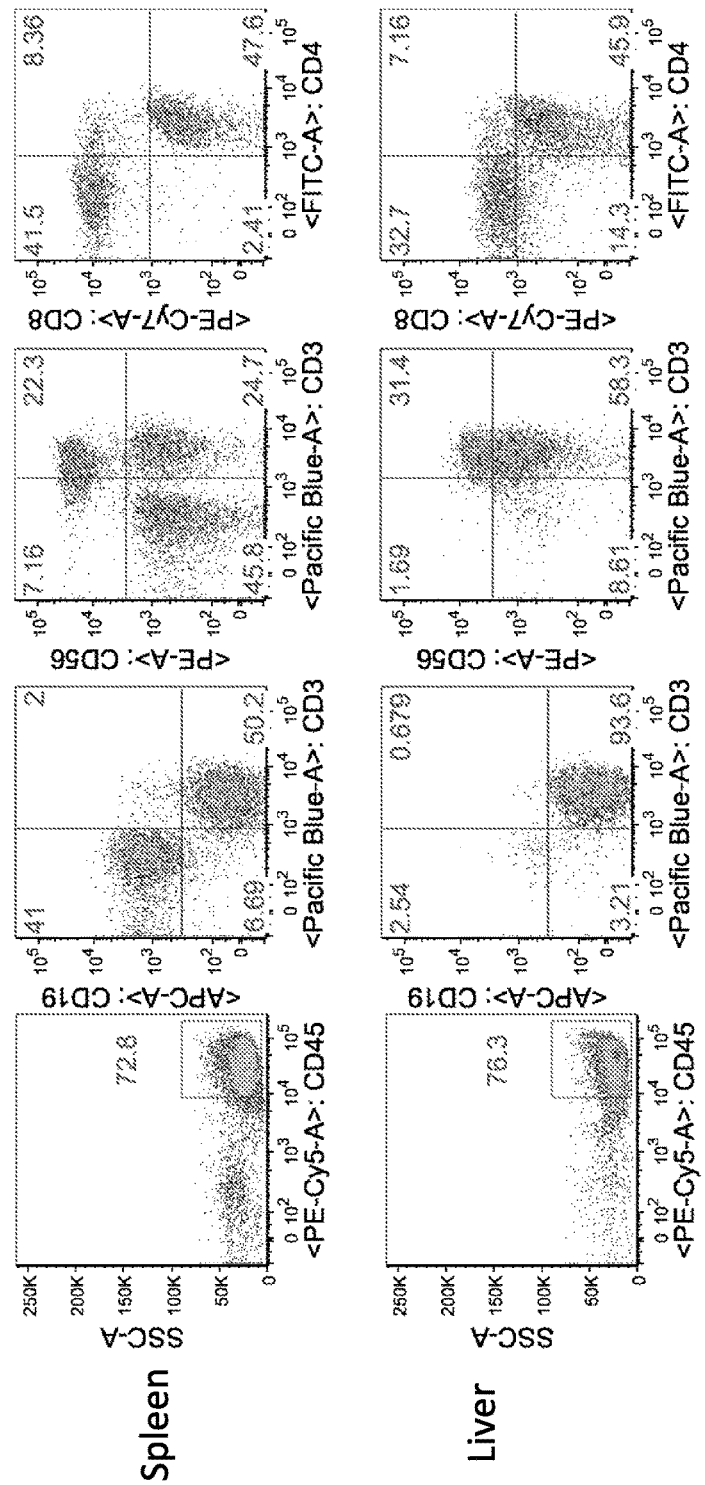
Figure 26B:
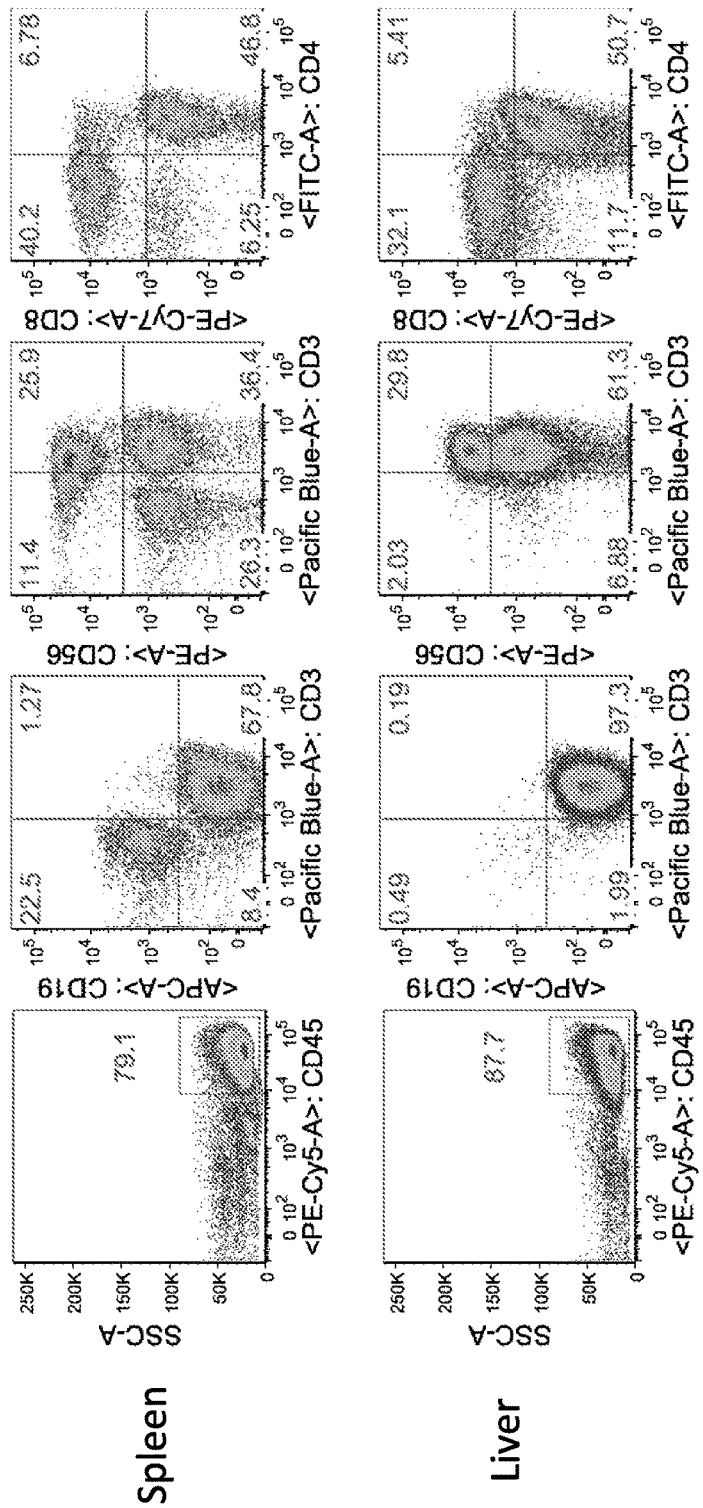

FIG. 26A-B shows that anti-OX40L antibody does not interfere with human chimerism. Shown are FACS plots with IgG2b treated (FIG. 26A) and anti-OX40L (FIG. 26B) treated mice.

DESCRIPTION OF ILLUSTRATIVE EMBODIMENTS

Conventional immunetherapies using immunosuppressants, such as cyclosporine, tacroliums, methotrexate or anti-TNFa/IL-6 non-specifically suppress T cell functions, including non-pathogenic T cells in the host. Therefore, treatment with these immunosuppressants often results in the development of severe infections and sometimes leads to the lethal consequences. Methods and compositions described herein are directed to the deliberate blockade of the OX40-OX40L interaction and the specific suppression of the recent activation of inflammatory T cells. In turn, the differentiation of inflammatory T cells is converted into regulatory T cells by the induction of IL-10 and inhibition of TNF-a production without global immune suppression. Importantly, the targeting of OX40L can modulate only antigen-specific T cell repertoire without disrupting the function of the other T cell repertoires, resulting in less immunosuppressive side effects.

Using unique screening methods, Applicants have made anti-human OX40L neutralizing MAbs, which 1) recognize unique epitopes on human OX40L; 2) inhibit the differentiation of IL-10 low/TNFa high producing inflammatory Th2 primed by TSLP-mDCs; and 3) inhibit the proliferation and the production of TNF-a, and promote IL-10 by CD4 T cells cultured with OX40L-transfected cell line. These OX40L blocking monoclonal antibodies are powerful immune modulators and provide promising therapeutics for the inflammatory diseases such as graft versus host disease, system lupus erythematosus, cardiovascular disease (e.g. atherosclerosis), and inflammatory diseases such as those described herein.

I. OX40L Inhibitors

A. Antibodies

Methods and compositions of the disclosure relate to OX40L inhibitors. The term "OX40L" refers to a protein that has been found to be involved in T cell antigen-presenting cell (APC) interactions. OX40L may also be known as TNFSF4, GP34, CD252, OX40L, TXGP1, and CD134L. This protein is a ligand for OX40 (also known as CD134, TNFRSF4, ACT35, IMD16, and TXGP1L). The human protein sequence of OX40L is represented by Genbank Accession Nos: NP_003317.1, P23510.1, BAB18304.1, and P43489.1. The sequences associated with these accession numbers are specifically incorporated by reference.

In certain embodiments, the OX40L inhibitor is an antibody or antigen-binding fragment thereof. As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region or any portion thereof or at least one portion of a binding protein. In certain embodiments, the antibody or antigen binding fragment specifically binds human OX40L.

The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant antibody, a recombinant humanized antibody, an engineered antibody, a multi-specific antibody, a DARPin, or a derivative or fragment of each thereof.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Common variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Unless specified otherwise, the antibodies can be polyclonal or monoclonal and can be isolated from any suitable biological source, e.g., murine, rat, rabbit, goat, camelid, sheep or canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. In some instances, the antibodies are indirectly labeled. Indirect labelling may involve the labeling of a protein that binds to the antibody, such as a secondary antibody.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice) (Nguyen et al., 1977; Sandhu et al., 1996); Eren et al., 1998), that are capable of producing a repertoire of human antibodies, as known in the art and/or as described herein. Such techniques, include, but are not limited to, ribosome display (Wanes et al., 1997; Hanes et al., 1998); single cell antibody producing technologies (e.g., selected lymphocyte antibody method ("SLAM") (U.S. Pat. No. 5,627,052, Wen et al., 1987; Babcook et al., 1996); gel microdroplet and flow cytometry (Powell et al., 1990; Gray et al., 1995; Kenny et al., 1995); B-cell selection (Steenbakkers et al., 1994).

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The term "mouse antibody" as used herein, is intended to include antibodies having variable and constant regions derived from mouse germline immunoglobulin sequences.

As used herein, chimeric antibodies are antibodies whose light and heavy chain genes have been constructed, typically by genetic engineering, from antibody variable and constant region genes belonging to different species.

In one embodiment, the anti-OX40L antibody or antigen binding fragment thereof is a neutralizing antibody or antigen-binding fragment thereof. The term "neutralizing" in the context of an OX40L neutralizing antibody refers to an antibody that may do one or more of: interfere with the OX40/OX40L interaction; reduce the concentration of OX40/OX40L interacted species in a subject or a cell; prevent the OX40/OX40L interaction in a subject or a cell; and/or reduce the biological function of OX40L, which may include one or more of: inhibiting the proliferation and the production of TNF-a, promoting IL-10 production by $CD4^+$ T cells, suppressing the activation of inflammatory T cells, and/or converting the differentiation of inflammatory T cells into regulatory T cells.

In further embodiments, the antibody comprises a modification and is an "antibody derivative." The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies of the invention also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. Antibody derivatives have also been produced in large amounts from transgenic plant seeds including antibody fragments, such as single chain antibodies (scFv's), including tobacco seeds and potato tubers. See, e.g., Conrad et al., 1998 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

The term "variable region" refers to a portion of the antibody that gives the antibody its specificity for binding antigen. The variable region is typically located at the ends of the heavy and light chains. Variable loops of β-strands, three each on the light (VL) and heavy (VH) chains are responsible for binding to the antigen. These loops are referred to as the "complementarity determining regions" (CDRs).

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The term "constant region" refers to a portion of the antibody that is identical in all antibodies of the same isotype. The constant region differs in antibodies of different isotypes.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

Chimeric, humanized or primatized antibodies of the present invention can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. No. 5,225,539 and U.S. Pat. Nos. 5,530,101; 5,585,089; 5,693,762 and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al., 2000; Gallo et al., 2000; Green, 1999; Yang et al., 1999A; Yang, 1999B; Jakobovits, 1998; Green and Jakobovits, 1998; Jakobovits, 1998; Tsuda et al., 1997; Sherman-Gold, 1997; Mendez et al., 1997; Jakobovits, 1996; Jakobovits, 1995; Mendez et al, 1995; Jakobovits, 1994; Arbones et al., 1994; Jakobovits, 1993; Jakobovits et al., 1993; U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al., 1991.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger, et al., 1993) By using a linker that is too short to allow pairing between the two domains on the same chain, the domains are forced to pair with the complementary domains of another chain and create two antigen-binding sites. (See also, U.S. Pat. No. 6,632,926 to Chen et al, which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies (Holliger & Hudson, 2005; U.S. Patent Publication US 2006/0211088; PCT Publication WO2007/059782; U.S. Pat. No. 5,831,012).

The term "antibody derivative" further includes "linear antibodies". The procedure for making linear antibodies is known in the art and described in Zapata et al., 1995. Briefly, these antibodies comprise a pair of tandem Ed segments (V.sub.H-C.sub.H1-VH-C.sub.H1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

In certain embodiments, the antibodies of the invention are recombinant antibodies. A recombinant antibody differs from an endogenously-produced antibody. For example, recombinant antibodies differ with respect to their glycosylation status (see, for example, Jefferis, R. "Glycolsylation of Recombinant Antibody Therapeutics" *Biotechnol. Prog.* 2005, 21:11-16 which is herein incorporated by reference).

In some embodiments, the antibody is an engineered antibody. For example, the Fc region may be engineered to increase binding to Fcγ receptors of effector cells. This may involve modifying antibody glycosylation patterns or mutating amino acids in the Fc region. Glycoengineering may be performed by methods known in the art such as POTELLIGENT and Glycart. Methods for amino acid engineering are also known and used in the art (e.g. Xmab approach by Xencor). Amino acid changes to the Fc region can improve antibody-dependent cell-mediated cytotoxicity and complement dependent cytotoxicity by way of improved binding to effector cells, but may also allow for an extended half-life. See Evans and Syed, *Nature Reviews,* 2014, 13:413-414, for further examples.

Antibodies of the disclosure may be mono-, bi-, or multi-specific. Bi and multi-specific antibodies are antibodies that recognize two or multiple antigenic targets. There are some multi-specific antibody platforms commercially in use, which include the "BiTE" (bispecific T cell engager) platform, and the DART platform.

Multispecific antibodies, engineered antibodies and various other platforms are described in Evans and Syed, "Next-generation antibodies," *Nature Reviews*, 2014, 13:413-414, which is hereby incorporated by reference in its entirety.

If an antibody being tested binds with protein or polypeptide, then the antibody being tested and the antibodies provided by this invention are equivalent. In one embodiment, an equivalent is one that binds OX40L and provides the same neutralizing activity and/or cell response (i.e. inhibit the differentiation of IL-10 low/TNF-a high producing inflammatory Th2 primed by TSLP-mDCs and/or inhibit the proliferation and the production of TNF-1 and promote IL-10 by CD4+ T cells).

It also is possible to determine without undue experimentation, whether an antibody has the same specificity as the antibody of this invention by determining whether the antibody being tested prevents an antibody of this invention from binding the protein or polypeptide with which the antibody is normally reactive. If the antibody being tested competes with the antibody of the invention as shown by a decrease in binding by the monoclonal antibody of this invention, then it is likely that the two antibodies bind to the same or a closely related epitope. Alternatively, one can pre-incubate the antibody of this invention with a protein with which it is normally reactive, and determine if the antibody being tested is inhibited in its ability to bind the antigen. If the antibody being tested is inhibited then, in all likelihood, it has the same, or a closely related, epitopic specificity as the antibody of this invention.

The term "antibody" also is intended to include antibodies of all immunoglobulin isotypes and subclasses unless specified otherwise. An isotype refers to the genetic variations or differences in the constant regions of the heavy and light chains of an antibody. In humans, there are five heavy chain isotypes: IgA, IgD, IgG, IgE, and IgM and two light chain isotypes: kappa and lambda. The IgG class is divided into four isotypes: IgG1, IgG2, IgG3 and IgG4 in humans, and IgG1, IgG2a, IgG2b and IgG3 in mice. They share more than 95% homology in the amino acid sequences of the Fc regions but show major differences in the amino acid composition and structure of the hinge region. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al., 1985; Spira et al, 1984). Alternatively, recombinant DNA techniques may be used.

The isolation of other monoclonal antibodies with the specificity of the monoclonal antibodies described herein can also be accomplished by one of ordinary skill in the art by producing anti-idiotypic antibodies (Herlyn et al., 1986). An anti-idiotypic antibody is an antibody which recognizes unique determinants present on the monoclonal antibody of interest.

In some aspects of this invention, it will be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6.sup.th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present invention can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. Preferably conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies of the invention may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease die biological half life of the antibody (U.S. Pat. No. 6,165,745).

Additionally, the antibodies of the invention may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell.sub.— with altered glycosylation mechanism (Shields, et al., 2002; Umana et al., 1999).

The antibodies of the invention can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive watersoluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies of the invention (EP 0 154 316 and EP 0 401 384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0 486 525.

The antibodies or fragments thereof of the present invention may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include .sup.125I, .sup.131I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Ithenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al., 1984); sulfhydral groups (Koyama 1994) of amino acid residues and carbohydrate groups (Rodwell et al., 1986; Quadri et al., 1993).

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependant on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The conjugated agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al., 1994; Upeslacis et al., 1995; Price, 1995).

Techniques for conjugating agents to antibodies are well known (Amon et al., 1985; Hellstrom et al., 1987; Thorpe, 1985; Baldwin et al., 1985; Thorpe et al., 1982), The antibodies of the invention or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oRDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al., 1984; Liu et al., 1985). When the binding molecules are antibodies, they can be conjugated by sulfhydryl bonding of the C-terminus hinge regions of the two heavy chains.

The antibodies or fragments thereof of the present invention may be linked to a moiety that is toxic to a cell to which the antibody is bound to form "depleting" antibodies. These antibodies are particularly useful in applications where it is desired to deplete an NK cell.

The antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this invention also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes of the invention. Those skilled in the art will know of other suitable carriers for binding monoclonal antibodies, or will be able to ascertain such, using routine experimentation.

B. Other OX40L Inhibitors

OX40L inhibitors include polynucleotides that decreases the biological activity of the OX40L gene and/or protein and can be, for example, a miRNA, a siRNA, a shRNA, a dsRNA or an antisense RNA directed to OX40L DNA or mRNA, or a polynucleotide encoding the miRNA, siRNA, shRNA, dsRNA or antisense RNA, or a vector comprising the polynucleotide.

"Short interfering RNAs" (siRNA) refer to double-stranded RNA molecules (dsRNA), generally, from about 10 to about 30 nucleotides in length that are capable of mediating RNA interference (RNAi). "RNA interference" (RNAi) refers to sequence-specific or gene specific suppression of gene expression (protein synthesis) that is mediated by short interfering RNA (siRNA). As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA. A siRNA may be chemically modified to increase its stability and safety. See, e.g. Dykxhoorn & Lieberman, 2006 and U.S. Patent Application Publication No.: 2008/0249055.

"Double stranded RNAs" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

"MicroRNAs" (miRNA) refer to single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

siRNA, dsRNA, and miRNA to inhibit gene expression can be designed following procedures known in the art. See, e.g., Dykxhoorn & Lieberman, 2006; Dykxhoorn et al., 2006; Aagaard & Rossi, 2007; de Fougerolles et al., 2007; Krueger et al., 2007; U.S. Patent Application Publication No.: 2008/0188430; and U.S. Patent Application Publication No.: 2008/0249055.

Delivery of siRNA, dsRNA or miRNA to a cell can be made with methods known in the art. See, e.g., Dykxhoorn & Lieberman, 2006; Dykxhoorn et al., 2006; Aagaard & Rossi, 2007; de Fougerolles et al., 2007; Krueger et al., 2007; U.S. Patent Application Publication No.: 2008/0188430; and U.S. Patent Application Publication No.: 2008/0249055. "Antisense" oligonucleotides have nucleotide sequences complementary to the protein coding or "sense" sequence. Antisense RNA sequences function as regulators of gene expression by hybridizing to complementary mRNA sequences and arresting translation (Mizuno et al., 1984; Heywood et al., 1986). An antisense polynucleotide comprising the entire sequence of the target transcript or any part thereof can be synthesized with methods known in the art. See e.g., Ferretti et al., 1986. The antisense polynucleotide can be placed into vector constructs, and effectively introduced into cells to inhibit gene expression (Izant et al., 1984). Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the gene is retained as a functional property of the polynucleotide.

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired T.sub.m). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991) or incorporating 2'-O-methyl ribonucleotides, phosphorothioate nucleotides, methyl phosphonate nucleotides, phosphotriester nucleotides, phosphorothioate nucleotides, phosphoramidates. Another example of the modification is replacement of a non-bridging phosphoryl oxygen atom with a sulfur atom which increases resistance to nuclease digestion. Increased antisense polynucleotide stability can also be achieved using molecules with 2-methyoxyethyl substituted backbones. See e.g., U.S. Pat. Nos. 6,451,991 and 6,900,187.

In another embodiment, ribozymes can be used (see, e.g., Cech, 1995; and Edgington, 1992; Hu et al., PCT Publication WO 94/03596). A ribonucleic acid enzyme ("ribozymes", "RNA enzyme", or "catalytic RNA") is an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. Methods of making and using ribozymes can be found in e.g., U.S. Patent Application Publication No. 2006/0178326.

"Triplex ribozymes" configurations allow for increased target cleavage relative to conventionally expressed ribozymes. Examples of triplex ribozymes include hairpin ribozymes and hammerhead ribozymes. Methods of making and using triplex ribozymes are found in, e.g., Aguino-Jarguin et al., 2008 and U.S. Patent Application Publication No. 2005/0260163.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996). Another subsequence, the h (hydrophobic) domain of signal peptides, was found to have similar cell membrane translocation characteristics (see, e.g., Lin et al., 1995). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

This disclosure features methods and compositions for decreasing the biological activity of OX40L in a cell. The OX40L inhibitors described herein may be expressed in cells using expression vectors, viral vectors, and other techniques known in the art for transferring genetic material to the cells of a patient with resulting therapeutic benefit to the patient. In some embodiments, polypeptides or polynucleotides encoding the polypeptides (e.g. antibodies and antibody fragments) described herein may be delivered to humans or to host cells.

In some embodiments, expression vectors encoding the OX40L inhibitor polynucleotide of interest is administered directly to the patient. The vectors are taken up by the target cells (e.g., neurons or pluripotent stem cells) and the polynucleotide is expressed. Recent reviews discussing methods and compositions for use in gene therapy include Eck et al., in Goodman & Gilman's The Pharmacological Basis of Therapeutics, 1996; Wilson, 1997; Wivel et al., 1998; Romano et al., 2000). U.S. Pat. No. 6,080,728 also provides a discussion of a wide variety of gene delivery methods and compositions.

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; and genetically-modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al., 2005).

Retroviruses are also useful as vectors and usually (with the exception of lentiviruses) are not capable of transfecting non-dividing cells. Accordingly, any appropriate type of retrovirus that is known in the art may be used, including, but not limited to, HIV, SIV, FIV, EIAV, and Moloney Murine Leukaemia Virus (MoMLV). Typically, therapeutically useful retroviruses including deletions of the gag, pol, or env genes.

In another aspect, the invention features the methods of inhibiting OX40L with a lentiviral vector that expresses an OX40L inhibiting polynucleotide in a patient. Lentiviruses are a type of retroviruses with the ability to infect both proliferating and quiescent cells. An exemplary lentivirus vector for use in gene therapy is the HIV-1 lentivirus. Previously constructed genetic modifications of lentiviruses include the deletion of all protein encoding genes except those of the gag, pol, and rev genes (Moreau-Gaudry et al., 2001)

Exemplary non-viral vectors for delivering nucleic acids include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff et al., 1992; Wolff et al., 1990. DNA-mediated gene transfer has also been characterized in liver, heart, lung, brain and endothelial cells. See Zhu et al., 1993; Nabel et al., 1989. DNA for gene transfer also may be used in association with various cationic lipids, polycations and other conjugating substances. See Przybylska et al., 2004; Svahn et al., 2004.

Methods of delivering nucleic acids using cationic liposomes are also well known in the art. Exemplary cationic liposomes for use in this invention are DOTMA, DOPE, DOSPA, DOTAP, DC-Chol, Lipid GL-67™, and EDMPC. These liposomes may be used in vivo or ex vivo to encapsulate a vector for delivery into target cells (e.g., neurons or pluripotent stem cells).

Typically, vectors made in accordance with the principles of this disclosure will contain regulatory elements that will cause constitutive expression of the coding sequence. Desirably, neuron-specific regulatory elements such as neuron-specific promoters are used in order to limit or eliminate ectopic gene expression in the event that the vector is incorporated into cells outside of the target region. Several regulatory elements are well known in the art to direct neuronal specific gene expression including, for example, the neural-specific enolase (NSE), and synapsin-1 promoters (Morelli et al., 1999).

Also provided are polynucleotides encoding substantially homologous and biologically equivalent polypeptides to the inventive polypeptides and polypeptide complexes. Substantially homologous and biologically equivalent intends those having varying degrees of homology, such as at least 80%, or alternatively, at least 85%, or alternatively at least 90%, or alternatively, at least 95%, or alternatively at least 98% homologous as defined above and which encode polypeptides having the biological activity as described herein. It should be understood although not always explicitly stated that embodiments to substantially homologous polypeptides and polynucleotides are intended for each aspect of this disclosure, e.g., polypeptides, polynucleotides and antibodies.

The polynucleotides of this disclosure can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell, described below. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

Also provided are host cells comprising one or more of the polypeptides or polynucleotides of this disclosure. Yet another aspect of the disclosure provides an isolated transformed host cell expressing an isolated polypeptide, an antibody or a biologically active fragment of the antibody of the disclosure. The isolated host cells can be a prokaryotic or a eukaryotic cell. In one aspect, the polypeptides are expressed and can be isolated from the host cells. In another aspect, the polypeptides are expressed and secreted. In yet another aspect, the polypeptides are expressed and present on the cell surface (extracellularly). Suitable cells containing the inventive polypeptides include prokaryotic and eukaryotic cells, which include, but are not limited to bacterial cells, algae cells, yeast cells, insect cells, plant cells, animal cells, mammalian cells, murine cells, rat cells, sheep cells, simian cells and human cells. A non-limiting example of algae cells is red alga *Griffithsia* sp. from which Griffithsin was isolated (Toshiyuki et al., 2005). A non-limiting example of plant cells is a *Nicotiana benthamiana* leaf cell from which Griffithsin can be produced in a large scale (O'Keefe, 2009). Examples of bacterial cells include *Escherichia coli* (Giomarelli et al. (2006), supra), *Salmonella enteric, Streptococcus gordonii* and *lactobacillus* (Liu et al., 2007; Rao et al., 2005; Chang et al., 2003; Liu et al., 2006). The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NSO, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia,* or *Pichia*. See e.g., U.S. Pat. Nos. 4,812,405; 4,818, 700; 4,929,555; 5,736,383; 5,955,349; 5,888,768 and 6,258, 559.

The OX40L inhibitor may also be a molecular inhibitor. Methods for screening various agents that modulate the activity of the protein are known in the art and are described herein. For the purposes of this disclosure, a "molecular inhibitor" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "molecular inhibitor." In addition, various natural sources can provide compounds for screening, such as plant or animal extracts, and the like. It should be understood, although not always explicitly stated that the molecular inhibitor is used alone or in combination with another agent, having the same or different biological activity as the agents identified by the inventive screen.

In some embodiments, the OX40L inhibitor is a small molecule capable of interacting with the OX40L protein. For the purpose of this invention, "small molecules" are molecules having low molecular weights (MW) that are, in one embodiment, capable of binding to a protein of interest thereby altering the function of the protein. Preferably, the MW of a small molecule is no more than 1,000. Methods for screening small molecules capable of altering protein function are known in the art. For example, a miniaturized arrayed assay for detecting small molecule-protein interactions in cells is discussed by You et al., 1997).

To screen for small molecule inhibitors in vitro, suitable cell culture or tissue infected with the microbial to be treated are first provided. The cells are cultured under conditions (temperature, growth or culture medium and gas ($CO_2$)) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several small molecule inhibitors can be assayed at the same time by noting genotypic changes, phenotypic changes or a reduction in microbial titer. The small molecule inhibitor can be directly added to the cell culture or added to culture medium for addition. As is apparent to those skilled in the art, an "effective" amount must be added which can be empirically determined.

II. Pharmaceutical Compositions

The present invention includes methods and compositions for inhibiting OX40L in a subject in need thereof. Administration of the compositions according to the present invention will typically be via any common route. This includes, but is not limited to parenteral, orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of an antibody are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2 day to twelve week intervals, more usually from one to two week intervals. The course of the administrations may be followed by assays for alloreactive immune responses and T cell activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The pharmaceutical compositions of the present invention can be formulated for parenteral administration, e.g., formulated for injection via the intravenous, intramuscular, sub-cutaneous, or even intraperitoneal routes. The preparation of an aqueous composition that contains an OX40L antibody or inhibitor that will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

III. Treatment of Disease

Methods of the present invention include treatment or prevention of inflammation and autoimmunity. Inflammation may be treated by administering OX40L inhibitors that inhibit the differentiation of inflammatory T cells, promote the generation and function of regulatory T cells by inducing IL-10 and inhibiting TNF-α, and reduce aberrant Th2 cell responses. The inflammation may be a component of an autoimmune disease or inflammation as a result of a non-autoimmune related dysfunction (e.g. cancer, injury, etc.). In further instances, the inflammation may be idiopathic, or of unknown cause.

The methods of the present invention also include the treatment or prevention of autoimmunity by the administration of OX40L inhibitors that eliminate or reduce aberrant T follicular helper cell-(Tfh) responses that may contribute to the pathogenicity of autoimmune disease. The compositions of the present invention have been shown to have in vivo utility for the treatment of GVHD and graft rejection.

Embodiments of the invention can be used to treat or ameliorate a number of immune-mediated, inflammatory, or autoimmune diseases, e.g., diabetes, graft rejection, etc. Examples of such diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen *nitidus*, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis *nodosa*/periarteritis *nodosa*), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes *dorsalis*, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, myasthenia gravis, immune thrombocytopenic purpura, antineutrophil cytoplasmic autoantibody-mediated disease, IgA-mediated vasculitis, Ig4-related disorders, and endometriosis.

IV. In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present invention, the compositions may be administered either in vitro, ex vivo, or in vivo. In certain in vitro embodiments, autologous T cells are incubated with compositions of this invention. The cells can then be used for in vitro analysis, or alternatively for ex vivo administration.

V. Combination Therapy

The compositions and related methods of the present invention, particularly administration of an OX40L antibody or antigen binding fragment may also be used in combination with the administration of traditional therapies. These include, but are not limited to, the administration of immunosuppressive or immunomodulating therapies or treatments.

In one aspect, it is contemplated that an OX40L antibody or antigen binding fragment is used in conjunction with an additional therapy. Alternatively, antibody administration may precede or follow the other treatment by intervals ranging from minutes to weeks. In embodiments where the other agents are administered separately, one would generally ensure that a significant period of time did not expire between the time of each delivery, such that the agent and antibody would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of the OX40L antibody or antigen binding fragment of the present invention to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

VI. Sequence Listing

SEQ ID NO: 1-mouse anti-hOX40L_19A3 (9295)-antibody heavy chain mIgGH2b
ATGGAATGGAGCTGGATCTTTCTCTTCCTCCTGTCAGGAACTGCAGGTGT
ACACTCTGAGGTCCAGCTTCAGCAGTCTGGGCCTGAGCTGGGGCAGCCTG
GGGCTTCAGTGAAGATATCCTGCAAGGCTTCTGGTTACTCATTCACTGGT
TACAGCATGCACTGGGTGAAGCAGAGCCATAGGAAAAGCCCTGAGTGGAT
TGGAAAAATTGATCCTTACAATGGTGTGACTACCTATAATCAGAGGTTCA
CGGGCAAGGCCACATTGACTGTCGACACATCTTCCAGCACAGCCTACATG
CATCTCAACAGCCTGACATCTGAGGACTCTGCAATCTTTTACTGTGCGAG
AGAGGGGTTTGCTTATTGGGGCCAAGGGACTCTGGTCTCTGTCTCTGAAG
CCAAAACAACACCCCCATCAGTCTATCCACTGGCCCTGGGTGTGGAGAT
ACAACTGGTTCCTCCGTGACTCTGGGATGCCTGGTCAAGGGCTACTTCCC
TGAGTCAGTGACTGTGACTTGGAACTCTGGATCCCTGTCCAGCAGTGTGC
ACACMTTCCCAGCTCTCCTGCAGTCTGGACTCTACACTATGAGCAGCTCA
GTGACTGTCCCCTCCAGCACCTGGCCAAGTCAGACCGTCACCTGCAGCGT
TGCTCACCCAGCCAGCAGCACCACGGTGGACAAAAAACTTGAGCCCAGCG
GGCCCATTTCAACAATCAACCCCTGTCCTCCATGCAAGGAGTGTCACAAA
TGCCCAGCTCCTAACCTCGAGGGTGGACCATCCGTCTTCATCTTCCCTCC
AAATATCAAGGATGTACTCATGATCTCCCTGACACCCAAGGTCACGTGTG
TGGTGGTGGATGTGAGCGAGGATGACCCAGACGTCCAGATCAGCTGGTTT
GTGAACAACGTGGAAGTACACACAGCTCAGACACAAACCCATAGAGAGGA
TTACACAGTACTATCCGGGTGGCTCAGCACCCTCCCCATCCAGCACCAGG
ACTGGATGAGTGGCAAGGAGTTCAAATGCAAGGTCAACAACAAAGACCTC
CCATCACCCATCGAGAGAACCATCTCAAAAATTAAAGGGCTAGTCAGAGC
TCCACAAGTATACATCTTGCCGCCACCAGCAGAGCAGTTGTCCAGGAAAG
ATGTCAGTCTCACTTGCCTGGTCGTGGGCTTCAACCCTGGAGACATCAGT
GTGGAGTGGACCAGCAATGGGCATACAGAGGAGAACTACAAGGACACCGC
ACCAGTCCTGGACTCTGACGGTTCTTACTTCATATATAGCAAGCTCAATA
TGAAAACAAGCAAGTGGGAGAAAACAGATTCCTTCTCATGCAACGTGAGA
CACGAGGGTCTGAAAAATTACTACCTGAAGAAGACCATCTCCCGGTCTCC
GGGTAAAGCTAGCTGAAAAA (SEQ ID NO: 1)

VI. Sequence Listing

SEQ ID NO: 2-mouse anti-hOX40L_19A3 (9295)-antibody heavy chain mIgGH2b. The classical TTXP signature is underlined
MEWSWIFLFLLSGTAGVHSEVQLQQSGPELGQPGASVKISCKASGYSFTG
YSMHWVKQSHRKSPEWIGKIDPYNGVITYNQRFTGKATLTVDTSSSTAYM
HLNSLTSEDSAIFYCAREGFAYWGQGTLVSVSEAK<u>TTPPS</u>VYPLAPGCGD
TTGSSVTLGCLVKGYFPESVTVTWNSGSLSSSVHTFPALLQSGLYTMSSS
VTVPSSTWPSQTVTCSVAHPASSTTVDKKLEPSGPISTINPCPPCKECHK
CPAPNLEGGPSVFIFPPNIKDVLMISLTPKVTCVVVDVSEDDPDVQISWF
VNNVEVHTAQTQTHREDYNSTIRVVSTLPIQHQDWMSGKEFKCKVNNKDL
PSPIERTISKIKGLVRAPQVYILPPPAEQLSRKDVSLICLVVGFNPGDIS
VEWTSNGHTEENYKDTAPVLDSDGSYFIYSKLNMKTSKWEKTDSFSCNVR
HEGLKNYYLKKTISRSPGKAS (SEQ ID NO: 2)

SEQ ID NO: 3-the leader peptide of the VH region of mouse anti-hOX40L_19A3 (9295)-antibody heavy chain mIgGH2b:
MEWSWIFLFLLSGTAGVHS (SEQ ID NO: 3)

SEQ ID NO: 4 Variable region of mouse anti-hOX40L_19A3 (9295)-antibody heavy chain mIgGH2b
EVQLQQSGPELGQPGASVKISCKASGYSFTGYSMHWVKQSHRKSPEWIGK
IDPYNGVTTYNQRFTGKATLTVDTSSSTAYMHLNSLTSEDSAIFYCAREG
FAYWGQGTLVSVSEAK SEQ ID NO: 4)

SEQ ID NO: 5-CDR1 of the VH region of mouse anti-hOX40L_19A3 (9295)-antibody heavy chain mIgGH2b
GYSFTGYSMH (SEQ ID NO: 5)

SEQ ID NO: 6-CDR2 of the VH region of mouse anti-hOX40L_19A3 (9295)-antibody heavy chain mIgGH2b
KIDPYNGVTTYNQRFTG (SEQ ID NO: 6)

SEQ ID NO: 7-CDR3 of the VH region of mouse anti-hOX40L_19A3 (9295)-antibody heavy chain mIgGH2b
EGFAY (SEQ ID NO: 7)

SEQ ID NO: 8-mouse anti-hOX40L_19A3 (9295)-antibody kappa light chain mIgK
<u>ATG</u>CATTTTCAAGTGCAGATTTTCAGCTTCCTGCTAATCAGTGCCTCAGT
CATAATGTCCAGAGGACAAATTGTTCTCACCCAGTCTCCAGCAATCATGT
CTGCATCTCCAGGGGAGAAGGTCACCATAACCTGCAGTGCCTCCTCAAGT
GTCCGTTATATTCACTGGTTCCAGCAGAAGCCAGGCACTTCTCCCAAACT
CTTGATTTATAGCACATCCGACCTGGCTTCTGGAGTCCCTGCTCGCTTCA
GTGGCGGTGGATCTGGGACCTCTTACTCTCTCACAATCAGCCGAATGGAG
GCTGAAGATGCTGCCACTTATTACTGCCAGCAAAGGACTGGTTACCCGCT
CACGTTCGGTGCTGGGACCAAGCTGGAGCTGAAACGGGCTGATGCTGCAC
CAACTGTATCCATCTTCCCACCATCCAGTGAGCAGTTAACATCTGGAGGT
GCCTCAGTCGTGTGCTTCTTGAACAACTTCTACCCCAAAGACATCAATGT
CAAGTGGAAGATTGATGGCAGTGAACGACAAAATGGCGTCCTGAACAGTT
GGACTGATCAGGACAGCAAAGACAGCACCTACAGCATGAGCAGCACCCTC
ACGTTGACCAAGGACGAGTATGAACGACATAACAGCTATACCTGTGAGGC
CACTCACAAGGCATCAACTTCACCCATCGTCAAGAGCTTCAACAGGAATG
AGTGTT<u>TAG</u>AAAA (SEQ ID NO: 8)

SEQ ID NO: 9-mouse anti-hOX40L_19A3 (9295)-antibody kappa light chain mIgK. The LE classical signature is underlined
MHFQVQIFSFLLISASVIMSRGQIVLTQSPAIMSASPGEKVTITCSASSS
VRYIHWFQQKPGTSPKLLIYSTSDLASGVPARFSGGGSGTSYSLTIMSS
AEDAATYYCQQRTGYPLTFGAGT<u>KLELK</u>RADAAPTVSIFPPSSEQLTSGG
ASVVCFLNNFYPKDINVKWKIDGSERQNGVLNSWTDQDSKDSTYSMSSTL
TLIKDEYERHNSYTCEATHKASTSPIVKSFNRNEC
(SEQ ID NO: 9)

SEQ ID NO: 10-the leader peptide of the VL region of mouse anti-hOX40L_19A3 (9295)-antibody kappa light chain mIgK:
MHFQVQIFSFLLISASVIMSRG (SEQ ID NO: 10)

SEQ ID NO: 11 Variable region of mouse anti-hOX40L_19A3 (9295)-antibody kappa light chain mIgK
QIVLTQSPAIMSASPGEKVTITCSASSSVRYIHWFQQKPGTSPKLLIYST
SDLASGVPARFSGGGSGTSYSLTISRMEAEDAATYYCQQRTGYPLTFGAG
TK (SEQ ID NO: 11)

SEQ ID NO: 12-CDR1 of the VL region of mouse anti-hOX40L_19A3 (9295)-antibody kappa light chain mIgK
SASSSVRYIH (SEQ ID NO: 12)

SEQ ID NO: 13-CDR2 of the VL region of mouse anti-hOX40L_19A3 (9295)-antibody kappa light chain mIgK
STSDLAS (SEQ ID NO: 13)

SEQ ID NO: 14-CDR3 of the VL region of mouse anti-hOX40L_19A3 (9295)-antibody kappa light chain mIgK
QQRTGYPLT (SEQ ID NO: 14)

SEQ ID NO: 15-DNA sequence of Clone 5C6 (8703) Hybridoma OX40L antibody heavy chain; chimeric on hIgG4
ATGAAGTGCTCCTGGGTCATCTTCTTCCTCATGGCCGTGGTGACCGGAGT
GAACTCTGAGGTGCAACTCCAGCAGTCAGGAGCTGAAATCGTGAAGCCAG
GCGCAAGTGTGAAGCTGTCCTGCACCGCTTCTGGGTTCAACATCAAGGAC
ACCTACATGCACTGGGTGAAGCAGCGGCCAGAAGCAGGGGTTGGAGTGGAT
TGGCAGAATTGACCCTAGGAACGACAACACCAAGTTTGACCCTAAGTTTC
GCGGGAAAGCAACACTGACTGCCGATACATCCAGCAATACTGCCTACCTG
CAGCTGAGCAGCCTTACATCCGAGGATGCCGCCGTCTACTACTGTGTGCC
CGTCCCCACAAGGAGCTGGTATTTTGATGTGTGGGGGCCGGCACTAGCG
TCACAGTCTCCAGCGCCAAAACAAAGGGCCCATCCGTCTTCCCCCTGGCG
CCCTGCTCCAGGAGCACCTCCGAGCACAGCCGCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA (SEQ ID NO: 15)

SEQ ID NO: 16-Amino Acid sequence of Clone 5C6 (8703) Hybridoma OX40L antibody heavy chain; the classical TXXP signature is underlined
MKCSWVIFFFLMAVVTGVNSEVQLQQSGAEIVKPGASVKLSCTASGFNIKD
TYMHWVKQRPEQGLEWIGRIDPRNDNTKFDPKFRGKATLTADTSSNTAYL
QLSSLTSEDAAVYYCVPVPTRSWYFDVWGAGTSVTVSSAK<u>TKGPS</u>VFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS (SEQ ID NO: 16)

SEQ ID NO: 17-Signal sequence of Clone 5C6 (8703) Hybridoma OX40L antibody heavy chain
MKCSWVIFFFLMAVVTGVNS (SEQ ID NO: 17)

SEQ ID NO: 18-Variable region of Clone 5C6 (8703) Hybridoma OX40L antibody heavy chain
EVQLQQSGAEIVKPGASVKLSCTASGFNIKDTYMHWVKQRPEQGLEWIGR
IDPRNDNTKFDPKFRGKATLTADTSSNTAYLQLSSLTSEDAAVYYCVPVP
TRSWYFDVWGAGTSVTVSSAK (SEQ ID NO: 18)

SEQ ID NO: 19-CDR1 of Clone 5C6 (8703) Hybridoma OX40L antibody heavy chain
GFNIKDTYMH (SEQ ID NO: 19)

SEQ ID NO: 20-CDR2 of Clone 5C6 (8703) Hybridoma OX40L antibody heavy chain
RIDPRNDNTKFDPKFRG (SEQ ID NO: 20)

VI. Sequence Listing

SEQ ID NO: 21-CDR3 of Clone 5C6 (8703) Hybridoma OX40L antibody heavy chain
VPTRSWYFDV (SEQ ID NO: 21)

SEQ ID NO: 22-DNA sequence of Clone 5C6 (8703) Hybridoma OX40L antibody light chain; chimeric on hIgGK-C backbone.
ATGGAGACCCATTCCCAAGTGTTCGTCTACATGCTGCTCTGGCTCTCCGG
AGTCGAAGGAGACATCGTGATGACCCAGTCTCACAAGTTCATGTCCACCA
GCGTGGGCGATAGAGTGTCTATTACCTGCAAGGCCTCACAGGACGTGGGG
AAATCGTCGTGTGGTTTCAGCAGAAGCCTGGCCAGAGTCCAAAGCTTTT
GATCTACTGGGCAAGCACCAGGCACACAGGGGTGCCCGATCGGTTTACAG
GCAGCGGGAGCGGCACTGATTTTACTCTGACAATTTCCAACGTCCAGAGC
GAGGACCTGGCTAATTATTTCTGTCAGCAGTACACTAGCTACCCCTACAT
GTACACATTCGGGGGGGCACAAAGCTCGAGATCAAACGAACTGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTATGCCTGCGA
AGTCACCCATCAGGGCCTGAGCTCGCCCGTCACAAAGAGCTTCAACAGGG
GAGAGTGTGCTAGCTGA (SEQ ID NO: 22)

SEQ ID NO: 23-Amino Acid sequence of Clone 5C6 (8703) Hybridoma OX40L antibody light chain; the LE classical signature is underlined. chimeric on hIgGK-C backbone
METHSQVFVYMLLWLSGVEGDIVMTQSHKFMSTSVGDRVSITCKASQDVG
KSVVWFQQKPGQSPKLLIYWASTRHTGVPDRFTGSGSGTDFTLTISNVQS
EDLANYFCQQYTSYPYMYTFGGGTK<u>LEI</u>KRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGECAS
(SEQ ID NO: 23)

SEQ ID NO: 24-Signal sequence of Clone 5C6 (8703) Hybridoma OX40L antibody light chain
METHSQVFVYMLLWLSGVEG (SEQ ID NO: 24)

SEQ ID NO: 25-Variable region of Clone 5C6 (8703) Hybridoma OX40L antibody light chain
DIVMTQSHKFMSTSVGDRVSITCKASQDVGKSVVWFQQKPGQSPKLLIYW
ASTRHTGVPDRFTGSGSGTDFTLTISNVQSEDLANYFCQQYTSYPYMYTF
GGGTK (SEQ ID NO: 25)

SEQ ID NO: 26-CDR1 of Clone 5C6 (8703) Hybridoma OX40L antibody light chain
KASQDVGKSVV (SEQ ID NO: 26)

SEQ ID NO: 27-CDR2 of Clone 5C6 (8703) Hybridoma OX40L antibody light chain
WASTRHT (SEQ ID NO: 27)

SEQ ID NO: 28-CDR3 of Clone 5C6 (8703) Hybridoma OX40L antibody light chain
QQYTSYPYMYT (SEQ ID NO: 28)

SEQ ID NO: 29-DNA sequence of Clone 44F3 (8704) Hybridoma OX40L antibody heavy chain chimeric on hIgG4
ATGGAGAGACACTGGATCTTGCTCCTGCTGTTGTCCGTGACCGCTGGAGT
CCATAGCCAGGTCCAACTGCAACAGTCCGGAGCAGAATTGCTAGGCCTG
GAGCAAGCGTCAAAATGTCCTGTAAGGCTTCCGGATACACCCTCGCAAGC
TACACCCTGCACTGGGTGAAGCAGCCCCTGGGCAGGGCTTGAATGGAT
TGGCTATATTAATCCCAACAGTGGCTATACCAACTACATCCAGAAGTTCA
AGGACAAGGCCACCCTCACAGCCGACAAGAGCTCATCAACTGCTTACATG
CAGCTGAGTTCTCTGACATCTGAGGACAGTGCCGTGTACTACTGCGCTAA
AGGCGGCGGGATCGGTATTGACAGATTGCGCCATGGATTATTGGGGCC
AGGGCACATCTGTGACTGTGTCTCCGGCAAAACAAAGGGCCCATCCGTC
TTCCCCCTGGCGCCCTGCTCCAGGAGCACCTCCGAGAGCACAGCCGCCCT
GGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAG
CTTGGGCACGAAGACCTACACCTGCAACGTAGATCACAAGCCCAGCAACA
CCAAGGTGGACAAGAGAGTTGAGTCCAAATATGGTCCCCCATGCCCACCC
TGCCCAGCACCTGAGTTCGAAGGGGGACCATCAGTCTTCCTGTTCCCCC
AAAACCCAAGGACACTCTCATGATCTCCCGGACCCCTGAGGTCACGTGCG
TGGTGGTGGACGTGAGCCAGGAAGACCCCGAGGTCCAGTTCAACTGGTAC
GTGGATGGCGTGGAGGTGCATAATGCCAAGACAAAGCCGCGGGAGGAGCA
GTTCAACAGCACGTACCGTGTGGTCAGCGTCCTCACCGTCCTGCACCAGG
ACTGGCTGAACGGCAAGGAGTACAAGTGCAAGGTCTCCAACAAAGGCCTC
CCGTCCTCCATCGAGAAAACCATCTCCAAAGCCAAAGGGCAGCCCCGAGA
GCCACAGGTGTACACCCTGCCCCCATCCCAGGAGGAGATGACCAAGAACC
AGGTCAGCCTGACCTGCCTGGTCAAAGGCTTCTACCCCAGCGACATCGCC
GTGGAGTGGGAGAGCAATGGGCAGCCGGAGAACTACAAGACCACGCC
TCCCGTGCTGGACTCCGACGGCTCCTTCTTCCTCTACAGCAGGCTAACCG
TGGACAAGAGCAGGTGGCAGGAGGGGAATGTCTTCTCATGCTCCGTGATG
CATGAGGCTCTGCACAACCACTACACACAGAAGAGCCTCTCCCTGTCTCT
GGGTAAAGCTAGCTGA (SEQ ID NO: 29)

SEQ ID NO: 30-Amino Acid sequence of Clone 44F3 (8704) Hybridoma OX40L antibody heavy chain chimeric on hIgG4; the classical TXXP signature is underlined
MERHWILLLLLSVTAGVHSQVQLQQSGAELARPGASVKMSCKASGYTLAS
YTLHWVKQRPGQGLEWIGYINPNSGYTNYIQKFKDKATLTADKSSSTAYM
QLSSLTSEDSAVYYCAKGGGDRYCTDCAMDYWGQGTSVTVSPAK<u>TKGP</u>SV
FPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPP
CPAPEFEGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGKAS (SEQ ID NO: 30)

SEQ ID NO: 31-Signal sequence of Clone 44F3 (8704) Hybridoma OX40L antibody heavy chain
MERHWILLLLLSVTAGVHS (SEQ ID NO: 31)

SEQ ID NO: 32-Variable region of Clone 44F3 (8704) Hybridoma OX40L antibody heavy chain
QVQLQQSGAELARPGASVKMSCKASGYTLASYTLHWVKQRPGQGLEWIGY
INPNSGYTNYIQKFKDKATLTADKSSSTAYMQLSSLTSEDSAVYYCAKGG
GDRYCTDCAMDYWGQGTSVTVSPAK (SEQ ID NO: 32)

SEQ ID NO: 33-CDR1 of Clone 44F3 (8704) Hybridoma OX40L antibody heavy chain
GYTLASYTLH (SEQ ID NO: 33)

SEQ ID NO: 34-CDR2 of Clone 44F3 (8704) Hybridoma OX40L antibody heavy chain
YINPNSGYTNYIQKFKD (SEQ ID NO: 34)

SEQ ID NO: 35-CDR3 of Clone 44F3 (8704) Hybridoma OX40L antibody heavy chain
GGGDRYCTDCAMDY (SEQ ID NO: 35)

SEQ ID NO: 36-DNA sequence of Clone 44F3 (8704) Hybridoma OX40L antibody light chain; chimeric on hIgGK-C backbone
ATGCACTCCCTTGCACTTCTGTTGAGCCTCTTGCTGCTGTGCGTGAGTGA
CAGCAGAGCTGAGACCACCGTGACACAGTCTCCTGCCTCTCTGTCAATGA
CCATCGGAGAAAAGGTGACCATCAGGTGCATGACTAGCATCGACATTGAC
GATGATATGAACTGGTACCAGCAGAAGCAGGGGAGCCTCCAAAGCTGCT
GATTTCCGAGGGAAAGACACTCCGCCCCGGGGTCCCCAGTCGGTTTTCC
AGCTCCGGGTACGGCACTGACTTTGTCTTCACTATTGAGAACATGCTCAG
CGAGGATGTGGCCGATTACTATTGTCTCCAAAGCGACAATCTGCCCTTCA
CATTCGGCTCCGGCACAAAACTCGAGATCAAACGAACTGTGGCTGCACCA
TCTGTCTTCATCTTCCCGCCATCTGATGAGCAGTTGAAATCTGGAACTGC
CTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTC
ACAGAGCAGGACAGCAAGGACAGCACCTACAGCCTCAGCAGCACCCTGAC
GCTGAGCAAAGCAGACTACGAGAAACACAAAGTCTATGCCTGCGAAGTCA
CCCATCAGGGCCTGAGCTCGCCCGTCACAAAGAGCTTCAACAGGGGAGAG
TGTGCTAGCTGA (SEQ ID NO: 36)

SEQ ID NO: 37-Amino Acid sequence of Clone 44F3 (8704) Hybridoma OX40L antibody light chain chimeric onhIgGK-C; the LE classical signature is underlined
MHSLALLLSLLLLCVSDSRAETTVTQSPASLSMTIGEKVTIRCMTSIDID
DDMNWYQQKPGEPPKLLISEGKTLRPGVPSRFSSSGYGTDFVFTIENMLS
EDVADYYCLQSDNLPFTFGSGTK<u>LEI</u>KRTVAAPSVFIFPPSDEQLKSGTA

VI. Sequence Listing

```
SVVCLLNNFYPREAKVQWKVDNALQSGNSQESVTEQDSKDSTYSLSSTLT
LSKADYEKHKVYACEVTHQGLSSPVTKSFNRGECAS
(SEQ ID NO: 37)

SEQ ID NO: 38-Signal sequence of Clone 44F3 (8704)
Hybridoma OX40L antibody light chain
MHSLALLLSLLLLCVSDSRA (SEQ ID NO: 38)

SEQ ID NO: 39-Variable region of Clone 44F3 (8704)
Hybridoma OX40L antibody light chain
ETTVTQSPASLSMTIGEKVTIRCMTSIDIDDDMNWYQQKPGEPPKLLISE
GKTLRPGVPSRFSSSGYGTDFVFTIENMLSEDVADYYCLQSDNLPFTFGS
GTK (SEQ ID NO: 39)

SEQ ID NO: 40-CDR1 of Clone 44F3 (8704) Hybridoma
OX40L antibody light chain
MTSIDIDDDMN (SEQ ID NO: 40)

SEQ ID NO: 41-CDR2 of Clone 44F3 (8704) Hybridoma
OX40L antibody light chain
EGKTLRP (SEQ ID NO: 41)

SEQ ID NO: 42-CDR3 of Clone 44F3 (8704) Hybridoma
OX40L antibody light chain
LQSDNLPFT (SEQ ID NO: 42)
```

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Characterization of OX40L Antibodies

The OX40L antibodies, 5C6 (also labeled as AB104_105.5C6.3F9), 19A3 (also labeled as AB104_105.19A3.2C4), and 44F3 (also labeled as AB104_105.44F3.2F7) were tested for their ability to promote cytokine production by naïve T cells co-cultured with mDCs using the following assays. The effect of the OX40L antibodies on the proliferation and viability of mDC cultures were also tested using the assays described in this example.

The OX40L antibody clones 5C6, 19A3, and 44F3 were found to 1) recognize unique epitopes on human OX40L, 2) inhibit the differentiation of IL-10 low/TNFa high producing inflammatory Th2 primed by TSLP-mDCs, 3) inhibit the proliferation and the production of TNF-a, and promote IL-10 by CD4 T cells cultured with OX40L-transfected cell line. These results are shown in FIGS. 1-8.

TSLP-mDCs and Naïve CD4 T Cell Coclture—Isolation and Culture of Blood Myeloid DCs (mDCs).

PBMCs were isolated form buffy coats or apheresis blood samples obtained from adult healthy volunteers. mDCs (lineage$^-$, CD4$^+$, CD11c$^+$) were enriched from the PBMCs by using Human pan-DC pre-enrichment kit (STEMCELL#19251) or Human myeloid DC enrichment kit (STEMCELL#19061) according to methods known in the art. The enriched mDCs were stained with FITC-CD3 (#349201), CD14 (#347493). CD16 (#555406), CD19 (#555412), CD20 (#555622), CD56 (#3032769), APC-CD11c (#340544), and V450-CD4 (#2342693) (all antibodies are from BD), and then linage$^-$ CD11c$^+$CD4$^+$ population was sorted as myeloid DCs by a FACS Aria2 (BD Biosciences). mDCs were cultured in RPMI+GlutaMAX (gibco), 10 mM HEPES (gibco), Penicillin/Streptmycin/L-Glutamine (gibco), 1 mM Sodium Pyruvate (SIGMA) and MEM Non-Essential Amino Acids Solution (Hyclone) containing 10% human AB serum (GemCell#100-512). Cells were seeded at a density of 1~2×10$^5$/200 ul medium in flat-bottomed 96-well plate in the presence of 20 ng/ml recombinant human TSLP. The recombinant human TSLP had been prepared in-house using an adenovirus vector system as described previously (Soumelis, et al., 2002). After incubation for 20~24 hours, mDCs are harvested and washed with culture medium.

Isolation of Naïve T Cells.

PBMCs were isolated form buffy coats blood or apheresis blood samples obtained from adult healthy volunteers. CD4$^+$ naïve T cells were enriched from the PBMCs using Human CD4$^+$ T cell Enrichment Cocktail (STEMCELL#15062) and Human Naïve CD4$^+$ T cell Enrichment kit (STEMCELL#19155). The enriched CD4$^+$ naïve T cells were stained with FITC-CD8 (#340692), CD14 (#347493), CD16 (#555406), CD19 (#555412), CD20 (#555622), CD25 (#340694), CD56 (#3032769), BDCA-2 (130-090-510; Miltenyi Biotech), CD11c (#3011791), TCRγδ (#347903), PE-CCR7 (#353204; BioLegend), PE-Cy7-CD45RO (#337168), APC-CD45RA (#304112; BioLegend), and V450-CD4 (#2342693) (all antibodies are from BD except BDCA-2, CCR7 and CD45RA). The linage$^-$CD4$^+$ CD45RA$^+$CD45RO$^-$CCR7$^+$ population was sorted as naïve CD4$^+$ T cells by a FACS Aria2.

DC and T Cell Coculture.

Freshly purified allogeneic naïve CD4$^+$ T cells (2.5×10$^4$ cells per well) were cocultured with TSLP DCs (5×10$^3$ cells per well) at DC/T cell ratio 1:5 in round-bottom 96-well culture plates in the presence of 50 ug/ml anti-OX40L mAb (ik-5, provided by Dr. Toshiyuki Hori), in-house anti-OX40L mAbs (5C6, 19A3, and 44F3). Mouse IgG2a (16-4724-85; eBioscience) and IgG2b (MAB004; R&D systems) were used as controls. After 6-8 days culture, naïve T cells were harvested and re-stimulated with immobilized anti-CD3 (OKT3: 1 ug/ml) plus anti-CD28 (1 ug/ml) at a concentration of 10$^5$ cells/100 ul in flat-bottom 96-well plates for 20~24 hours. The production of IL-4, IL-5, IL-10, IL-13, TNF-α and IFN-γ were measured by ELISA (all kits from R&D Systems) or Luminex (Milliopore).

Isolation of Bulk CD4$^+$ T Cells.

Bulk CD4$^+$ T cells were isolated from the buffy coat of blood from healthy adult volunteers by using Human CD4$^+$ T cell Enrichment Cocktail (STEMCELL#15062) followed by cell sorting as a CD4 Lineage fraction using FITC-CD8 (#340692), CD14 (#347493), CD16 (#555406), CD19 (#555412), CD20 (#555622), CD25 (#340694), CD56 (#3032769), BDCA-2 (130-090-510; Miltenyi Biotech), CD11c (#3011791), TCRγδ (#347903), and APC-Cy7 CD4 (#) (all antibodies are from BD except BDCA-2). After sorting, CD4$^+$ T cell were labeled by CSFE as the manufacture instructions L Cells and T Cell Coculture.

Before the coculture with T cells, 0.2 ug/ml of anti-CD3 antibody (OKT3) were put in the pre-seeded L cells and incubated for 1~2 hours. Then the CSFE-labeled CD4$^+$ T cells were added and cultured on the L cells in the presence of 1 ug/ml of anti-CD28 antibody (CD28.2, BD pharmingen) for 6 days. Activated CD4$^+$ T cell were re-stimulated with immobilized anti-CD3 (OKT3: 1 ug/ml) plus anti-CD28 (1 ug/ml) at a concentration of $10^5$ cells/100 ul in flat-bottom 96-well plates for 24 hours. The production of IL-4, IL-5, IL-10, IL-13, TNF-α and IFN-γ were measured by ELISA (all kits from R&D Systems) or Luminex (Milliopore).

Example 2: OX40 Ligand Contributes to Human Lupus Pathogenesis by Promoting T Follicular Helper Response Systemic lupus erythematosus (SLE) is a chronic systemic inflammatory autoimmune disease characterized by a breakdown of tolerance to nuclear antigens (Tsokos, 2011). SLE displays considerable heterogeneity in clinical manifestations and disease course. A more comprehensive understanding of SLE pathogenesis is long overdue; in the past 50 years, only one new drug has been approved for SLE treatment (Murphy et al., 2013; Stohl et al., 2012). Genome-wide association studies (GWAS) have identified many susceptibility loci for SLE, confirming that SLE patients display predisposing genetic factors (Cunninghame Graham et al., 2008; Delgado-Vega et al., 2009; Gateva et al., 2009; Han et al., 2009; International Consortium for Systemic Lupus Erythematosus et al., 2008). The interactions of the immune system with predisposing factors with environmental factors cause alterations in the functions of antigen presenting cells (APCs) and lymphocytes in SLE. APCs including dendritic cells (DCs) are aberrantly activated in SLE patients, and promote the activation of autoreactive T and B cells (Blanco et al., 2001; Blanco et al., 2008). The developed autoreactive plasma cells produce pathogenic autoantibodies directed against nuclear components and cause tissue injury.

Numerous studies with murine models have demonstrated that T follicular helper cells (Tfh) (Craft, 2012; Linterman et al., 2009; Vinuesa et al., 2005), a $CD4^+$ helper T (Th) cell subset specialized for provision of help to B cells (Crotty, 2011), play a major pathogenic role in lupus. For example, sanroque mice that display single recessive defect in Roquin gene develop a lupus-like autoimmune disease by generating excessive Tfh cell responses (Linterman et al., 2009; Vinuesa et al., 2005). Tfh cells are essential for the formation of germinal centers (GCs), the site for the selection of high-affinity B cells and for the development of B cell memory (MacLennan, 1994; Vinuesa and Cyster, 2011). Tfh cells are equipped with multiple features required for B cell help (Crotty, 2011; King et al., 2008). IL-21 secreted by Tfh cells and their precursors (Bentebibel et al., 2011; Bryant et al., 2007; Chtanova et al., 2004) potently promotes the growth, differentiation, and class-switching of B cells (Spolski and Leonard, 2008). Inducible co-stimulator (ICOS) is highly expressed by GC Tfh cells and mediates the interaction with B cells (Crotty, 2011; King et al., 2008; Xu et al., 2013). CD40 ligand (CD40L) expressed by Tfh cells provides signals to B cells through CD40 for their differentiation and class-switching (Banchereau et al., 1994). The importance of these Tfh molecules in lupus pathogenesis is underscored by the observations in lupus mouse models that inhibition of the function of CD40L (Boumpas et al., 2003; Kalled et al., 1998), ICOS (Odegard et al., 2008), IL-21 and/or IL-21 receptor (Bubier et al., 2009; Herber et al., 2007) delays the disease course and improves the clinical symptoms. Furthermore, an inhibition of the generation of Tfh cells in lupus prone sanroque mice model by deleting SAP molecule abrogates the development of renal pathology by inhibiting the (Linterman et al., 2009). These studies provide a strong rationale to suppress the generation and/or activity of Tfh cells for the prevention of lupus disease from subjects with susceptible loci and/or for the treatment of lupus patients.

In human lupus, a majority of IgG class autoantibody-producing B cells are somatically mutated (Tiller et al., 2007), suggesting that they are derived from GCs through interactions with Tfh cells. Multiple studies show that the frequency of blood Tfh cells with active phenotype is increased in active SLE patients (He et al., 2013; Simpson et al., 2000). Furthermore, Tfh cells are also found in T-cell and B-cell aggregates and ectopic germinal centers in the kidneys of patients with lupus nephritis (Chang et al., 2011; Liarski et al., 2014). These observations support the pathogenic role of Tfh cells in human lupus. However, the mechanisms involved in increased Tfh response in SLE patients remains unknown.

Here it is shown that OX40 ligand (OX40L) expressed by myeloid APCs contributes to the aberrant Tfh response in SLE. OX40L was expressed by myeloid APCs in blood as well as in inflamed tissues in adult and pediatric active SLE patients. OX40L stimulation induced human $CD4^+$ T cells to express Tfh-associated molecules, and was sufficient to induce them to become functional B cell helpers. Finally, it is shown here that immune complexes (ICs) containing ribonucleoprotein (RNP) present in lupus sera induce OX40L expression by myeloid APCs through activation of TLR7. Thus, this study shows that the RNP IC-OX40L axis likely provides an amplification loop of the generation of autoantibodies in SLE.

Materials and Methods

Patient Samples—

Adult SLE patients (total 61:53 female and 8 male) and pediatric SLE patients (total 38: 34 female and 4 male) who met the American College of Rheumatology revised criteria for SLE (Hochberg, 1997) were enrolled. All clinical and biologically relevant information of the patients is shown in Tables 1-2 below. Clinical disease activity was assessed using the SLE Disease Activity Index (SLEDAI). Active patients were defined as SLEDAI score ≥6. For adult SLE samples, blood samples from routine lab analysis were used after informed consent was obtained. For pediatric SLE samples, the study was approved by the Institutional Review Board of Baylor Research Institute and informed consent was obtained from all the participants or their parents. Control PBMCs were obtained either from buffy coat, blood draw, or apheresis blood samples from adult volunteers.

TABLE 1

Clinical and laboratory paramers of adult SLE patients included in the study.

| Patient number | Age | Sex | Clinical failure | Flare | Corticotherapy (dose, mg/day) | Associated treatment | SLEDAI |
|---|---|---|---|---|---|---|---|
| 1 | 54 | M | A, C, H , R | | | HCQ | 2 |
| 2 | 27 | F | A, C, H, N, PP, APS | A | 10 | MTX, RTX | 8 |
| 3 | 35 | F | A, H | A | 20 | HCQ | 4 |

TABLE 1-continued

Clinical and laboratory paramers of adult SLE patients included in the study.

| Patient number | Age | Sex | Clinical failure | Flare | Corticotherapy (dose, mg/day) | Associated treatment | SLEDAI |
|---|---|---|---|---|---|---|---|
| 4 | 33 | F | C, H, APS | | 10 | HCQ, MMF | 0 |
| 4 | 34 | F | C, H, APS | | 10 | HCQ, MMF | 2 |
| 5 | 35 | F | A, C, R | | 7 | HCQ, AZA | 2 |
| 6 | 35 | F | A, C, H, R, APS | | 50 | CYC | 4 |
| 7 | 41 | F | A, C, H, R | N, R | 10 | MPA | 26 |
| 8 | 34 | M | A, C, H, R | C, R, V | | | 20 |
| 9 | 40 | F | A, C, H | | | HCQ, MTX | 0 |
| 10 | 32 | F | A, C, H, R | | | HCQ | 22 |
| 10 | 31 | F | A, C, H, R | A, C, R | 25 | HCQ, CYC | 4 |
| 10 | 31 | F | A, C, H, R | R | 25 | HCQ, CYC | 8 |
| 10 | 31 | F | A, C, H, R | R | 20 | HCQ, CYC | 8 |
| 11 | 41 | F | A, H, APS | | 3 | HCQ, MMF | 4 |
| 12 | 72 | M | C, H, N, PP, R | C, N, PP, R | | HCQ | 24 |
| 13 | 36 | F | A, C, R | | 10 | AZA | 4 |
| 14 | 22 | F | A, C, R | | | AZA | 2 |
| 15 | 22 | F | A, C, H, R | R | 2.5 | MMF | 12 |
| 16 | 23 | M | H, R | R | | MMF | 8 |
| 16 | 22 | M | H, R | | | MMF | 4 |
| 17 | 60 | M | A, H, N, R | A, N, R | 10 | HCQ | 19 |
| 17 | 58 | M | A, H, N, R | | 10 | HCQ | 2 |
| 17 | 59 | M | A, H, N, R | | 5 | HCQ | 2 |
| 18 | 25 | F | A, C, H, PP, APS | | 30 | HCQ, RTX | 4 |
| 18 | 25 | F | A, C, H, PP, APS | | 25 | HCQ, RTX | 4 |
| 18 | 25 | F | A, C, H, PP, APS | A | 40 | HCQ, RTX | 8 |
| 19 | 18 | F | A, C, H, R | A, C, N, R | 20 | HCQ, MMF | 24 |
| 19 | 19 | F | A, C, H, R | | 30 | MPA | 0 |
| 19 | 19 | F | A, C, H, R | | 7 | MPA | 0 |
| 19 | 20 | F | A, C, H, R | A | 6 | MPA | 8 |
| 19 | 20 | F | A, C, H, R | | 6 | HCQ, MPA | 2 |
| 20 | 40 | F | A, C, R, APS | | 6 | MMF | 2 |
| 21 | 58 | F | A, C, H | | 3 | HCQ, MTX | 4 |
| 22 | 42 | F | A, H, R | R, V | | | 33 |
| 23 | 44 | M | A, H, PP, R | | 8 | MMF | 4 |
| 24 | 18 | F | H | | | | 3 |
| 25 | 27 | F | A, C, R | A | 10 | HCQ, MMF | 8 |
| 26 | 48 | F | D, H, M, PP, R | R | 40 | AZA | 16 |
| 26 | 46 | F | D, H, M, PP, R | | 20 | MMF | 4 |
| 26 | 46 | F | D, H, M, PP, R | | 5 | HCQ, MMF | 4 |
| 27 | 39 | F | A, H, N, R, APS | | 5 | HCQ, AZA | 2 |
| 28 | 35 | F | A, C, H, N | A | 10 | | 8 |
| 28 | 35 | F | A, C, H, N | A | 15 | | 8 |
| 28 | 34 | F | A, C, H, N | | 7.5 | AZA | 4 |
| 29 | 58 | F | A, H | A | 10 | AZA | 8 |
| 29 | 57 | F | A, H | A | 15 | HCQ, AZA | 6 |
| 30 | 35 | F | A, C, H, M, N, R | A, R | 20 | HCQ, MMF | 16 |
| 30 | 35 | F | A, C, H, M, N, R | | 17.5 | HCQ, MMF | 2 |
| 31 | 58 | F | A, C | | 17.5 | HCQ | 2 |
| 32 | 25 | F | A, H | | | MTX | 4 |
| 32 | 25 | F | A, H | A | 10 | MTX | 8 |
| 33 | 38 | F | A, H, R | R | | | 16 |
| 33 | 39 | F | A, H, R | | 8 | MMF | 2 |
| 34 | 17 | M | A, C, PP, R | R | 10 | HCQ, MMF | 12 |
| 35 | 21 | F | A, C, APS | | | HCQ | 4 |
| 35 | 21 | F | A, C, APS | | | HCQ | 4 |
| 35 | 21 | F | A, C, APS | | | HCQ | 4 |
| 36 | 19 | F | A, C, R | R | 5 | HCQ, MMF | 8 |
| 37 | 39 | F | A, C, R | | 3 | MMF, RTX | 2 |
| 38 | 51 | F | A, H, R | A | 10 | Abatacept | 8 |
| 38 | 51 | F | A, H, R | R | 8 | Abatacept | 8 |
| 38 | 52 | F | A, H, R | R | 9 | Abatacept | 12 |
| 38 | 52 | F | A, H, R | A | 10 | | 8 |
| 39 | 57 | F | A, H, PP, R | R | 5 | HCQ | 17 |
| 39 | 56 | F | A, H, PP, R | R | 20 | HCQ | 4 |
| 40 | 65 | F | H, APS | | | | 0 |
| 41 | 38 | F | A, C, PP | C | 5 | HCQ | 6 |
| 42 | 34 | F | A, C, H, N | | 10 | HCQ, MMF | 4 |
| 43 | 28 | F | R, H, A | R | 5 | HCQ, MMF | 9 |
| 44 | 63 | F | C, A, R | H, A | 30 | HCQ, AZA | 22 |
| 45 | 22 | F | C, A | PP | 30 | HCQ, CYC | 23 |
| 46 | 37 | M | A, R, D | | 5 | MMF | 2 |
| 47 | 37 | F | A | | 7 | HCQ | 2 |
| 48 | 57 | F | A | | 5 | HCQ | 4 |
| 49 | 53 | F | A | | 5 | MTX | 3 |
| 50 | 80 | F | A, N, PP | | 9 | | 4 |
| 51 | 20 | F | R | | | HCQ, MTX | 2 |

TABLE 1-continued

Clinical and laboratory paramers of adult SLE patients included in the study.

| Patient number | Age | Sex | Clinical failure | Flare | Corticotherapy (dose, mg/day) | Associated treatment | SLEDAI |
|---|---|---|---|---|---|---|---|
| 52 | 41 | F | C, A, R | | | | 8 |
| 53 | 43 | F | A | A | 20 | | 8 |
| 54 | 50 | F | H | | | HCQ | 4 |
| 55 | 55 | F | A, C | | | MMF | 4 |
| 56 | 27 | F | A, R | | | | 16 |
| 57 | 25 | F | A, R, H, PP | | | | 23 |
| 58 | 18 | F | A, H | A | 12.5 | AZA | 8 |
| 59 | 35 | F | A | | 10 | HCQ | 4 |
| 60 | 37 | F | A, C | A | 10 | HCQ | 14 |
| 61 | 41 | F | A, C, H | A, R | 5 | HCQ | 25 |

TABLE 2

Clinical and laboratory paramers of pediatric SLE patients included in the study.

| Patient number | Age | Sex | Flare | Corticotherapy (dose, mg/day) | Associated treatment | SLEDAI |
|---|---|---|---|---|---|---|
| 1 | 18 | F | | | HCQ, MPA | 0 |
| 2 | 17 | F | | 9 | HCQ, MPA | 2 |
| 3 | 17 | F | R | | HCQ, MPA | 10 |
| 4 | 17 | F | | 10 | HCQ, MMF | 5 |
| 5 | 15 | F | | | MPA | 2 |
| 6 | 12 | F | R | 10 | HCQ, MMF | 14 |
| 7 | 16 | F | | | HCQ, MMF | 2 |
| 8 | 15 | F | | | HCQ, MPA | 4 |
| 9 | 14 | F | | | HCQ, MPA | 4 |
| 10 | 17 | F | R | | HCQ, MPA | 6 |
| 11 | 16 | F | | 5 | HCQ, MPA | 4 |
| 12 | 15 | M | | 10 | HCQ, MMF | 0 |
| 13 | 17 | F | | 5 | HCQ, MPA | 0 |
| 14 | 15 | F | V | | MMF | 8 |
| 15 | 16 | F | | | MMF | 2 |
| 16 | 15 | F | | | HCQ, MMF | 0 |
| 17 | 15 | F | | 120 | HCQ | 6 |
| 18 | 16 | F | | 3 | HCQ, MMF | 4 |
| 19 | 15 | F | R | 10 | HCQ, MMF | 4 |
| 20 | 17 | F | A, R | 10 | MMF | 10 |
| 21 | 14 | F | | 10 | MMF | 5 |
| 22 | 17 | M | R | | HCQ | 10 |
| 23 | 14 | F | | | HCQ | 4 |
| 24 | 10 | F | R | 5 | HCQ | 6 |
| 25 | 17 | F | C | | HCQ | 6 |
| 26 | 11 | F | | 10 | HCQ, MMF | 0 |
| 27 | 13 | F | R | | HCQ, MMF | 6 |
| 28 | 16 | F | | | HCQ | 2 |
| 29 | 12 | F | | 10 | HCQ, MMF | 8 |
| 30 | 17 | F | R | 10 | HCQ, MPA | 10 |
| 31 | 15 | F | A | 10 | HCQ, MMF | 4 |
| 32 | 16 | M | | 10 | HCQ, MMF | 4 |
| 33 | 15 | M | R | 10 | HCQ, MMF, MTX | 8 |
| 34 | 17 | F | R | 10 | HCQ | 8 |
| 35 | 16 | F | | 10 | HCQ, MMF | 4 |
| 36 | 16 | F | R | 10 | HCQ, MMF, MTX | 8 |
| 37 | 17 | F | | 2 | HCQ, MMF | 2 |
| 38 | 16 | F | | 5 | MMF | 4 |

Abbreviations: F: female, M: male, A: articular, C: cutaneous, D: digestive, H: haematologic, M: mycardic, N: neurologic, PP: pleuro-pericardic, R: renal, V: vascular, APS: anti-phopholipid syndrome, HCQ: hydroxychloroquin, AZA: azathioprin, CYC: cyclophosphamide, MMF: mycophenolate mofetil, MPA: mycophenolic acid, MTX: methotrexate, RTX: rituximab.

Skin and Kidney biopsies (class IV lupus nephritis) were randomly selected in regard to patient characteristics from the adult SLE population. Control skin samples were obtained from patients undergoing plastic surgery. Control kidney samples were obtained from cancer patients who underwent nephrectomy.

Phenotyping of Blood Immune Cells by Flow Cytometry—

For the analysis of OX40L expression, whole blood samples were stained with anti-CD14-PC5, CD16-FITC, CD11c-APC, HLA-DR-PC7, and OX40L-PE mAbs, and red blood cells were lysed with Versalyse (Beckman Coulter). For the analysis of blood Tfh cells, whole blood samples were stained with anti-CXCR5-AF488, CCR6-PE, CXCR3-PC5, CCR4-PC7, CD3-AF700, CD8-APCH7, CD4-Pacific Blue (all from Becton Dickinson), CD45RA-ECD (Beckman Coulter), ICOS-APC (Biolegend) and CD45-Pacific Orange (Invitrogen). Data were collected using a BD LSR II instrument (BD Biosciences) and analyzed with Flowjo software (Tree Star Inc.).

Skin and Kidney Biopsy Analysis—

OX40L and CD11c expression in skin and kidney biopsies from SLE patients and subjects without autoimmune diseases was analyzed using immunofluorescence microscopy. Briefly, 5-μm-thick sections of formalin-fixed, paraffin-embedded tissues from skin and kidney were deparaffinized and subjected to a heat-induced epitope retrieval step. Slides were rinsed in cool running water and washed in Tris-buffered saline, pH 7.4, before overnight incubation with primary anti-CD11c (Novocsatra, clone 5D11), and anti-OX40L (R&D Systems, clone 159403) or isotype-matched control antibody. Slides were then washed three times and incubated with appropriate secondary antibodies: AF488-conjugated anti-mouse or rat or AF568-conjugated anti-mouse (Invitrogen). Immunofluorescence image was analyzed on an Olympus BX51/52 system microscope coupled to a Cytovision System (Applied Imaging).

Phenotypic Analysis of Tonsil Samples—

Tonsil samples were obtained from healthy subjects undergoing tonsillectomies, and single cells were collected by mechanical disruption. For surface staining, cells were incubated with fluorochrome conjugated antibodies CD11c-PC7 (B-ly6), HLA-DR-PerCP (L243), CD19-FITC (HIB19), CD19-APC (HIB19) and 41BBL-PE (C65-485) from BD Biosciences, OX40L-PE (ANC10G1) from Ancell Corporation, CD14-APC-AF750 (TuK4), CD16-APC (3G8) and CD3-PB (UCHT1) from Invitrogen, ICOSL-FITC (MIH12) from Miltenyi, GITRL-PE (109101) from R&D in the presence of LIVE/DEAD FIXABLE Aqua (Invitrogen) for 15 minutes, followed by analysis on the BD LSRII. Data were further analysed using FlowJo software (Tree Star Inc.).

Culture of Th Cells—

Naïve (CD45RA$^+$CCR7$^+$) and memory (CD45RA$^-$) Th cells were sorted by flow cytometry as described before (Schmitt et al., 2009). Th cells were stimulated overnight with CD3/CD28 Dynabeads (Invitrogen) in RPMI complete medium supplemented with 10% FCS. Cells were then transferred to flat-bottomed 96 well plates coated with CD3 mAb (5 µg/ml, OKT3) supplemented with soluble CD28 mAb (1 µg/ml. CD28.2), in the presence or absence of recombinant IL-12 (100 pg/ml), and/or soluble OX40L (100 ng/ml (R&D systems). In some experiments, sorted naïve Th cells were cultured with allogeneic monocytes (CD14$^+$ cells) isolated by sort from active SLE patient PBMCs (T: monocyte ratio=1:1). T cells were harvested day 4 (for CD3/CD28 stimulated T cells) or at day 7 (for monocyte-T co-culture) for phenotyping with anti-CXCR5-AF647, anti-CD40L APC-eFluor 780 and anti-ICOS biotin/Streptavidin-PerCP; and for co-culture with B cells. For the assessment of IL-21 expression (with anti-IL21-PE), cultured cells were re-stimulated with 25 ng/ml PMA, 1 µg/ml ionomycin for 6 hours in the presence of Brefeldine (eBioscience) and monensin for the last 4 hours.

Co-Culture of Th and B Cells—

Activated Th cells were co-cultured with autologous naïve or memory B cells ($5 \times 10^3$ T cells for $40 \times 10^3$ memory B cells per well) in 96-well round-bottom plates in Yssel medium/10% FBS in the presence of endotoxin-reduced SEB (0.25 ng/ml; Toxin technology, Inc.). IgG produced in the cultures were analyzed by ELISA at day 14.

Culture of Monocytes—

CD14$^+$ monocytes were purified from blood samples from healthy donors by negative selection (Schmitt et al., 2009) and then exposed to SLE serum (10%) or control serum for 3 days in a 6 well-plate. The phenotype was analyzed by FACS with anti-CD14-PC5, anti-HLA-DR-PC7, and anti-OX40L-PE. TLR3 (poly-IC, 10 µg/ml), TLR7 (R837, 5 µg/ml), TLR9 (ODN2216, 10 µg/ml) agonists were purchased from InvivoGen. The TLR7 inhibitor IRS-661 (1 µM)(Barrat et al., 2005) was incubated for 10 min with the monocytes before with the addition of SLE serum or anti-RNP IgG (50 µg/ml).

Anti-RNP Purification—

Anti-RNP titer levels were measured using commercially available enzyme-linked immunosorbant assay (ELISA) kits (Corgenix). Samples were compared with a positive control provided by the manufacturer. Positive anti-RNP samples had an activity greater than 22 U/ml. IgG were purified from anti-RNP$^+$ SLE patients' serum samples using HiTrap Protein G HP column (GE Healthcare). Purified IgG were desalted and then quantified.

Nanostring—

Th cells cultured with IL-12 and/or sOX40L for 48 h were lysed in RLT buffer. Total RNA was purified using RNeasy Micro Kit (Qiagen). The NanoString reactions were done according to manufacturer's instructions. The data were normalized to housekeeping genes included in the codeset.

Statistical Analysis—

The normality of the variable distribution was assessed and as the normality of the distribution was rejected, analyses were performed by the non-parametric paired Wilcoxon test or unpaired Mann-Whitney U tests as appropriate. When necessary, comparisons were analyzed with Kruskall Wallis test followed by Dunn post hoc test. To compare more than three parameters, one-way ANOVA with multiple comparison tests was used. Correlation between variables was determined by using the Spearman test. All statistical analyses were performed using StatView 5.0 software (SAS Institute).

Results

OX40L is Abundantly Expressed in Inflamed Tonsils—

Applicants previously demonstrated that dermal CD14+ DCs preferentially induce the generation of Tfh-like cells in vitro (Klechevsky et al., 2008). Skin DC subsets including dermal CD14+ DCs migrate into the draining lymph nodes (Segura et al., 2012), and interact with T cells at the T cell zone. CD206+ DCs in the lymph nodes, a proposed counterpart of migrating dermal CD14+ DCs, promote naïve Th cells to produce CXCL13 (Segura et al., 2012), the chemokine abundantly expressed by Tfh cells (Bentebibel et al., 2011; Kim et al., 2004). These observations suggest the involvement of dermal CD14+ DCs in the generation of Tfh cells and antibody responses in draining lymph nodes of skin. However, the phenotype of APCs associated with Tfh responses in inflammatory lymphoid organs such as tonsils has not been determined.

Figure 1:
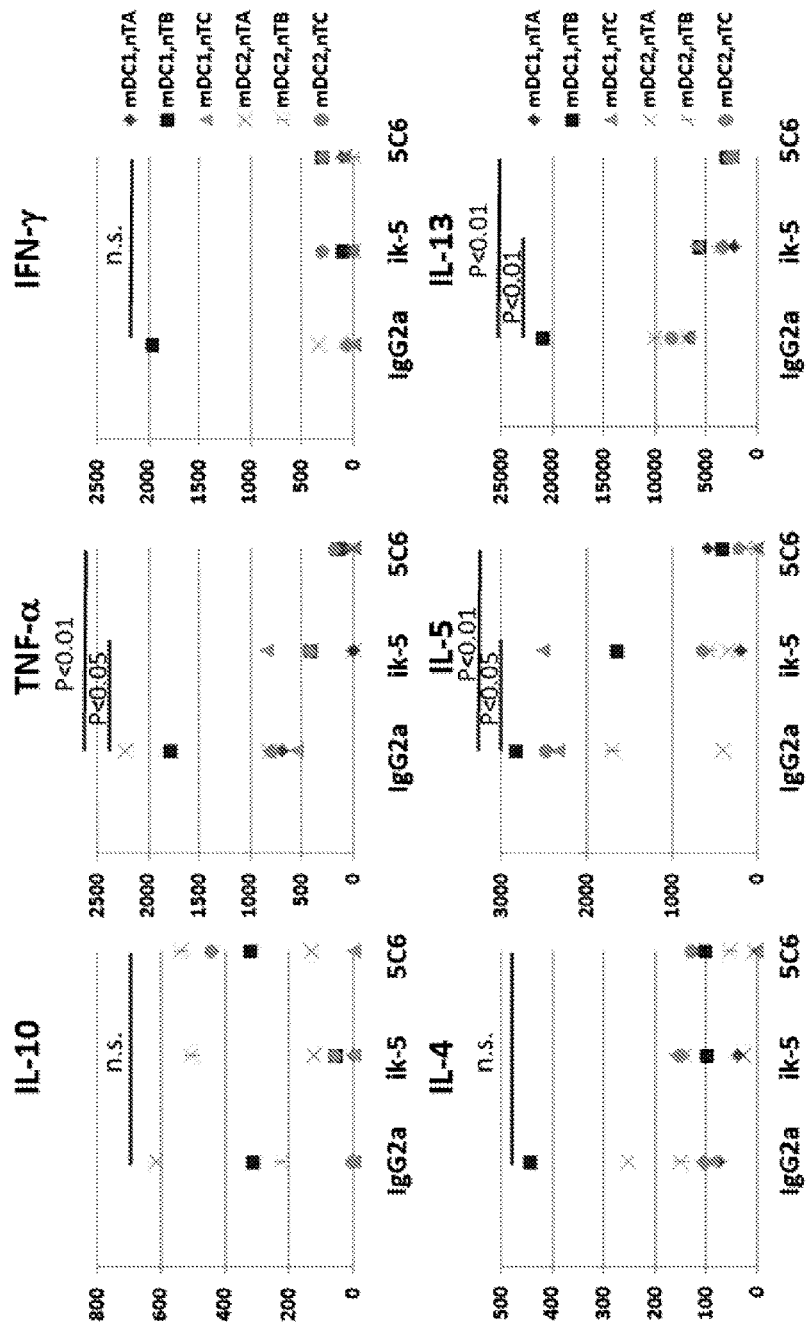
FIG. 1 depicts the results of an assay in which Dendritic cells and T cells were cocultured in the presence of 5C6 (AB104_105.5C6.3F9) anti-OX40L mAb, ik-5 anti-OX40L mAb, or control antibody (IgG2a) according to methods described in Example 1. The production of IL-4, IL-5, IL-10, IL-13, TNF-α and IFN-γ were measured by ELISA.
Figure 2:
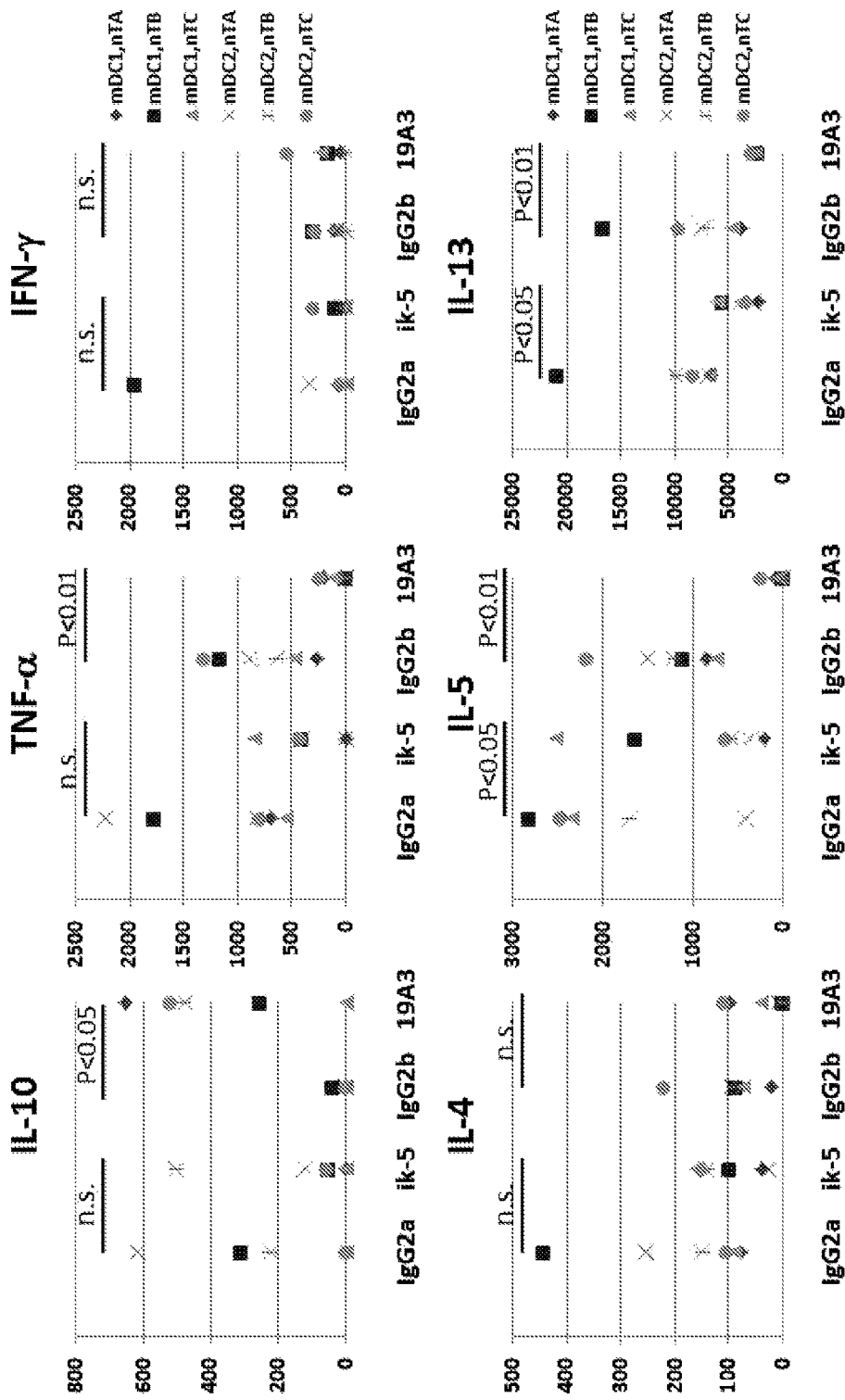
FIG. 2 depicts the results of an assay in which Dendritic cells and T cells were cocultured in the presence of 19A3 (AB104_105.19A3.2C4) anti-OX40L mAb, ik-5 anti-OX40L mAb, or control antibodies (IgG2a and IgG2b) according to methods described in Example 1. The production of IL-4, IL-5, IL-10, IL-13, TNF-α and IFN-γ were measured by ELISA.
Figure 3:
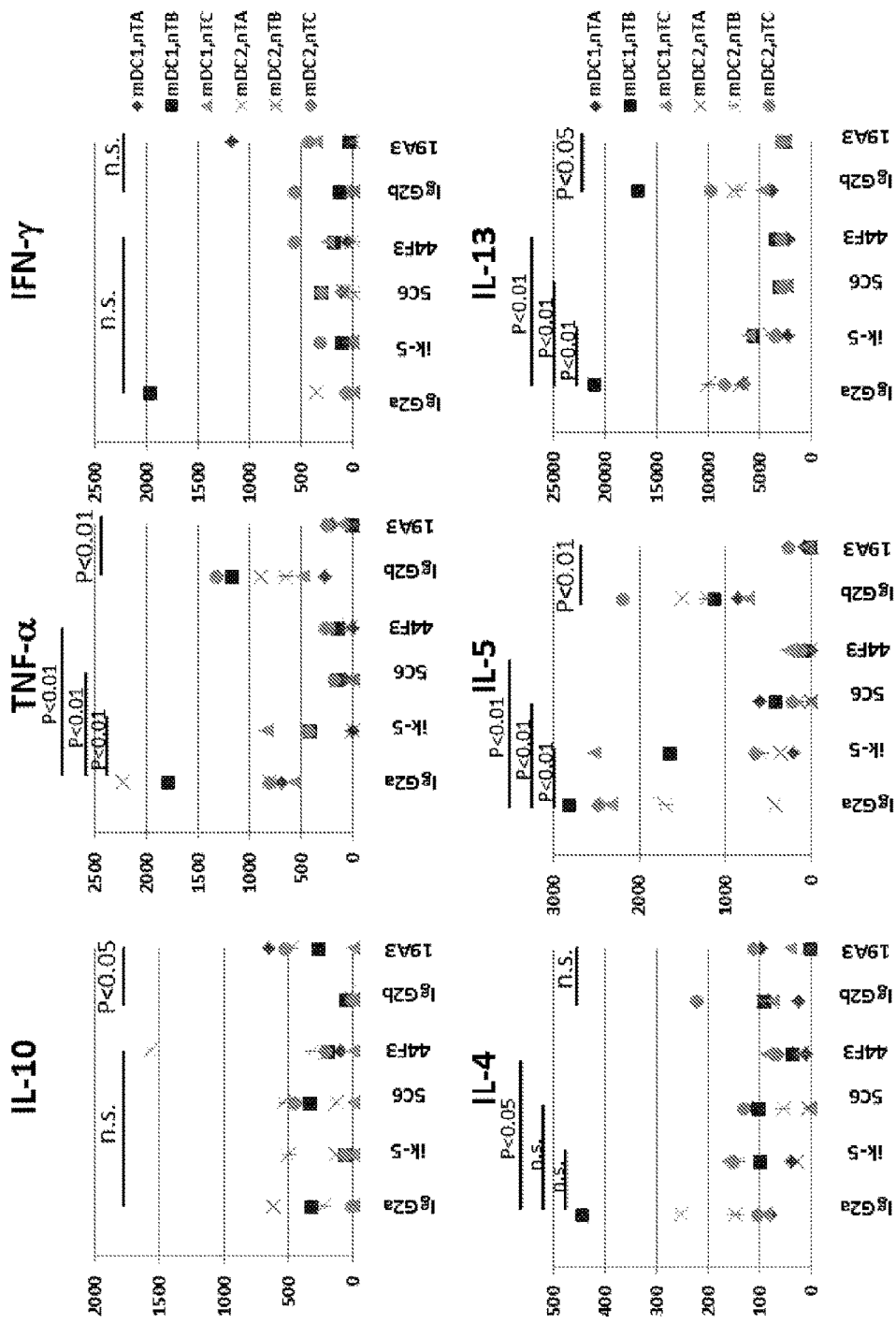
FIG. 3 depicts the results of an assay in which Dendritic cells and T cells were cocultured in the presence of 5C6 (AB104_105.5C6.3F9) anti-OX40L mAb, 44F3 (AB104_105.44F3.2F7) anti-OX40L mAb, 19A3 (AB104_105.19A3.2C4) anti-OX40L mAb, ik-5 anti-OX40L mAb, or control antibodies (IgG2a and IgG2b) according to methods described in Example 1. The production of IL-4, IL-5, IL-10, IL-13, TNF-α and IFN-γ were measured by ELISA.
Figure 4:
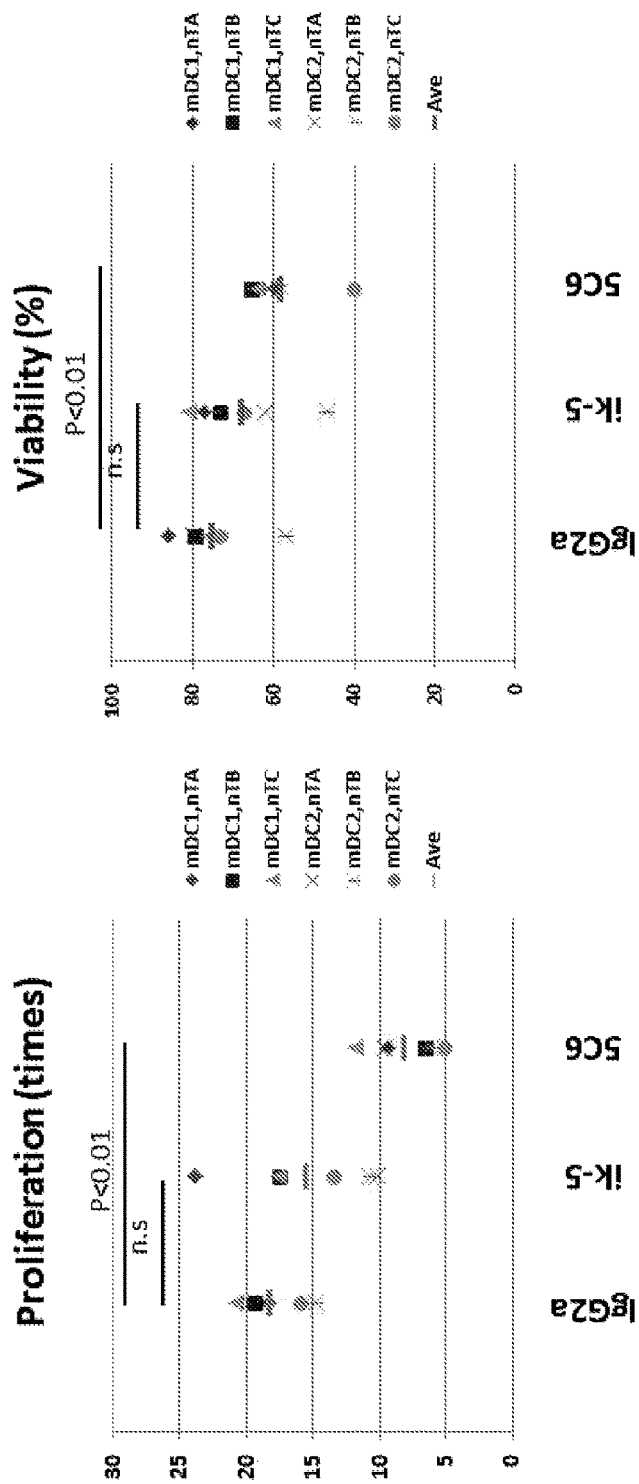
FIG. 4 depicts the results of an assay in which Dendritic cells and T cells were cocultured in the presence of 5C6 (AB104_105.5C6.3F9) anti-OX40L mAb, ik-5 anti-OX40L mAb, or control antibody (IgG2a) according to methods described in Example 1. Cells were harvested, and the proliferation and viability of the cells was determined.
Figure 5:
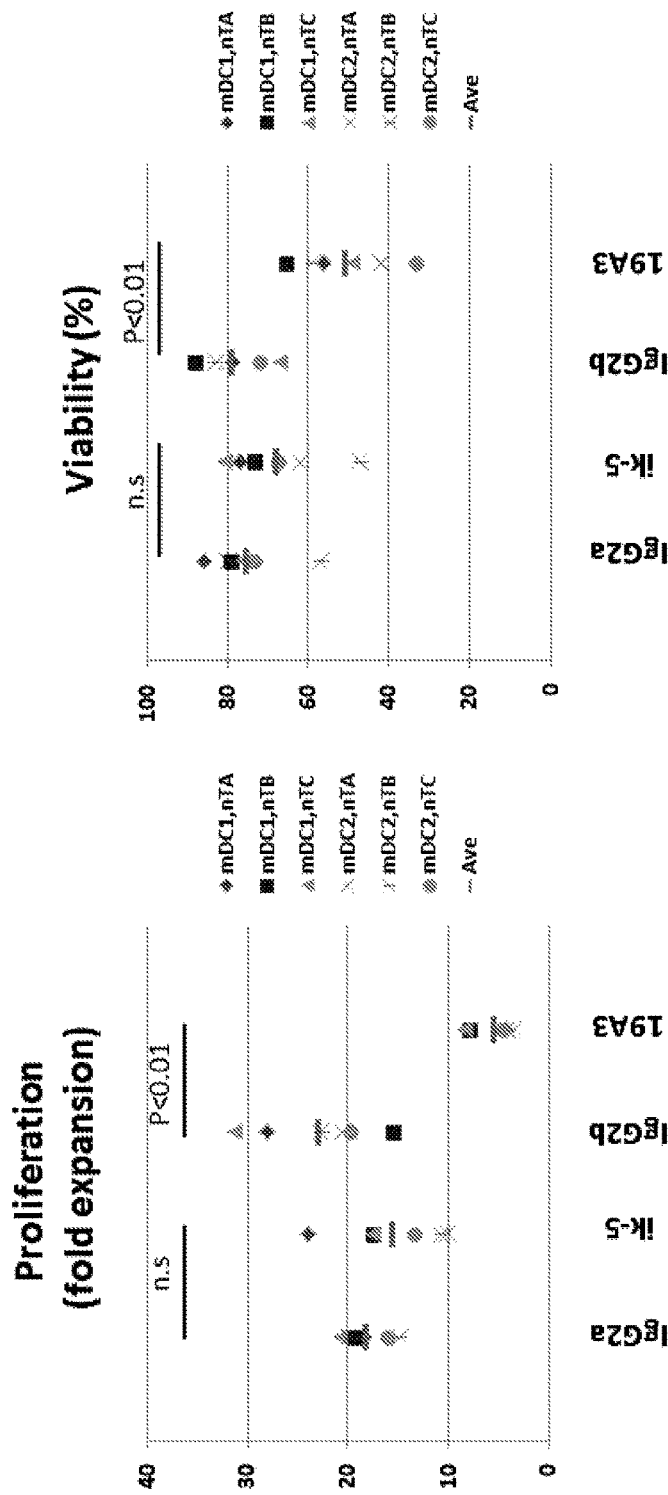
FIG. 5 depicts the results of an assay in which Dendritic cells and T cells were cocultured in the presence of 19A3 (AB104_105.19A3.2C4) anti-OX40L mAb, ik-5 anti-OX40L mAb, or control antibodies (IgG2a and IgG2b) according to methods described in Example 1. Cells were harvested, and the proliferation and viability of the cells was determined.
Figure 6:
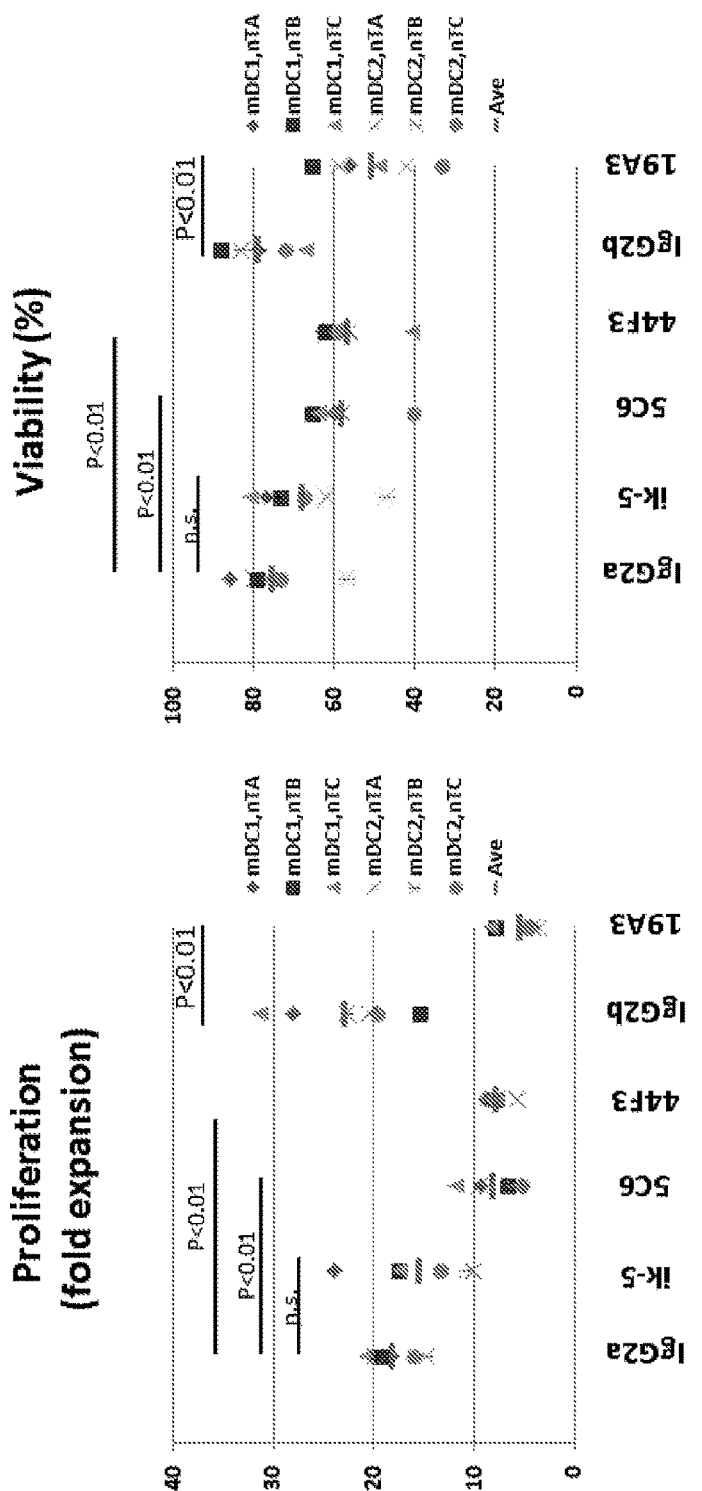
FIG. 6 depicts the results of an assay in which Dendritic cells and T cells were cocultured in the presence of 5C6 (AB104_105.5C6.3F9) anti-OX40L mAb, 44F3 (AB104_105.44F3.2F7) anti-OX40L mAb, 19A3 (AB104_105.19A3.2C4) anti-OX40L mAb, ik-5 anti-OX40L mAb, or control antibodies (IgG2a and IgG2b) according to methods described in Example 1. Cells were harvested, and the proliferation and viability of the cells was determined.
Figure 7:
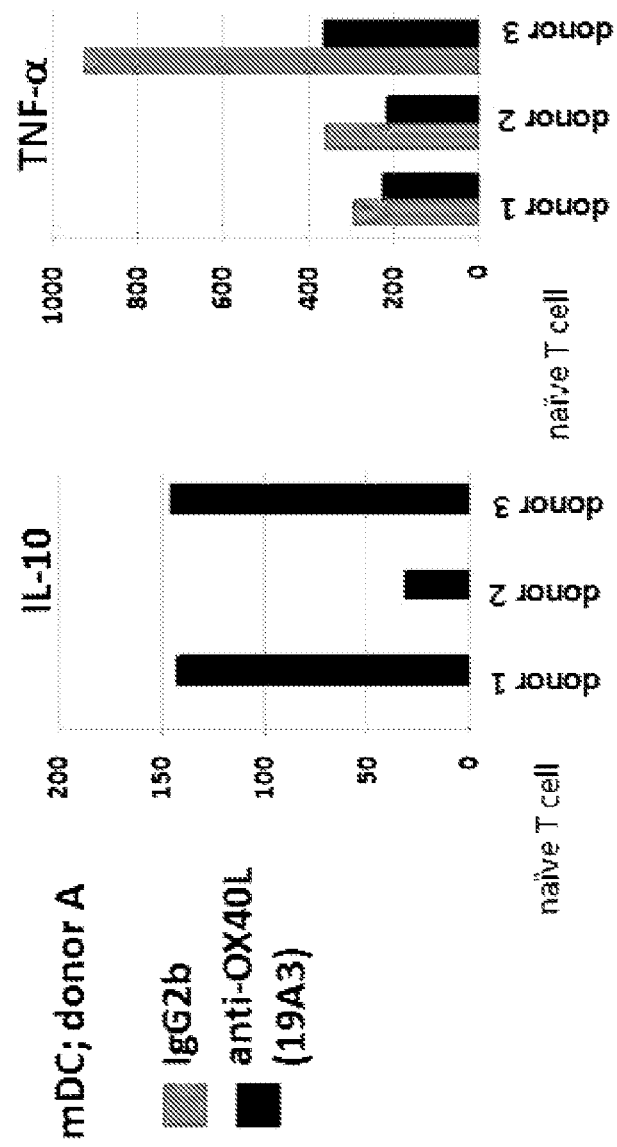
FIG. 7 depicts the results of an assay in which Dendritic cells and T cells were cocultured in the presence of 19A3 (AB104_105.19A3.2C4) or control antibody (Mouse IgG2b) according to methods described in Example 1. The production of IL-10 and TNF-α were measured by ELISA.
Figure 8:
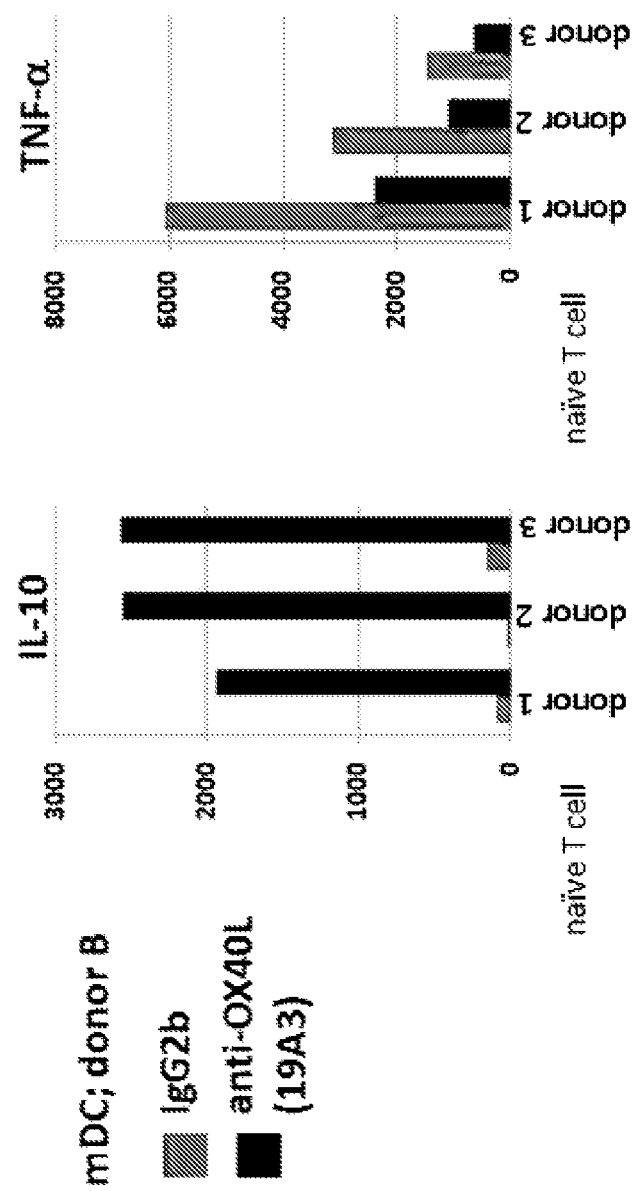
FIG. 8 shows a repeat of the experiment described in FIG. 7.
Figure 9:
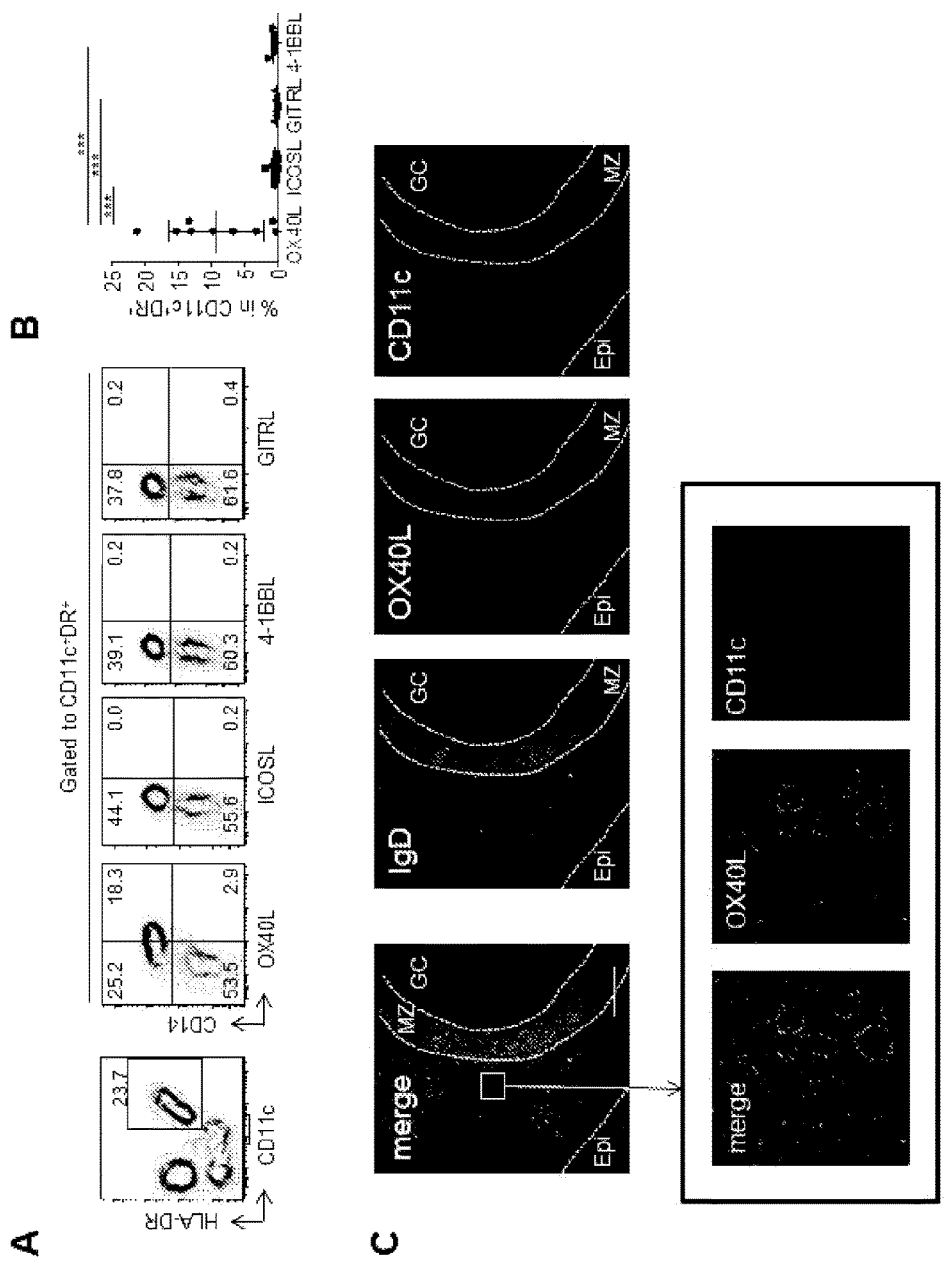
FIG. 9A-9C shows that increased OX40L expression by myeloid APCs in inflammatory tonsils. (A) Expression of OX40L, ICOSL, 4-1BBL and GITRL on myeloid CD11c+ HLA-DR+ APCs from pediatric tonsils. A representative result out of 9 independent experiments. (B) Frequency of OX40L+, ICOSL+, GITRL+, and 4-1BBL+ cells within tonsillar myeloid APCs. Mean±s.d., n=9. One way ANOVA. *** p<0.001. (C) OX40L+CD11c+ APCs in inflammatory tonsils. GC: germinal center; MZ: mantle zone; Epi: Epithelial layers. The scale bars on the top and the bottom panels shows 100 μm and 10 μm, respectively.

Previous studies in mouse models demonstrated the importance of ICOS ligand (ICOSL) expressed by DCs for the differentiation of Tfh cells (Choi et al., 2011). Applicants analyzed whether myeloid APCs (CD11c+HLA-DR+) express ICOSL in pediatric tonsils, which are enriched with mature Tfh cells along with GCs (Bentebibel et al., 2011). Applicants found that myeloid APCs in inflamed tonsils barely expressed ICOSL (FIG. 9A, 9B). Instead myeloid APCs, in particular CD14+ cells, expressed the co-stimulatory molecule OX40L (9.3±7.1% of CD11c+HLA-DR+ cells, Mean±s.d., n=9. FIG. 9A). Other TNF ligand family molecules such as GITRL and 4-1BBL were undetectable or expressed only at low levels (FIG. 9 A, B). However, OX40L expression by myeloid APCs was nearly absent in spleen (0.3±0.5% of CD11c+HLA-DR+ cells, Mean±s.d., n=4), where Tfh and GC responses are much less evident than in pediatric tonsils (Bentebibel et al., 2013). Thus, OX40L+ myeloid APCs are not present in all the secondary lymphoid organs, and appear to be restricted to those with inflammation.

To determine their localization, tonsil tissues were stained with anti-OX40L and anti-CD11c and analyzed by immunofluorescence microscopy. Applicants found that OX40L was abundantly expressed in tonsils, in particular subepithelial area, T cell zones, and mantle zones; but less in GCs (FIG. 9C). OX40L$^+$ CD11c$^+$ myeloid APCs were mainly found in the T cell zone (FIG. 9C). It is notable that OX40L was also expressed by CD11c$^-$ cells. This is consistent with the fact that OX40L can be expressed by a broad range of immune cells including B cells, vascular endothelial cells, mast cells, activated NK cells, and activated Th cells (Croft, 2010). These observation suggests that inflammatory environment in tonsils induces upregulation of OX40L expression on different types of cells by unknown mechanisms.

Myeloid APCs from Active Adult and Pediatric SLE Patients Express OX40L—

Figure 10:
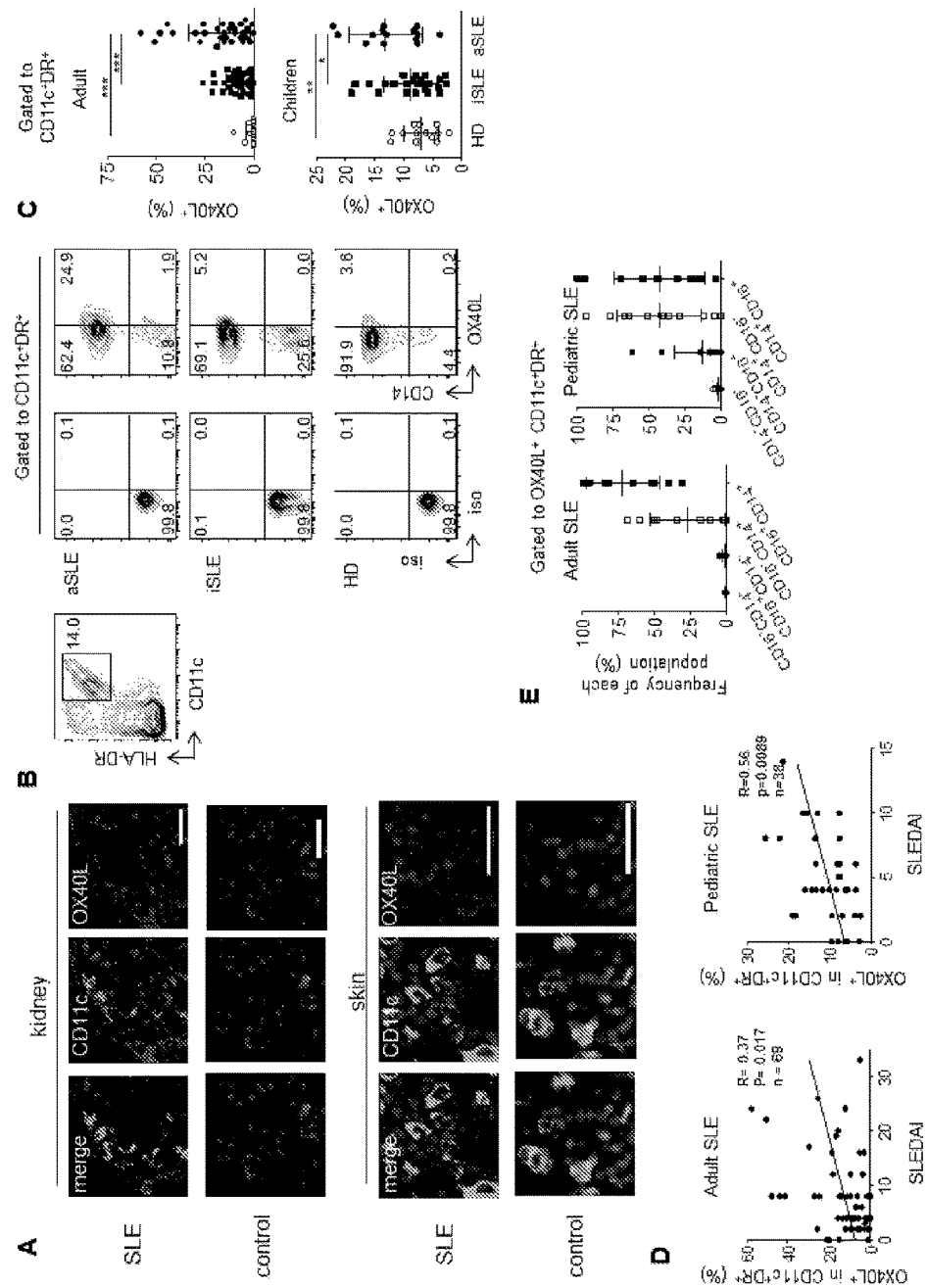
FIG. 10A-10E shows that OX40L expression by myeloid APCs from SLE patients. (A) OX40L+ myeloid APCs in skin and kidney biopsies from adult SLE patients and subjects without autoimmune diseases. A representative result of 5 skin and 3 kidney biopsy samples from SLE patients and 5 skin and 2 kidney biopsy samples from controls. Scale bar=100 μm. (B) Representative flow data on OX40L expression by blood myeloid CD11c+HLA-DR+ APCs from the three groups: healthy donors (HD), inactive (iSLE) and active (aSLE) SLE patients. (C) Frequency of OX40L+ cells within blood myeloid APCs in the three groups in adult and pediatric cohorts. Top: the adult cohort; 16 HD, 38 iSLE, and 31 aSLE samples. Bottom: the children cohort; 14 HD, 20 iSLE, and 14 aSLE samples. One-way ANOVA. * p<0.05,  p<0.01, * p<0.001. (D) Correlation between the percentage of OX40L+ cells within CD11c+ HLA-DR+ myeloid APCs (adults: n=69 and children: n=38) and disease activity assessed by the SLEDAI. Statistical analysis was performed with the Spearman test. (E) Composition of blood OX40L+ myeloid APCs by different subsets (CD14+CD16−, CD14+CD16+, CD14−CD16−, CD14−CD16+) in adult (n=28) and pediatric (n=34) SLE patients. Mean±s.d.

Given prominent expression of OX40L in inflamed tonsils, Applicants wondered whether OX40L was also expressed in inflammatory tissues from SLE patients. Applicants found that OX40L was abundantly expressed by cells including CD11c$^+$ myeloid APCs in inflammatory kidney tissues from active adult SLE patients with nephritis, but absent in tissues from subjects without autoimmune diseases (FIG. 10A). OX40L$^+$ myeloid APCs were also found in skin biopsy samples from SLE patients, but not from controls (FIG. 10A). Similar to tonsils, OX40L$^+$ CD11c$^-$ cells were also present in both tissues from SLE patients.

Figure 12:
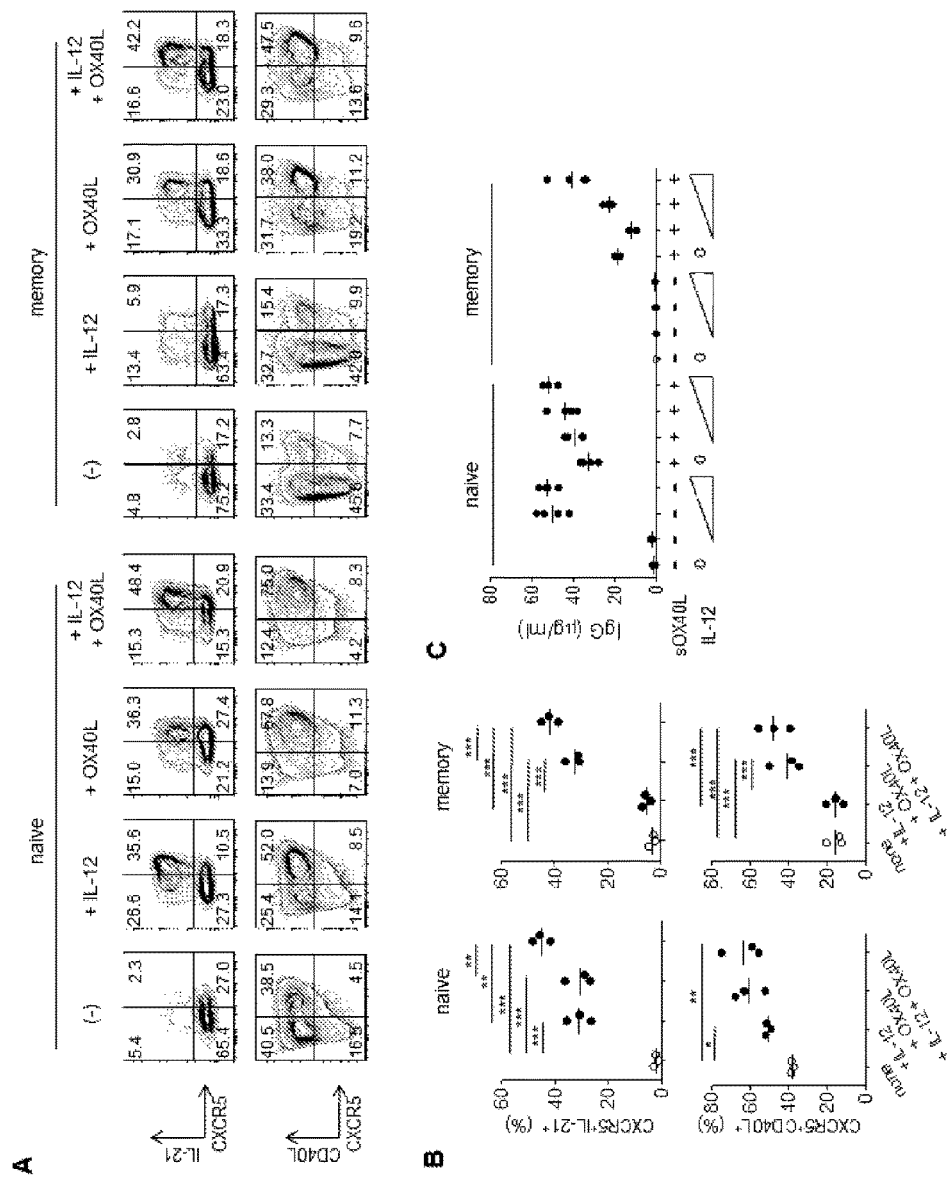
FIG. 12A-12C shows that OX40L stimulation promotes the differentiation of naïve and memory T cells into Tfh-like cells. (A) Expression of CXCR5, IL-21 and CD40L by naïve and memory Th cells activated for 4 d with anti-CD3 and anti-CD28 in the presence or absence of sOX40L and/or IL-12. Gated to FSCʰⁱSSCʰⁱ activated cells. A representative result out of 3 independent experiments is shown. (B) Frequency of CXCR5+IL-21+ and CXCR5+CD40L+ cells developed in naïve or memory Th cells after activation with anti-CD3 and anti-CD28 in the presence or absence of sOX40L and/or IL-12. One-way ANOVA. * p<0.05,  p<0.01, * p<0.001, n=3. (C) Naïve or memory Th cells were activated for 4 d with anti-CD3 and anti-CD28 in the presence of sOX40L and/or IL-12, and then cultured with autologous memory B cells. IgG concentrations in the supernatant of each well are shown. A representative result out of 2 independent experiments is shown.

Applicants next analyzed whether peripheral myeloid APCs in patients with SLE also express OX40L. OX40L expression was significantly increased on the surface of blood myeloid APCs from adult and pediatric patients with active SLE compared to healthy subjects, inactive SLE patients, and other autoimmune disease patients (FIG. 12B, and FIG. 15). Similar to tonsillar myeloid APCs (FIG. 9A, 9B), the expression of ICOSL, GITRL, or 4-1BBL on blood myeloid APCs was not observed (FIG. 16). The percentage of OX40L$^+$ cells in blood was significantly higher in active patients (assessed by the SLE Disease Activity Index (SLE-DAI)) than in inactive patients, both in adult and pediatric SLE (FIG. 10C). Furthermore, the frequency of OX40L$^+$ cells within myeloid APCs correlated with disease activity as assessed by the SLEDAI in both adult and pediatric SLE (FIG. 10D). OX40L was mainly expressed by CD14$^+$CD16$^+$ and CD14$^+$CD16$^-$ monocytes (FIG. 10E, and FIG. 17). In a longitudinal follow-up of 11 flaring and previously untreated adult SLE patients, the percentage of OX40L$^+$ myeloid APC substantially decreased after treatment along with the decrease in disease activity (FIG. 18, $P<0.01$, n=1).

Taken together, these results show that OX40L is expressed on blood and tissue-infiltrating myeloid APCs in active SLE patients.

OX40 Signals Promote the Expression of Tfh Genes in Naïve and Memory T Cells—

Figure 11:
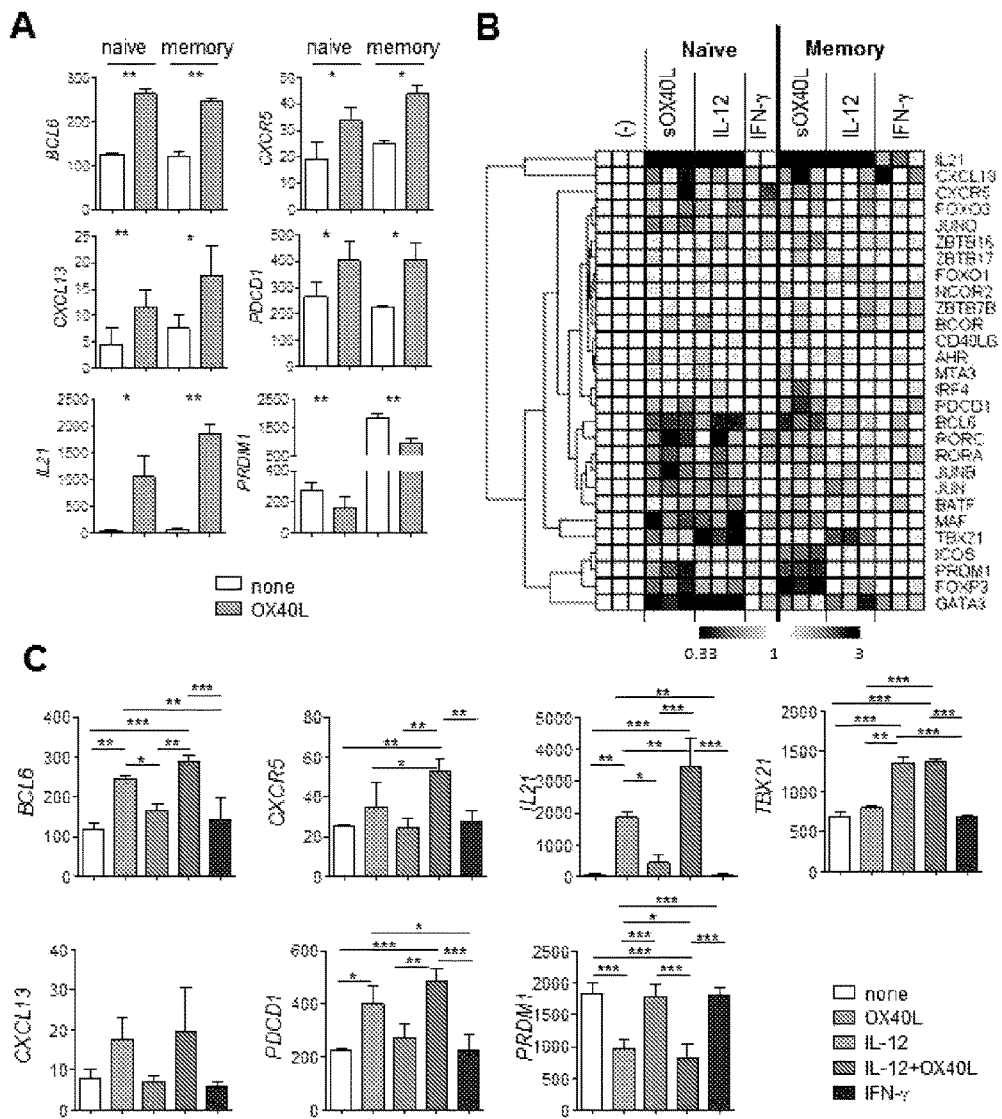
FIG. 11A-11C shows that OX40 signals induce upregulation of Tfh genes. (A) Tfh gene expression by naïve and memory Th cells (from three donors) activated with anti-CD3 and anti-CD28 in the presence or absence of sOX40L for 48 h. Transcript counts in the cultured Th cells are shown after normalization. Mean±s.d, n=3. Paired t-test. * p<0.05, ** p<0.01. (B) Tfh gene expression profiles by naïve and memory Th cells activated with anti-CD3 and anti-CD28 in the presence of indicated reagents for 48 h. Transcript counts in Th cells cultured in the presence of the indicated reagents were normalized to those in control Th cells in each donor. (C) Transcript counts in memory Th cells activated with anti-CD3 and anti-CD28 in the presence of indicated reagents. The bars in each bar graph represent, from left to right, "none," "OX40L," "IL-2," "IL-2+OX40L," and "IFN-γ." Mean±s.d., n=3. One-way ANOVA. * P<0.05,  P<0.01, * P<0.001.

The presence of OX40L$^+$ myeloid APCs in blood and inflamed tissues suggests that OX40L expression is globally increased on myeloid APCs in active SLE patients. In particular, inflamed tissues in SLE patients appear to create an OX40L-rich environment where Th cells receive OX40 signals together with T cell receptor signals (FIG. 10A). While providing signals important for T cell proliferation and survival, OX40 signals also regulate Th differentiation in collaboration with other factors derived from APCs, microenvironment, and Th cells themselves (Croft, 2010). Applicants hypothesized that OX40 signals might display an intrinsic property to promote the differentiation of human Th cells towards the Tfh lineage. To address this hypothesis, applicants applied an APC-free system to avoid the contribution of factors from APCs and microenvironment, and cultured naïve and memory Th cells with anti-CD3 and anti-CD28 in the presence of agonistic soluble OX40L (sOX40L). To minimize the influence of T cell-intrinsic factors, applicants analyzed the gene expression profiles at 48 h of culture by NanoString. For the assessment of the impact of OX40 signals on gene expression patterns, the transcript abundance in Th cells stimulated in the presence of sOX40L was normalized to the values in Th cells stimulated in the absence of sOX40L. Applicants found that OX40 signaling upregulated multiple Tfh genes, including CXCR5, BCL6, IL21, CXCL13, and PDCD1 (encoding PD-1) in both naïve and memory Th cells (FIG. 11A). Furthermore, OX40L stimulation downregulated the expression of PRDM1 (encoding Blimp-1), the transcription repressor that inhibits Tfh generation (Crotty, 2011).

Previously applicants and others show that IL-12 induces activated human naïve Th cells to express multiple Tfh molecules including IL-21, ICOS, CXCR5, and Bcl-6 at higher levels than other cytokines (Ma et al., 2009; Schmitt et al., 2013; Schmitt et al., 2009). Subjects deficient of IL-12 receptor β1 (IL-12R β1) chain display reduced Tfh and GC responses (in particular children), providing in vivo evidence that signals via IL-12 receptor is essential for the generation of Tfh cell differentiation in humans (Schmitt et al., 2013). Thus, applicants compared the expression of Tfh genes between OX40- and IL-12-stimulated Th cells. Surprisingly, OX40 signals induced naïve Th cells to express Tfh genes at equivalent levels with IL-12 signals (FIG. 19). Furthermore, overall expression patterns of Tfh genes were largely similar between OX40- and IL-12-stimulated naïve Th cells (FIG. 11B, left). While mouse studies suggest the positive role of IFN-γ for the generation of Tfh cells (Lee et al., 2012), the upregulation of Tfh molecules in these cells was not due to IFN-γ secreted in the cultures, as IFN-γ-stimulated naïve Th cells did not show the similar gene patterns (FIG. 19B, left). The combination of the two signals further increased the expression of IL21, but not other Tfh molecules.

In contrast to the observation with naïve Th cells, OX40 signals were more potent than IL-12 signals at inducing memory Th cells to modulate the expression of global Tfh genes (FIG. 11B, right) and at promoting the upregulation of Tfh genes (BCL6, CXCR5, IL-21, CXCL13, and PDCD1), and the downregulation of PRDM1 gene (FIG. 11C). It was notable that OX40 signals differentially modulated the expression of MAF and BATF, genes associated with Tfh development and functions (Crotty, 2011), between naïve and memory Th cells. OX40 signals induced upregulation of the two genes in naïve Th cells, but downregulation in memory Th cells (FIG. 11B). Nonetheless, IL-12 signals cooperated with OX40 signals to increase the expression of IL21 by memory Th cells (FIG. 11C).

OX40 Signals Promote the Generation of Functional Helpers—

To analyze the expression of Tfh molecules at protein levels, naïve and memory Th cells were activated by anti-CD3 and anti-CD28 in the presence or absence of sOX40L for three days, and the phenotype was analyzed by flow cytometry. Consistent with transcriptional data (FIG. 11A, 11B), OX40 signals promoted both naïve and memory Th cells to express Tfh molecules including CXCR5, CD40L, and IL-21, and increased the generation of CXCR5$^+$ cells co-expressing IL-21, CD40L and ICOS (FIGS. 12A and 12B; FIG. 20). Of note, in addition to IL-21, OX40 signals induced the expression of IL-2 and TNF-α, but not IFN-γ or IL-4 (FIG. 21). Furthermore, OX40L stimulation induced naïve Th cells to downregulate the expression of CCR7 on CXCR5$^+$ cells (FIG. 20), and increased the generation of CXCR5+CCR7$^-$ cells, a chemokine receptor expression profile required for homing to B cell follicles (Haynes et al., 2007). Strikingly, OX40 signals induced memory Th cells to express Tfh molecules including CXCR5, CD40L, and IL-21 more efficiently than IL-12 signals (FIG. 12B). Applicants noticed that OX40 signals decreased the expression of ICOS on memory Th cells compared to the control culture (FIG. 20), which was consistent with the transcriptional data (FIG. 11B). However, ICOS expression levels remained high, and more than 80% of CXCR5$^+$ cells stimulated with OX40 signals expressed ICOS.

Applicants wondered whether OX40 signals are sufficient to induce Th cells to become functional helpers. To this end, stimulated Th cells were co-cultured with autologous B cells and the produced IgG were measured at day 14. OX40 signals were sufficient to induce both naïve and memory Th cells to become B cell helpers (FIG. 12C). Notably, OX40 signals were more efficient than IL-12 signals to induce memory Th cells to become helpers (FIG. 12C). These results show that OX40L stimulation promotes naïve and memory Th cells to differentiate into Tfh-like cells.

Collectively, these results show that OX40 signals display an intrinsic property to induce human naïve and memory Th cells to express multiple Tfh molecules and to become functional B cell helpers.

Myeloid APCs from SLE Patients Promote the Generation of IL-21$^+$ Th Cells in an OX40L Dependent Manner—

Figure 13:
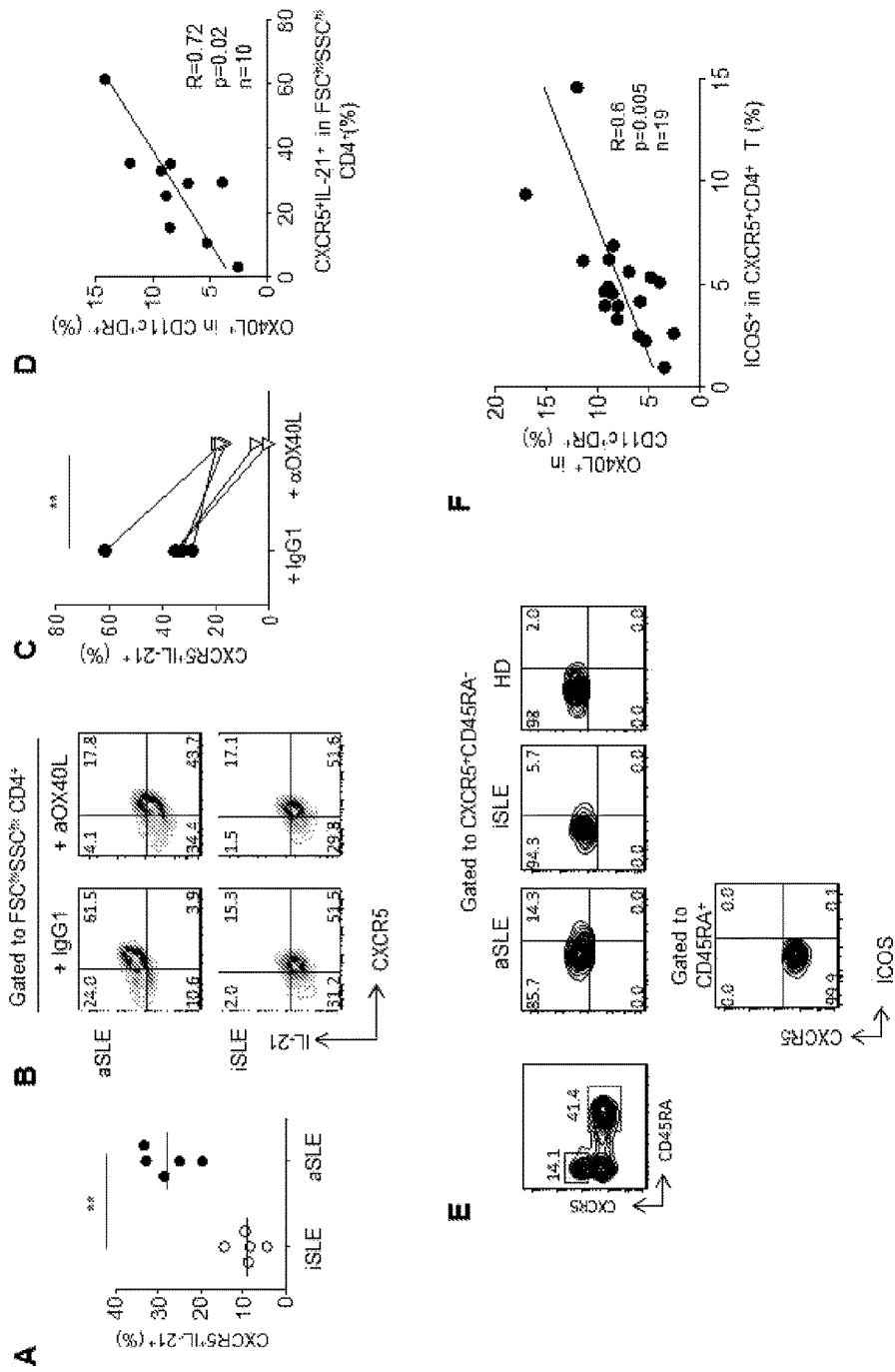
FIG. 13A-13F shows that blood CD14+ APCs in human SLE promote the generation of Tfh-like cells via OX40L. (A) Frequency of CXCR5+IL-21+ cells (among FSCʰⁱSSCʰⁱ activated cells) developed in naïve Th cells after culture for 7 d with allogeneic CD14+ APCs from inactive (iSLE, n=5) and active (aSLE, n=5) SLE patients. Mann-Whitney U-test.  p<0.01. (B) Expression of CXCR5 and IL-21 by naïve Th cells cultured with allogeneic SLE CD14+ APCs in the presence of an OX40L neutralizing mAb or a control IgG. A representative result out of 5 experiments is shown. (C) Decreased generation of CXCR5+IL-21+ cells (among FSCʰⁱSSCʰⁱ activated cells) by anti-OX40L. Results with APCs from active SLE patients are shown. Paired t-test.

These data suggest that OX40 signals contribute to the generation of aberrant Tfh response in SLE. Thus, applicants examined whether blood OX40L$^+$ myeloid APCs from active SLE patients induce Th cells to express Tfh molecules. Applicants used total CD14$^+$ monocytes for the experiments as isolation of OX40L$^+$ monocytes was not feasible. CD14$^+$ monocytes were isolated from active and inactive adult SLE patients and cultured with allogeneic naïve Th cells. Applicants found that CD14$^+$ monocytes from active patients induced naïve Th cells to become CXCR5$^+$IL-21$^+$ T cells more efficiently than those from inactive SLE patients (FIG. 13A). The generation of CXCR5$^+$IL-21$^+$ cells was largely dependent on OX40L, because blocking the OX40-OX40L interactions with a OX40L-neutralizing mAb strongly inhibited it (FIGS. 13B and 13C). Furthermore, the number of the generated CXCR5$^+$IL-21$^+$ cells positively correlated with the frequency of OX40L$^+$ monocytes in the cultures (FIG. 13D).

Previous studies showed that active SLE patients display an increased frequency of blood Tfh cells with active phenotype (ICOS$^+$CXCR5$^+$) (He et al., 2013; Simpson et al., 2010). Applicants were able to confirm this observation in the cohort (FIG. 13E). Applicants further found that the frequency of ICOS+ cells within blood Tfh cells positively correlated with the frequency of OX40L+ cells within blood myeloid APCs (FIG. 13F). The frequency of OX40L+ APCs also positively correlated with the frequency of blood Tfh cells (CXCR5+ in total Th cells) (FIG. 22), but showed no correlation with the frequency of blood CXCR5− Th1 (CXCR3+CCR6−), Th2 (CXCR3−CCR6−) Th17 (CXCR3−CCR6+) cells (Morita et al., 2011) (FIG. 23). Collectively, these results suggest that OX40L− expressing myeloid APCs from SLE patients promote the development and/or the activation of Tfh cells.

Figure 14:
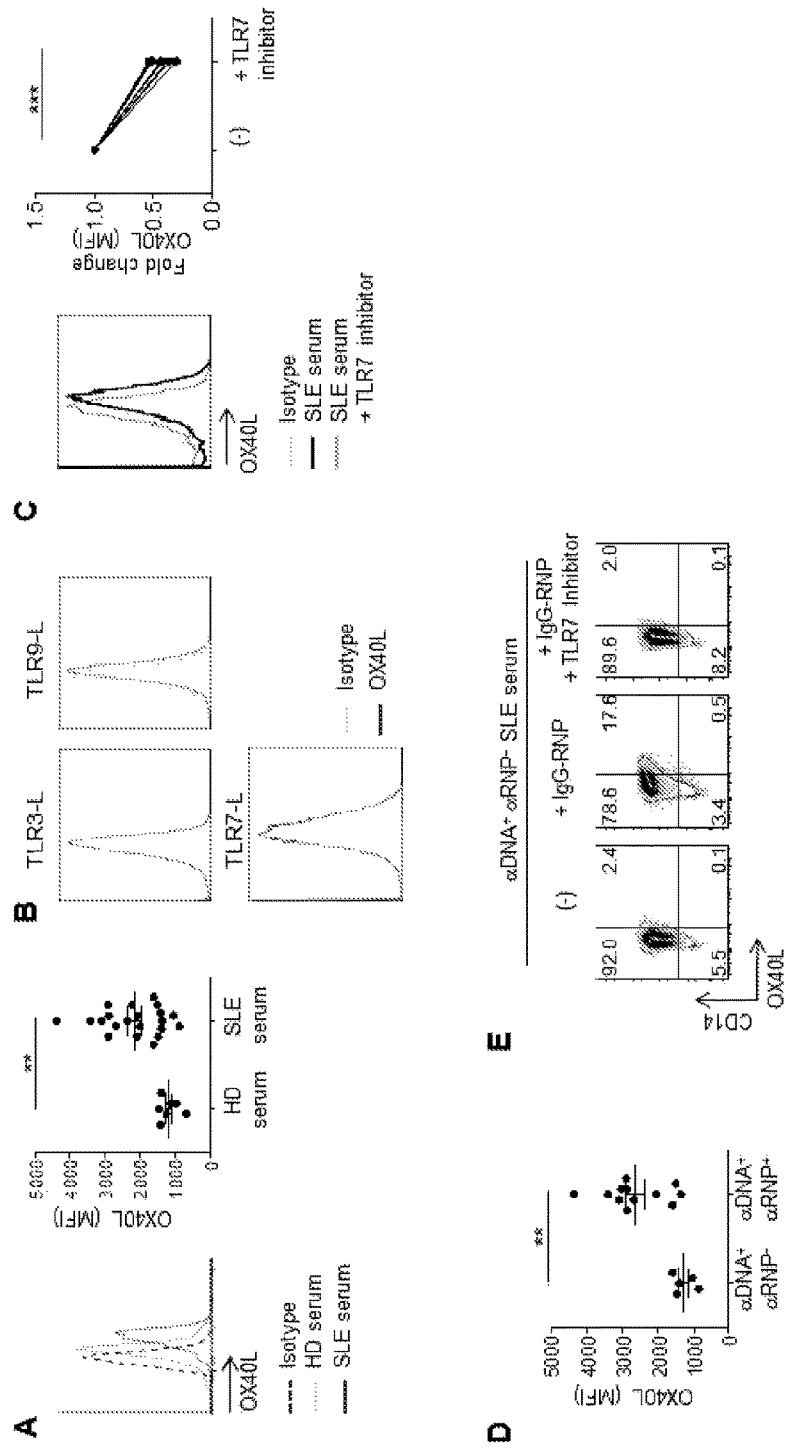

RNP/anti-RNP ICs promote OX40L expression through TLR7 activation. Applicants wondered which mechanism is involved in OX40L expression by myeloid APCs in active SLE patients. Applicants previously demonstrated that SLE sera induce monocytes to acquire the properties of DCs (Blanco et al., 2001). Therefore, applicants hypothesized that SLE sera might contain components that induce OX40L expression by myeloid APCs. Accordingly, applicants found that SLE sera, but not control sera, induced OX40L expression on normal monocytes at variable levels (FIG. 14A). Applicants suspected the involvement of immune complexes (ICs) containing self nucleic acid, because activation of APCs through endosomal nucleic acid sensors play a key role in SLE pathogenesis (Barrat and Coffman, 2008). Indeed, stimulation with agonist of TLR7, but not TLR9 and 3, induced normal monocytes to express OX40L (FIG. 14B). To test whether TLR7 was directly implicated in OX40L upregulation by SLE sera, applicants exposed normal monocytes to SLE sera in the presence of a specific TLR7 inhibitor IRS-661 (Barrat et al., 2005) or RNAse. Both TLR7 inhibitor and RNAse significantly reduced the ability of SLE sera to induce OX40L expression (FIG. 14C; FIG. 24), suggesting the major role by ICs containing RNA. In agreement with this hypothesis, applicants observed that the presence of anti-ribonucleoprotein (RNP), but not anti-DNA, antibodies in SLE sera was associated with the increased ability to promote OX40L expression on normal monocytes (FIG. 14D).

To validate whether RNP/anti-RNP ICs were directly involved in OX40L expression, monocytes were cultured with anti-RNP negative SLE sera, and purified IgG containing RNP/anti-RNP ICs were spiked into the cultures. Applicants found that the supplementation with RNP/anti-RNP ICs rendered anti-RNP negative SLE sera able to promote OX40L expression (FIG. 14E). This effect was dependent on TLR7, as addition of TLR7-specific inhibitor abrogated the upregulation of OX40L (FIG. 14E).

These data show that RNP/anti-RNP ICs promote OX40L expression through TLR7 activation in myeloid APCs in active SLE.

Autoreactive antibody production is a hallmark of a variety of autoimmune diseases including SLE. This study provides evidence that OX40L expressed by myeloid APCs contributes to lupus pathogenesis by promoting the generation of Tfh cells.

The expression of OX40L by myeloid APCs was increased in blood as well as in inflammatory tissues in active SLE patients. OX40L$^+$ myeloid APCs in blood of active SLE patients were largely confined to CD14$^+$CD16$^-$ and CD14$^+$CD16$^+$ monocyte populations. OX40L$^+$ myeloid APCs in pediatric tonsils were also largely limited to the CD14$^+$ population. Increased OX40L expression on blood monocyte populations was also reported in patients with sepsis (Karulf et al., 2010) and patients with chronic hepatitis C (Zhang et al., 2013). Interestingly, both disease conditions are known to be often associated with hyper gammaglobulinemia. These observations suggest that monocytes and macrophages upregulate OX40L in inflammatory environment, and contribute to antibody responses.

The pathogenic roles of ICs containing self nucleic acid are well established in SLE. The ICs activate plasmacytoid DCs via TLR9 and TLR7, and induce them to produce large amounts of type I interferons (Lovgren et al., 2006). Type I IFN stimulation induces neutrophils to upregulate TLR7, and renders them able to respond to RNP/anti-RNP ICs. Then neutrophils produce DNA-containing components that activate pDCs (Garcia-Romo et al., 2011; Lande et al., 2011). RNP/anti-RNP ICs also target the CD16$^+$CD14$^{dim}$ monocyte population, and induce these cells to produce cytokines that damage the endothelium, including TNF-α, IL-1, and CCL3 (Cros et al., 2010). While these mechanisms activate the innate immune system and cause inflammation, this study shows that RNP/anti-RNP ICs also activate the adaptive immune system. The inventors found that RNP/anti-RNP ICs contribute to OX40L expression by monocytes/macrophages via TLR7. Tfh responses increased by the RNP/anti-RNP IC-OX40L axis further accelerate the generation of autoantibodies including those against self nucleic acid. Therefore, the RNP/anti-RNP IC-OX40L axis appear to provide an amplification loop of the generation of autoantibodies in SLE.

The inventors showed that OX40 signals together with TCR and CD28 signals promote naïve and memory Th cells to express multiple Tfh molecules, including CXCR5, IL-21, and Bcl-6, while suppressing the expression of Blimp-1. The inventors also found that OX40 signals and IL-12 signals were almost equivalently efficient at inducing human naïve Th cells to express Tfh molecules. Furthermore, the two signals cooperate in the upregulation of IL-21 expression by Th cells. Remarkably, OX40 signals were more potent than IL-12 signals to induce memory Th cells to express Tfh molecules, and were sufficient to render them to become efficient B cell helpers. These results show that OX40 signals display intrinsic property to drive Th differentiation towards the Tfh lineage. It is presumable that interactions with OX40L-expressing APCs in inflammatory tissues in SLE render memory T cells to differentiate into Tfh cells and thereby potentially perpetuate the B cell autoimmune response in situ. Nonetheless, reduced Tfh and GC responses in subjects deficient of ICOS, CD40L (Bossaller et al., 2006), IL-12Rβ1 chain (Schmitt et al., 2013), and STAT3 (Ma et al., 2012) suggest that OX40 signals by themselves are not sufficient to compensate the lack of these signals. Furthermore, subjects deficient of OX40 show intact antibody responses in vivo despite less blood memory B cells (Byun et al., 2013), indicating that OX40 signals can be dispensable for generation of antibody responses. Therefore, the inventors surmise that excessive OX40 signals cause aberrant Tfh response and autoimmunity in humans. The positive correlation between the frequency of ICOS$^+$ blood Tfh cells and the frequency of OX40L$^+$ myeloid APCs in active SLE patients supports this hypothesis.

Early mouse studies showed that OX40L stimulation promotes mouse naïve Th cells to express CXCR5 (Flynn et al., 1998), and their migration into B cell follicles (Brocker et al., 1999; Fillatreau and Gray, 2003). Furthermore, an OX40L-transgenic mice model (T cell-specific overexpression) showed development an autoimmune-like disease characterized by interstitial pneumonia, colitis, and high levels of anti-nuclear antibodies (Murata et al., 2002). Recent studies show that the mutation of Roquin gene in sanroque mice causes upregulation of OX40 on Th cells, suggesting the positive role of OX40 signals for the generation of Tfh cells (Pratama et al., 2013; Vogel et al., 2013). On the other hand, at least two studies concluded that the absence of OX40 signals did not affect CXCR5 expression by Th cells, Tfh differentiation, GC development, or antibody generation (Akiba et al., 2005; Kopf et al., 1999). Furthermore, in vivo treatment with agonistic OX40 mAb inhibited Tfh cell generation in mice in an acute viral infection model (Boettler et al., 2013) and in a *listeria* infection model (Marriott et al., 2014. Boettler et al. showed that agonistic anti-OX40 mAb induced enhanced the expression of Blimp-1 by specific Th cells while suppressing the expression of Bcl-6 in vivo (Boettler et al., 2013), contrary to the inventors' observations with human Th cells in vitro. Given that OX40 signals regulate Th differentiation in collaboration with other factors derived from APCs, microenvironment, and Th cells themselves (Croft, 2010), it is possible that OX40 signals promote or suppress Tfh cell differentiation according to the microenvironment where Th cells interact with APCs. Another possibility is that OX40 signals differentially induce Tfh molecules between human and mouse Th cells.

The inventors' conclusion is also supported by the findings in GWAS in autoimmune diseases. TNFSF4 (encoding OX40L) polymorphism has been found to confer susceptibility to SLE (Cunninghame Graham et al., 2008; Delgado-Vega et al., 2009) and other autoimmune diseases, such as Sjögren syndrome, and rheumatoid arthritis (Kim et al., 2014; Nordmark et al., 2011). The TNFSF4 risk allele is also associated with renal disorder in Caucasian SLE patients (Sanchez et al., 2011). Furthermore, copy number variations and/or polymorphism at the TLR7 locus has been shown to associate with SLE susceptibility (Shen et al., 2010). This study provides a rationale that therapeutic modalities targeting the RNP-containing IC-OX40L-OX40 axis and TLR7 could impact the development of autoantibodies and therefore be beneficial for human SLE.

Example 3: In Vivo Efficacy of Anti-OX40L in the Suppression of GVHD

Allograft survival with no adverse effects is an ultimate goal in transplantation. Over the past several decades, a large array of immunosuppressive agents have been developed and used for patients who underwent transplantation surgery. However, such immunosuppressive drugs do not guarantee the prevention of alloreaction over time in patients who receive organs, tissues, and hematopoietic stem cell (HPSC) transplantation. As a consequence, patients succumb to graft-versus-host disease (GVHD) as well as serious side effects from life-long immunosuppression.

Therefore, the development of novel therapeutic strategies that prevent GVHD without diminishing host immunity to microbial pathogens is of particular importance. Anti-OX40L antibodies did not interfere with human chimerism.

Anti-OX40L antibodies did not interfere with human chimerism (FIG. 26A-B). It was then tested whether anti-OX40L antibody (clone 19A3, IgG2b) treatment could result in the suppression of GVHD in animal model. In xenogeneic GVHD mouse models, human T cells activated with human DCs are the major causes of diseases. Fifteen NOG mice were γ-irradiated one day before human PBMC (10 million cells, intravenously) transplantation. Animals were divided into three groups (five-six mice/group) and then treated with 200 μg of qan isotype control, 2 μg anti-OX40L (clone 19A3), or 200 μg anti-OX40L (clone 19A3) three times per week. FIG. 25 shows that all animals treated with 200 μg anti-OX40L were still alive at day 112 whereas all the animals treated with the isotype control had died (or had to be sacrificed due to adverse health reasons) by day 42. Two-thirds of the animals treated with 2 μg anti-OX40L had died by day 112, and one-third was still alive. These data indicate that anti-OX40L can suppress GVHD in vivo.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aagaard and Rossi, Adv. Drug Delivery Rev. 59:75-86, 2007.
Aguino-Jarguin, et al., Oligonucleotides. 18(3):213-24, 2008.
Akiba, et al., J Immunol 175:2340-2348, 2005.
Amon, et al., "Monoclonal Antibodies For Immunotargeting Of Drugs In Cancer Therapy", in Monoclonal Antibodies And Cancer Therapy, pp. 243-56, 1985.
Arbones, et al., Immunity. 1(4):247-260, 1994.
Babcook, et al., Proc. Natl. Acad. Sci. USA. 93:7843-7848, 1996.
Baldwin, et al., "Analysis, Results, And Future Prospective Of The Therapeutic Use Of Radiolabeted Antibody in Cancer Therapy", in Monoclonal Antibodies For Cancer Detection And Therapy, pp. 303-16, 1985.
Banchereau, et al., Annual review of immunology. 12:881-922, 1994.
Barrat & Coffman, Immunological reviews. 223:271-283, 2008.
Barrat, et al., The Journal of experimental medicine. 202:1131-1139, 2005.
Bentebibel, et al., PNAS USA. 108:E488-497, 2011.
Bentebibel, et al., Science Translational Medicine. 5:176ra132, 2013.
Blanco, et al., Cytokine Growth Factor Rev. 19:41-52, 2008.
Blanco, et al., Science. 294:1540-1543, 2001.
Boettler, et al., J Immunol. 191:5026-5035, 2013.
Bossaller, et al., J Immunol. 177:4927-4932, 2006.
Boumpas, et al., Arthritis and rheumatism. 48:719-727, 2003.
Brocker, et al., European journal of immunology. 29:1610-1616, 1999.
Bryant, et al., J Immunol. 179:8180-8190, 2007.
Bubier, et al., Proceedings of the National Academy of Sciences. 106(5):1518-23, 2009.
Byun, et al., The Journal of experimental medicine. 210:1743-1759, 2013.
Cech, Biotechnology. 13:323, 1995
Chang et al., PNAS. 100(20):11672-11677, 2003.
Chang, et al., J Immunol. 186:1849-1860, 2011.
Choi, et al., Immunity. 34:932-946, 2011.
Chtanova, et al., J Immunol. 173:68-78, 2004.
Conrad et al., Plant Mol. Biol. 38:101-109, 1998 Craft, Nat Rev Rheumatol 8:337-347, 2012.
Croft, Annual review of immunology 28:57-78, 2010.
Cros, et al., Immunity. 33:375-386, 2010.
Crotty, Annual review of immunology. 29:621-663, 2011.
Cunninghame Graham, et al., Nat Genet. 40:83-89, 2008.
de Fougerolles, et al., Nature Reviews Drug Discovery. 6:443-53, 2007.
Delgado-Vega, et al., Genes Immun. 10:248-253, 2009.
Dykxhoorn & Lieberman, Annu Rev. Biomed. Eng. 8:377-402, 2006.
Dykxhoorn et al., Gene Therapy 13:541-52, 2006.
Eck et al., in Goodman & Gilman's The Pharmacological Basis of Therapeutics, 9$^{th}$ Ed, McGray-Hill, New York, 5:77-101, 1996.
Edgington, Biotechnology. 10:256, 1992.
Eren et al., Mumma. 93:154-161, 1998.
Ferretti et al., PNAS. 83:599, 1986.
Fillatreau & Gray, The Journal of experimental medicine. 197:195-206, 2003.
Flynn, et al., The Journal of experimental medicine. 188:297-304, 1998.
Gallo et al., European J. of Immun. 30:534-540, 2000.
Garcia-Romo, et al., Science Translational Medicine. 3:73ra20, 2011.
Gardlik et al., Med. Sci. Monit. 11: RA110-121, 2005.
Gateva, et al., Nat Genet. 41:1228-1233, 2009.
Gray et al., J. Imm. Meth. 182:155-163, 1995.
Green & Jakobovits, J. Exp. Med. 188(3):483-495, 1998.
Green, J. of Immun. Methods 231:11-23, 1999.
Han, et al., Nat Genet. 41:1234-1237, 2009.
Hanes et al, Proc. Natl. Acad. Sci. USA. 95:14130-14135, 1998.
Haynes, et al., J Immunol. 179:5099-5108, 2007.
He, et al., Immunity. 39:770-781, 2013.
Hellstrom, et al., "Antibodies For Drug Delivery", in Controlled Drug Delivery (2nd Ed.), pp. 623-53, 1987.
Herber, et al., J Immunol. 178:3822-3830, 2007.
Herlyn et al., Science. 232:100, 1986.
Heywood et al., Nucleic Acids Res. 14:6771, 1986.
Hochberg, Arthritis and rheumatism. 40:1725, 1997.
Holliger and Hudson, Nature Biotech 23(9):1126-36, 2005.
Hollinger et al. (1993) Proc. Natl. Acad. Sci. USA 90:6444-6448, 1993.
International Consortium for Systemic Lupus Erythematosus, Nat Genet 40:204-210, 2008.
Izant et al., Cell. 36:1007, 1984.
Jakobovits et al., Proc. Natl. Acad. Sci. USA. 90(6):2551-2555, 1993.
Jakobovits, Advanced Drug Reviews. 31:33-42, 1998.
Jakobovits, Current Biology. 4(8):761-763, 1994.
Jakobovits, Current Opinion in Biotechnology. 6:561-566, 1995.
Jakobovits, Exp. Opin. Invest. Drugs. 7(4):607-614, 1998.
Jakobovits, Nature. 362(6417):255-258, 1993.
Jakobovits, Weir's Handbook of Experimental Immunology, The Integrated Immune System Vol. IV, 194.1-194.7, 1996.
Kabat et al., Sequences of Proteins of Immunological interest, 4th ed., Bethesda, Md., National Institutes of Health. 1987.
Kalled, et al., J Immunol. 160:2158-2165, 1998.
Karpovsky, et al., J. Exp. Med. 160:1686, 1984.
Karulf, et al., J Immunol. 185:4856-4862, 2010.
Kenny, et al, Bio. Technol. 13:787-790, 1995.
Kim, et al., Ann Rheum Dis. Doi: 10.1136/annrheumdis-2013-204749, 2014.
Kim, et al., Blood 104:1952-1960, 2004.
King, et al., Annual review of immunology. 26:741-766, 2008.
Klechevsky, et al., Immunity. 29:497-510, 2008.
Kopf, et al., Immunity. 11:699-708, 1999.
Koyama, Chem. Abstr. 120:217262t, 1994.
Krueger et al., Oligonucleotides. 17:237-250, 2007.
Lande, et al., Science Translational Medicine. 3:73ra19, 2011.
Lee, et al., Immunity. 37:880-892, 2012.
Liarski, et al., Science Translational Medicine. 6:230ra246, 2014.
Lin et al., J. Biol. Chem. 270:14255-14258, 1995.
Linterman, et al., The Journal of experimental medicine. 206:561-576, 2009.
Liu et al., Antimicrob. Agents & Chemotherapy. 50(10):3250-3259, 2006.
Liu et al., Cellular Microbiology. 9:120-130, 2007.
Liu et al., Proc. Natl. Acad. Sci. USA. 82:8648, 1985.
Lovgren, et al., Arthritis and rheumatism. 54:1917-1927, 2006.
Ma, et al., Blood. 119:3997-4008, 2012.
Ma, et al., Immunology and cell biology. 87:590-600, 2009.
MacLennan, Annual review of immunology. 12:117-139, 1994.
Marriott, et al., Eur J Immunol. Doi:10.1002/eji.201344211, 2014.
Meares, et al., Anal. Biochem. 142:68-78, 1984.
Mendez et al., Nature Genetics 15:146-156, 1997.
Mendez, et al, Genomics. 26:294-307, 1995.
Mizuno, et al., PNAS. 81:1966, 1984.
Moreau-Gaudry, et al., Blood 98:2664-2672, 2001.
Morelli, et al., J. Gen. Virol. 80:571-583, 1999.
Morita, et al., Immunity. 34:108-121, 2011.
Murata, et al., J Immunol. 169:4628-4636, 2002.
Murphy, et al., Lancet. 382:809-818, 2013.
Nabel et al., Science. 244:1342-1344, 1989.
Nguyen et al., Microbiol. Immunol. 41:901-907, 1977.

Nielsen et al., Science. 254:1497, 1991.
Nordmark, et al., Genes Immun. 12:100-109, 2011.
Odegard, et al., The Journal of experimental medicine. 205:2873-2886, 2008.
O'Keefe, Proc. Nat. Acad. Sci. USA 106(15):6099-6104, 2009.
Padlan et al., Mol. Immunol. 28(4-5):489-498, 1991.
Powell et al., Biotechnol. 8:333-337, 1990.
Pratama, et al., Immunity. 38:669-680, 2013.
Price, "Production and Characterization of Synthetic Peptide-Derived Antibodies," in Monoclonal antibodies: Production, engineering and clinical application, pages 60-84, 1995.
Prochiantz, Current Opinion in Neurobiology. 6:629-634, 1996.
Przybylska et al., J. Gene Med. 6:85-92, 2004.
Quadri et al., Nucl. Med. Biol. 20:559-570, 1993.
Rao et al., PNAS. 102:11993-11998, 2005.
Rodwell et al., PNAS USA. 83:2632-2636, 1986.
Romano et al., Stem Cells. 18:19-39, 2000.
Russel et al., Infection and Immunity. 2000:1820-1826, 2000.
Sanchez, et al., Ann Rheum Dis. 70:1752-1757, 2011.
Sandhu et al., Crit, Rev. Biotechnol. 16:95-118, 1996.
Schmitt, et al., Blood. 121:3375-3385, 2013.
Schmitt, et al., Immunity. 31:158-169, 2009.
Segura, et al., The Journal of experimental medicine. 209: 653-660, 2012.
Shen, et al., Proceedings of the National Academy of Sciences. 107:15838-15843, 2010.
Sherman-Gold, Genetic Engineering News. 17(14), 1997.
Shields, et al., J. Biol. Chem. 277:26733-26740, 2002.
Simpson, et al., Arthritis and rheumatism. 62:234-244, 2010.
Simpson, et al., The Journal of infectious diseases. 181:621-625, 2000.
Soumelis, et al., Nat Immunol. 3(7):673-80, 2002.
Spira et al, J. Immunol. Methods. 74:307, 1984.
Spolski & Leonard, Annual review of immunology 26, 57-79, 2008.
Steenbakkers et al., Molec. Biol. Reports 19:125-134, 1994.
Steplewski et al., Proc. Natl. Acad. Sci. USA 82:8653, 1985.
Stohl, et al., Arthritis and rheumatism 64:2328-2337, 2012.
Svahn et al., J. Gene Med. 6:S36-S44, 2004.
Thorpe et al., Immunol. Rev. 62:119-58, 1982.
Thorpe, "Antibody Carriers Of Cytotoxic Agents In Cancer Therapy: A Review", in Monoclonal Antibodies '84: Biological And Clinical Applications, pp. 475-506, 1985.
Tiller, et al., Immunity 26:205-213, 2007.
Toshiyuki et al., J. Biol. Chem. 280(10):9345-53, 2005.
Tsokos, The New England journal of medicine. 365:2110-2121, 2011.
Tsuda et al., Genomics. 42:413-421, 1997.
Umana et al., Nat. Biotech. 17:176-180, 1999.
Upeslacis et al., "Modification of Antibodies by Chemical Methods," in Monoclonal antibodies: principles and applications, pages 187-230, 1995.
Vinuesa & Cyster, Immunity. 35:671-680, 2011.
Vinuesa, et al., Nature. 435:452-458, 2005.
Vogel, Immunity. 38:655-668, 2013.
Wanes et al., Proc. Natl. Acad. Sci. USA, 94:4937-4942, 1997.
Wen et al, J. Immunol. 17:887-892, 1987.
Wilson, Clin. Exp. Immunol. 107(Suppl. 1):31-32, 1997.
Wivel et al., Hematol Oncol Clin North Am. 12(3):483-501, 1998.
Wolff et al., Human Mol. Genet. 1:363-369, 1992.
Wolff et al., Science. 247:465-1468, 1990
Xu, et al., Nature. 496:523-527, 2013.
Yang et al., J. of Leukocyte Biology. 66:401-410, 1999a.
Yang, Cancer Research. 59(6): 1236-1243, 1999b.
You et al., Chem. Biol. 4:961-968, 1997.
Yu et al., Int. J. Cancer. 56:244, 1994.
Zapata, et al., Protein Eng. 8(10):1057-1062, 1995.
Zhang, European journal of immunology. 43:1953-1962, 2013.
Zhu, et al., Science. 261:209-211, 1993.

What is claimed is:

1. A method for treating an autoimmune disease, inflammation, and/or inflammation associated with an autoimmune disease, wherein the disease or inflammation is due, at least in part, to pathogenic Tfh cell responses, in a subject in need thereof comprising administering to the subject a therapeutically effective amount of an OX40L inhibitor wherein the OX40L inhibitor comprises an OX40L antibody or OX40L antigen-binding fragment comprising one of:
   a) a heavy chain variable domain comprising the complementarity determining region (CDR) amino acid sequences of SEQ ID NO: 5, SEQ ID NO: 6, and SEQ ID NO: 7 and a light chain variable domain comprising the complementarity determining region (CDR) amino acid sequences of SEQ ID NO: 12, SEQ ID NO: 13, and SEQ ID NO: 14;
   b) a heavy chain variable domain comprising the complementarity determining region (CDR) amino acid sequences of SEQ ID NO: 19, SEQ ID NO: 20, and SEQ ID NO: 21 and a light chain variable domain comprising the complementarity determining region (CDR) amino acid sequences of SEQ ID NO: 26, SEQ ID NO: 27, and SEQ ID NO: 28; or
   c) a heavy chain variable domain comprising the complementarity determining region (CDR) amino acid sequences of SEQ ID NO: 33, SEQ ID NO: 34, and SEQ ID NO: 35 and a light chain variable domain comprising the complementarity determining region (CDR) amino acid sequences of SEQ ID NO: 40, SEQ ID NO: 41, and SEQ ID NO: 42.

2. The method of claim 1, wherein the disease or inflammation is allergic disease asthma, atopic dermatitis, experimental autoimmune encephalomyelitis, inflammatory bowel disease, contact hypersensitivity, asthmatic airway hyperreaction, autoimmune diabetes, atherosclerosis, systemic lupus erythematosus, rheumatoid arthritis, multiple sclerosis, ulcerative colitis, graft versus host disease, graft rejection, or polymyositis.

3. The method of claim 1, wherein the subject is a human.

4. The method of claim 1, wherein the anti-OX40L antibody is neutralizing.

5. The method of claim 1, wherein the antibody is a human antibody, humanized antibody, recombinant antibody, chimeric antibody, an antibody derivative, a veneered antibody, a diabody, a monoclonal antibody, or a polyclonal antibody.

6. The method of claim 5, wherein the antibody is a humanized antibody.

7. The method of claim 1, wherein the antibody or antigen binding fragment thereof comprises a modification.

8. The method of claim 1, wherein the OX40L inhibitor comprises an antibody selected from the group consisting of 5C6, 19A3, and 44F3, or a humanized or chimeric form thereof.

9. A method for treating systemic lupus erythematosus comprising administering to the subject a therapeutically effective amount of an OX40L inhibitor wherein the OX40L inhibitor comprises an OX40L antibody or OX40L antigen-binding fragment comprising one of:
   a) a heavy chain variable domain comprising the complementarity determining region (CDR) amino acid sequences of SEQ ID NO: 5, SEQ ID NO: 6, and SEQ ID NO: 7 and a light chain variable domain comprising the complementarity determining region (CDR) amino acid sequences of SEQ ID NO: 12, SEQ ID NO: 13, and SEQ ID NO: 14;
   b) a heavy chain variable domain comprising the complementarity determining region (CDR) amino acid sequences of SEQ ID NO: 19, SEQ ID NO: 20, and SEQ ID NO: 21 and a light chain variable domain comprising the complementarity determining region (CDR) amino acid sequences of SEQ ID NO: 26, SEQ ID NO: 27, and SEQ ID NO: 28; or
   c) a heavy chain variable domain comprising the complementarity determining region (CDR) amino acid sequences of SEQ ID NO: 33, SEQ ID NO: 34, and SEQ ID NO: 35 and a light chain variable domain comprising the complementarity determining region (CDR) amino acid sequences of SEQ ID NO: 40, SEQ ID NO: 41, and SEQ ID NO: 42.

10. The method of claim 9, wherein the subject is a human.

11. The method of claim 9, wherein the OX40L inhibitor comprises an antibody selected from the group consisting of 5C6, 19A3, and 44F3, or a humanized or chimeric form thereof.

12. A method for preventing, treating, or reducing the symptoms of graft versus host disease in a subject in need thereof comprising administering to the subject a therapeutically effective amount of an OX40L inhibitor wherein the OX40L inhibitor comprises an OX40L antibody or OX40L antigen-binding fragment comprising one of:
   a) a heavy chain variable domain comprising the complementarity determining region (CDR) amino acid sequences of SEQ ID NO: 5, SEQ ID NO: 6, and SEQ ID NO: 7 and a light chain variable domain comprising the complementarity determining region (CDR) amino acid sequences of SEQ ID NO: 12, SEQ ID NO: 13, and SEQ ID NO: 14;
   b) a heavy chain variable domain comprising the complementarity determining region (CDR) amino acid sequences of SEQ ID NO: 19, SEQ ID NO: 20, and SEQ ID NO: 21 and a light chain variable domain comprising the complementarity determining region (CDR) amino acid sequences of SEQ ID NO: 26, SEQ ID NO: 27, and SEQ ID NO: 28; or
   c) a heavy chain variable domain comprising the complementarity determining region (CDR) amino acid sequences of SEQ ID NO: 33, SEQ ID NO: 34, and SEQ ID NO: 35 and a light chain variable domain comprising the complementarity determining region (CDR) amino acid sequences of SEQ ID NO: 40, SEQ ID NO: 41, and SEQ ID NO: 42.

13. The method of claim 12, wherein the subject is one that will receive or has received transplanted tissues.

14. The method of claim 12, wherein the OX40L inhibitor comprises an antibody selected from the group consisting of 5C6, 19A3, and 44F3, or a humanized or chimeric form thereof.

15. The method of claim 12, wherein the subject is a human.

16. The method of claim 12, wherein the method is for treating or reducing the symptoms of graft versus host disease.

* * * * *

SEQUENCE LISTING

```
<160> NUMBER OF SEQ ID NOS: 42

<210> SEQ ID NO 1
<211> LENGTH: 1420
<212> TYPE: DNA
<213> ORGANISM: Mus musculus

<400> SEQUENCE: 1
atggaatgga gctggatctt tctcttcctc ctgtcaggaa ctgcaggtgt acactctgag      60
gtccagcttc agcagtctgg gcctgagctg gggcagcctg ggcttcagt gaagatatcc     120 tgcaaggctt ctggttactc attcactggt tacagcatgc actgggtgaa gcagagccat     180
aggaaaagcc ctgagtggat tggaaaaatt gatccttaca atggtgtgac tacctataat     240
cagaggttca cgggcaaggc cacattgact gtcgacacat cttccagcac agcctacatg     300
catctcaaca gcctgacatc tgaggactct gcaatctttt actgtgcgag agagggttt     360 gcttattggg gccaagggac tctggtctct gtctctgaag ccaaaacaac acccccatca     420
gtctatccac tggcccctgg gtgtgagat acaactggtt cctccgtgac tctgggatgc     480
ctggtcaagg gctacttccc tgagtcagtg actgtgactt ggaactctgg atccctgtcc     540
agcagtgtgc acacmttccc agctctcctg cagtctggac tctacactat gagcagctca     600
gtgactgtcc cctccagcac ctggccaagt cagaccgtca cctgcagcgt tgctcaccca     660
```

```
gccagcagca ccacggtgga caaaaaactt gagcccagcg ggcccatttc aacaatcaac      720
ccctgtcctc catgcaagga gtgtcacaaa tgcccagctc ctaacctcga gggtggacca      780
tccgtcttca tcttccctcc aaatatcaag gatgtactca tgatctccct gacacccaag      840
gtcacgtgtg tggtggtgga tgtgagcgag gatgacccag acgtccagat cagctggttt      900
gtgaacaacg tggaagtaca cacagctcag acacaaaccc atagagagga ttacaacagt      960
actatccggg tggtcagcac cctccccatc cagcaccagg actggatgag tggcaaggag     1020
ttcaaatgca aggtcaacaa caaagacctc ccatcaccca tcgagagaac catctcaaaa     1080
attaaagggc tagtcagagc tccacaagta tacatcttgc cgccaccagc agagcagttg     1140
tccaggaaag atgtcagtct cacttgcctg gtcgtgggct tcaaccctgg agacatcagt     1200
gtggagtgga ccagcaatgg gcatacagag gagaactaca aggacaccgc accagtcctg     1260
gactctgacg gttcttactt catatatagc aagctcaata tgaaaacaag caagtgggag     1320
aaaacagatt ccttctcatg caacgtgaga cacgagggtc tgaaaaatta ctacctgaag     1380
aagaccatct cccggtctcc gggtaaagct agctgaaaaa                           1420
```

<210> SEQ ID NO 2
<211> LENGTH: 471
<212> TYPE: PRT
<213> ORGANISM: Mus musculus

<400> SEQUENCE: 2

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Gly Gln
            20                  25                  30

Pro Gly Ala Ser Val Lys Ile Ser Cys Lys Ala Ser Gly Tyr Ser Phe
        35                  40                  45

Thr Gly Tyr Ser Met His Trp Val Lys Gln Ser His Arg Lys Ser Pro
    50                  55                  60

Glu Trp Ile Gly Lys Ile Asp Pro Tyr Asn Gly Val Thr Thr Tyr Asn
65                  70                  75                  80

Gln Arg Phe Thr Gly Lys Ala Thr Leu Thr Val Asp Thr Ser Ser Ser
                85                  90                  95

Thr Ala Tyr Met His Leu Asn Ser Leu Thr Ser Glu Asp Ser Ala Ile
            100                 105                 110

Phe Tyr Cys Ala Arg Glu Gly Phe Ala Tyr Trp Gly Gln Gly Thr Leu
        115                 120                 125

Val Ser Val Ser Glu Ala Lys Thr Thr Pro Pro Ser Val Tyr Pro Leu
    130                 135                 140

Ala Pro Gly Cys Gly Asp Thr Thr Gly Ser Ser Val Thr Leu Gly Cys
145                 150                 155                 160

Leu Val Lys Gly Tyr Phe Pro Glu Ser Val Thr Val Thr Trp Asn Ser
                165                 170                 175

Gly Ser Leu Ser Ser Ser Val His Thr Phe Pro Ala Leu Leu Gln Ser
            180                 185                 190

Gly Leu Tyr Thr Met Ser Ser Ser Val Thr Val Pro Ser Ser Thr Trp
        195                 200                 205

Pro Ser Gln Thr Val Thr Cys Ser Val Ala His Pro Ala Ser Ser Thr
    210                 215                 220

Thr Val Asp Lys Lys Leu Glu Pro Ser Gly Pro Ile Ser Thr Ile Asn
225                 230                 235                 240
```

```
Pro Cys Pro Pro Cys Lys Glu Cys His Lys Cys Pro Ala Pro Asn Leu
                245                 250                 255

Glu Gly Gly Pro Ser Val Phe Ile Phe Pro Pro Asn Ile Lys Asp Val
            260                 265                 270

Leu Met Ile Ser Leu Thr Pro Lys Val Thr Cys Val Val Val Asp Val
        275                 280                 285

Ser Glu Asp Asp Pro Asp Val Gln Ile Ser Trp Phe Val Asn Asn Val
290                 295                 300

Glu Val His Thr Ala Gln Thr Gln Thr His Arg Glu Asp Tyr Asn Ser
305                 310                 315                 320

Thr Ile Arg Val Val Ser Thr Leu Pro Ile Gln His Gln Asp Trp Met
                325                 330                 335

Ser Gly Lys Glu Phe Lys Cys Lys Val Asn Asn Lys Asp Leu Pro Ser
            340                 345                 350

Pro Ile Glu Arg Thr Ile Ser Lys Ile Lys Gly Leu Val Arg Ala Pro
        355                 360                 365

Gln Val Tyr Ile Leu Pro Pro Pro Ala Glu Gln Leu Ser Arg Lys Asp
370                 375                 380

Val Ser Leu Thr Cys Leu Val Val Gly Phe Asn Pro Gly Asp Ile Ser
385                 390                 395                 400

Val Glu Trp Thr Ser Asn Gly His Thr Glu Glu Asn Tyr Lys Asp Thr
                405                 410                 415

Ala Pro Val Leu Asp Ser Asp Gly Ser Tyr Phe Ile Tyr Ser Lys Leu
            420                 425                 430

Asn Met Lys Thr Ser Lys Trp Glu Lys Thr Asp Ser Phe Ser Cys Asn
        435                 440                 445

Val Arg His Glu Gly Leu Lys Asn Tyr Tyr Leu Lys Lys Thr Ile Ser
450                 455                 460

Arg Ser Pro Gly Lys Ala Ser
465                 470

<210> SEQ ID NO 3
<211> LENGTH: 19
<212> TYPE: PRT
<213> ORGANISM: Mus musculus

<400> SEQUENCE: 3

Met Glu Trp Ser Trp Ile Phe Leu Phe Leu Leu Ser Gly Thr Ala Gly
1               5                   10                  15

Val His Ser

<210> SEQ ID NO 4
<211> LENGTH: 116
<212> TYPE: PRT
<213> ORGANISM: Mus musculus

<400> SEQUENCE: 4

Glu Val Gln Leu Gln Gln Ser Gly Pro Glu Leu Gly Gln Pro Gly Ala
1               5                   10                  15

Ser Val Lys Ile Ser Cys Lys Ala Ser Gly Tyr Ser Phe Thr Gly Tyr
                20                  25                  30

Ser Met His Trp Val Lys Gln Ser His Arg Lys Ser Pro Glu Trp Ile
            35                  40                  45

Gly Lys Ile Asp Pro Tyr Asn Gly Val Thr Thr Tyr Asn Gln Arg Phe
        50                  55                  60
```

```
Thr Gly Lys Ala Thr Leu Thr Val Asp Thr Ser Ser Thr Ala Tyr
 65                  70                  75                  80

Met His Leu Asn Ser Leu Thr Ser Glu Asp Ser Ala Ile Phe Tyr Cys
                 85                  90                  95

Ala Arg Glu Gly Phe Ala Tyr Trp Gly Gln Gly Thr Leu Val Ser Val
            100                 105                 110

Ser Glu Ala Lys
        115

<210> SEQ ID NO 5
<211> LENGTH: 10
<212> TYPE: PRT
<213> ORGANISM: Mus musculus

<400> SEQUENCE: 5

Gly Tyr Ser Phe Thr Gly Tyr Ser Met His
1               5                   10

<210> SEQ ID NO 6
<211> LENGTH: 17
<212> TYPE: PRT
<213> ORGANISM: Mus musculus

<400> SEQUENCE: 6

Lys Ile Asp Pro Tyr Asn Gly Val Thr Thr Tyr Asn Gln Arg Phe Thr
1               5                   10                  15

Gly

<210> SEQ ID NO 7
<211> LENGTH: 5
<212> TYPE: PRT
<213> ORGANISM: Mus musculus

<400> SEQUENCE: 7

Glu Gly Phe Ala Tyr
1               5

<210> SEQ ID NO 8
<211> LENGTH: 712
<212> TYPE: DNA
<213> ORGANISM: Mus musculus

<400> SEQUENCE: 8
atgcattttc aagtgcagat tttcagcttc ctgctaatca gtgcctcagt cataatgtcc      60
agaggacaaa ttgttctcac ccagtctcca gcaatcatgt ctgcatctcc aggggagaag     120
gtcaccataa cctgcagtgc ctcctcaagt gtccgttata ttcactggtt ccagcagaag     180
ccaggcactt ctcccaaact cttgatttat agcacatccg acctggcttc tggagtccct     240
gctcgcttca gtggcggtgg atctgggacc tcttactctc tcacaatcag ccgaatggag     300
gctgaagatg ctgccactta ttactgccag caaaggactg gttacccgct cacgttcggt     360
gctgggacca agctggagct gaaacgggct gatgctgcac caactgtatc catcttccca     420
ccatccagtg agcagttaac atctggaggt gcctcagtcg tgtgcttctt gaacaacttc     480
taccccaaag acatcaatgt caagtggaag attgatggca gtgaacgaca aaatggcgtc     540
ctgaacagtt ggactgatca ggacagcaaa gacagcacct acagcatgag cagcaccctc     600
acgttgacca aggacgagta tgaacgacat aacagctata cctgtgaggc cactcacaag     660
gcatcaactt cacccatcgt caagagcttc aacaggaatg agtgttagaa aa              712
```

-continued

```
<210> SEQ ID NO 9
<211> LENGTH: 235
<212> TYPE: PRT
<213> ORGANISM: Mus musculus

<400> SEQUENCE: 9
```

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Arg Tyr Ile His Trp Phe Gln Gln Lys Pro Gly Thr Ser
    50                  55                  60

Pro Lys Leu Leu Ile Tyr Ser Thr Ser Asp Leu Ala Ser Gly Val Pro
65                  70                  75                  80

Ala Arg Phe Ser Gly Gly Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Thr Gly Tyr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Ala Ser Thr Ser
    210                 215                 220

Pro Ile Val Lys Ser Phe Asn Arg Asn Glu Cys
225                 230                 235

```
<210> SEQ ID NO 10
<211> LENGTH: 22
<212> TYPE: PRT
<213> ORGANISM: Mus musculus

<400> SEQUENCE: 10
```

Met His Phe Gln Val Gln Ile Phe Ser Phe Leu Leu Ile Ser Ala Ser
1               5                   10                  15

Val Ile Met Ser Arg Gly
            20

```
<210> SEQ ID NO 11
<211> LENGTH: 102
<212> TYPE: PRT
<213> ORGANISM: Mus musculus

<400> SEQUENCE: 11
```

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Arg Tyr Ile
            20                  25                  30

His Trp Phe Gln Gln Lys Pro Gly Thr Ser Pro Lys Leu Leu Ile Tyr
            35                  40                  45

Ser Thr Ser Asp Leu Ala Ser Gly Val Pro Ala Arg Phe Ser Gly Gly
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Thr Gly Tyr Pro Leu Thr
                85                  90                  95

Phe Gly Ala Gly Thr Lys
            100

<210> SEQ ID NO 12
<211> LENGTH: 10
<212> TYPE: PRT
<213> ORGANISM: Mus musculus

<400> SEQUENCE: 12

Ser Ala Ser Ser Ser Val Arg Tyr Ile His
 1               5                  10

<210> SEQ ID NO 13
<211> LENGTH: 7
<212> TYPE: PRT
<213> ORGANISM: Mus musculus

<400> SEQUENCE: 13

Ser Thr Ser Asp Leu Ala Ser
 1               5

<210> SEQ ID NO 14
<211> LENGTH: 9
<212> TYPE: PRT
<213> ORGANISM: Mus musculus

<400> SEQUENCE: 14

Gln Gln Arg Thr Gly Tyr Pro Leu Thr
 1               5

<210> SEQ ID NO 15
<211> LENGTH: 1404
<212> TYPE: DNA
<213> ORGANISM: Artificial Sequence
<220> FEATURE:
<223> OTHER INFORMATION: Synthetic Primer

<400> SEQUENCE: 15
atgaagtgct cctgggtcat cttcttcctc atggccgtgg tgaccggagt gaactctgag      60
gtgcaactcc agcagtcagg agctgaaatc gtgaagccag cgcaagtgt eaagctgtcc     120 tgcaccgctt ctgggttcaa catcaaggac acctacatgc actgggtgaa gcagcggcca     180
gagcaggggt tggagtggat tgcagaatt gaccctagga acgacaacac caagtttgac     240
cctaagtttc gcgggaaagc aacactgact gccgatacat ccagcaatac tgcctacctg     300
cagctgagca gccttacatc cgaggatgcc gccgtctact actgtgtgcc cgtccccaca     360
aggagctggt atttgatgt gtgggggggcc ggcactagcg tcacagtctc cagcgccaaa     420
acaaagggcc catccgtctt ccccctggcg ccctgctcca ggagcacctc cgagagcaca     480
gccgccctgg gctgcctggt caaggactac ttccccgaac cggtgacggt gtcgtggaac     540
tcaggcgccc tgaccagcgg cgtgcacacc ttccgctg tcctacagtc ctcaggactc     600
tactccctca gcagcgtggt gaccgtgccc tccagcagct gggcacgaa gacctacacc     660

```
tgcaacgtag atcacaagcc cagcaacacc aaggtggaca agagagttga gtccaaatat    720
ggtcccccat gcccaccctg cccagcacct gagttcgaag ggggaccatc agtcttcctg    780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag ctga                                          1404
```

<210> SEQ ID NO 16
<211> LENGTH: 467
<212> TYPE: PRT
<213> ORGANISM: Artificial Sequence
<220> FEATURE:
<223> OTHER INFORMATION: Synthetic Peptide

<400> SEQUENCE: 16

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Ile Val Lys
            20                  25                  30

Pro Gly Ala Ser Val Lys Leu Ser Cys Thr Ala Ser Gly Phe Asn Ile
        35                  40                  45

Lys Asp Thr Tyr Met His Trp Val Lys Gln Arg Pro Glu Gln Gly Leu
    50                  55                  60

Glu Trp Ile Gly Arg Ile Asp Pro Arg Asn Asp Asn Thr Lys Phe Asp
65                  70                  75                  80

Pro Lys Phe Arg Gly Lys Ala Thr Leu Thr Ala Asp Thr Ser Ser Asn
                85                  90                  95

Thr Ala Tyr Leu Gln Leu Ser Ser Leu Thr Ser Glu Asp Ala Ala Val
            100                 105                 110

Tyr Tyr Cys Val Pro Val Pro Thr Arg Ser Trp Tyr Phe Asp Val Trp
        115                 120                 125

Gly Ala Gly Thr Ser Val Thr Val Ser Ser Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220
```

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
            290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
450                 455                 460

Lys Ala Ser
465

<210> SEQ ID NO 17
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 17

Met Lys Cys Ser Trp Val Ile Phe Phe Leu Met Ala Val Val Thr Gly
1               5                   10                  15

Val Asn Ser

<210> SEQ ID NO 18
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 18

Glu Val Gln Leu Gln Gln Ser Gly Ala Glu Ile Val Lys Pro Gly Ala
1               5                   10                  15

Ser Val Lys Leu Ser Cys Thr Ala Ser Gly Phe Asn Ile Lys Asp Thr
                20                  25                  30

```
Tyr Met His Trp Val Lys Gln Arg Pro Glu Gln Gly Leu Glu Trp Ile
             35                  40                  45
Gly Arg Ile Asp Pro Arg Asn Asp Asn Thr Lys Phe Asp Pro Lys Phe
 50                  55                  60
Arg Gly Lys Ala Thr Leu Thr Ala Asp Thr Ser Ser Asn Thr Ala Tyr
 65                  70                  75                  80
Leu Gln Leu Ser Ser Leu Thr Ser Glu Asp Ala Ala Val Tyr Tyr Cys
                 85                  90                  95
Val Pro Val Pro Thr Arg Ser Trp Tyr Phe Asp Val Trp Gly Ala Gly
            100                 105                 110
Thr Ser Val Thr Val Ser Ser Ala Lys
        115                 120
```

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

```
Gly Phe Asn Ile Lys Asp Thr Tyr Met His
 1               5                  10
```

<210> SEQ ID NO 20
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 20

```
Arg Ile Asp Pro Arg Asn Asp Asn Thr Lys Phe Asp Pro Lys Phe Arg
 1               5                  10                  15
Gly
```

<210> SEQ ID NO 21
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 21

```
Val Pro Thr Arg Ser Trp Tyr Phe Asp Val
 1               5                  10
```

<210> SEQ ID NO 22
<211> LENGTH: 717
<212> TYPE: DNA
<213> ORGANISM: Artificial Sequence
<220> FEATURE:
<223> OTHER INFORMATION: Synthetic Primer

<400> SEQUENCE: 22

```
atggagaccc attcccaagt gttcgtctac atgctgctct ggctctccgg agtcgaagga      60
gacatcgtga tgacccagtc tcacaagttc atgtccacca gcgtgggcga tagagtgtct     120
attacctgca aggcctcaca ggacgtgggg aaatccgtcg tgtggtttca gcagaagcct     180
ggccagagtc caaagctttt gatctactgg gcaagcacca ggcacacagg ggtgcccgat     240
cggtttacag gcagcgggag cggcactgat tttactctga caatttccaa cgtccagagc     300
```

```
gaggacctgg ctaattattt ctgtcagcag tacactagct accccctacat gtacacattc    360 gggggggggca caaagctcga gatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct atgcctgcga agtcacccat    660
cagggcctga gctcgcccgt cacaaagagc ttcaacaggg gagagtgtgc tagctga       717
```

<210> SEQ ID NO 23
<211> LENGTH: 238
<212> TYPE: PRT
<213> ORGANISM: Artificial Sequence
<220> FEATURE:
<223> OTHER INFORMATION: Synthetic Peptide

<400> SEQUENCE: 23

```
Met Glu Thr His Ser Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Lys Ser Val Val Trp Phe Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asn Tyr Phe Cys Gln Gln Tyr Thr
            100                 105                 110

Ser Tyr Pro Tyr Met Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Ala Ser
225                 230                 235
```

<210> SEQ ID NO 24
<211> LENGTH: 20
<212> TYPE: PRT
<213> ORGANISM: Artificial Sequence
<220> FEATURE:
<223> OTHER INFORMATION: Synthetic Peptide

```
<400> SEQUENCE: 24

Met Glu Thr His Ser Gln Val Phe Val Tyr Met Leu Leu Trp Leu Ser
1               5                   10                  15

Gly Val Glu Gly
            20

<210> SEQ ID NO 25
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 25

Gly Asp Ile Val Met Thr Gln Ser His Lys Phe Met Ser Thr Ser Val
1               5                   10                  15

Gly Asp Arg Val Ser Ile Thr Cys Lys Ala Ser Gln Asp Val Gly Lys
            20                  25                  30

Ser Val Val Trp Phe Gln Gln Lys Pro Gly Gln Ser Pro Lys Leu Leu
        35                  40                  45

Ile Tyr Trp Ala Ser Thr Arg His Thr Gly Val Pro Asp Arg Phe Thr
50                  55                  60

Gly Ser Gly Ser Gly Thr Asp Phe Thr Leu Thr Ile Ser Asn Val Gln
65                  70                  75                  80

Ser Glu Asp Leu Ala Asn Tyr Phe Cys Gln Gln Tyr Thr Ser Tyr Pro
                85                  90                  95

Tyr Met Tyr Thr Phe Gly Gly Gly Thr Lys
            100                 105

<210> SEQ ID NO 26
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 26

Lys Ala Ser Gln Asp Val Gly Lys Ser Val Val
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 27

Trp Ala Ser Thr Arg His Thr
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 28

Gln Gln Tyr Thr Ser Tyr Pro Tyr Met Tyr Thr
1               5                   10
```

<210> SEQ ID NO 29
<211> LENGTH: 1416
<212> TYPE: DNA
<213> ORGANISM: Artificial Sequence
<220> FEATURE:
<223> OTHER INFORMATION: Synthetic Primer

<400> SEQUENCE: 29

```
atggagagac actggatctt gctcctgctg ttgtccgtga ccgctggagt ccatagccag      60
gtccaactgc aacagtccgg agcagaactt gctaggcctg gagcaagcgt caaaatgtcc     120
tgtaaggctt ccggatacac cctcgcaagc tacaccctgc actgggtgaa gcagcgccct     180
gggcaggggc ttgaatggat tggctatatt aatcccaaca gtggctatac caactacatc     240
cagaagttca aggacaaggc caccctcaca gccgacaaga gctcatcaac tgcttacatg     300
cagctgagtt ctctgacatc tgaggacagt gccgtgtact actgcgctaa aggcggcggg     360
gatcggtatt gtacagattg cgccatggat tattggggcc agggcacatc tgtgactgtg     420
tctcccgcca aaacaaaggg cccatccgtc ttccccctgg cgccctgctc caggagcacc     480
tccgagagca gccgccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacg     660
aagacctaca cctgcaacgt agatcacaag cccagcaaca ccaaggtgga caagagagtt     720
gagtccaaat atggtccccc atgcccaccc tgcccagcac ctgagttcga aggggaccca     780
tcagtcttcc tgttcccccc aaaacccaag gacactctca tgatctcccg gacccctgag     840
gtcacgtgcg tggtggtgga cgtgagccag gaagaccccg aggtccagtt caactggtac     900
gtggatggcg tggaggtgca taatgccaag acaaagccgc gggaggagca gttcaacagc     960
acgtaccgtg tggtcagcgt cctcaccgtc ctgcaccagg actggctgaa cggcaaggag    1020
tacaagtgca aggtctccaa caaaggcctc ccgtcctcca tcgagaaaac catctccaaa    1080
gccaaagggc agccccgaga gccacaggtg tacaccctgc ccccatccca ggaggagatg    1140
accaagaacc aggtcagcct gacctgcctg gtcaaaggct tctaccccag cgacatcgcc    1200
gtggagtggg agagcaatgg gcagccggag aacaactaca agaccacgcc tcccgtgctg    1260
gactccgacg gctccttctt cctctacagc aggctaaccg tggacaagag caggtggcag    1320
gaggggaatg tcttctcatg ctccgtgatg catgaggctc tgcacaacca ctacacacag    1380
aagagcctct ccctgtctct gggtaaagct agctga                              1416
```

<210> SEQ ID NO 30
<211> LENGTH: 471
<212> TYPE: PRT
<213> ORGANISM: Artificial Sequence
<220> FEATURE:
<223> OTHER INFORMATION: Synthetic Peptide

<400> SEQUENCE: 30

```
Met Glu Arg His Trp Ile Leu Leu Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Leu
        35                  40                  45

Ala Ser Tyr Thr Leu His Trp Val Lys Gln Arg Pro Gly Gln Gly Leu
    50                  55                  60
```

-continued

Glu Trp Ile Gly Tyr Ile Asn Pro Asn Ser Gly Tyr Thr Asn Tyr Ile
65                  70                  75                  80

Gln Lys Phe Lys Asp Lys Ala Thr Leu Thr Ala Asp Lys Ser Ser Ser
            85                  90                  95

Thr Ala Tyr Met Gln Leu Ser Ser Leu Thr Ser Glu Asp Ser Ala Val
            100                 105                 110

Tyr Tyr Cys Ala Lys Gly Gly Asp Arg Tyr Cys Thr Asp Cys Ala
            115             120             125

Met Asp Tyr Trp Gly Gln Gly Thr Ser Val Thr Val Ser Pro Ala Lys
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
                245                 250                 255

Glu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
                340                 345                 350

Ser Ile Glu Lys Thr Ile Ser Lys Ala Lys Gly Gln Pro Arg Glu Pro
            355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
                420                 425                 430

Thr Val Asp Lys Ser Arg Trp Gln Glu Gly Asn Val Phe Ser Cys Ser
            435                 440                 445

Val Met His Glu Ala Leu His Asn His Tyr Thr Gln Lys Ser Leu Ser
    450                 455                 460

Leu Ser Leu Gly Lys Ala Ser
465                 470

<210> SEQ ID NO 31
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 31

```
Met Glu Arg His Trp Ile Leu Leu Leu Leu Ser Val Thr Ala Gly
1               5                   10                  15

Val His Ser
```

<210> SEQ ID NO 32
<211> LENGTH: 125
<212> TYPE: PRT
<213> ORGANISM: Artificial Sequence
<220> FEATURE:
<223> OTHER INFORMATION: Synthetic Peptide

<400> SEQUENCE: 32

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Leu Ala Ser Tyr
                20                  25                  30

Thr Leu His Trp Val Lys Gln Arg Pro Gly Gln Gly Leu Glu Trp Ile
            35                  40                  45

Gly Tyr Ile Asn Pro Asn Ser Gly Tyr Thr Asn Tyr Ile Gln Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Gly Gly Gly Asp Arg Tyr Cys Thr Asp Cys Ala Met Asp Tyr
            100                 105                 110

Trp Gly Gln Gly Thr Ser Val Thr Val Ser Pro Ala Lys
        115                 120                 125
```

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 33

```
Gly Tyr Thr Leu Ala Ser Tyr Thr Leu His
1               5                   10
```

<210> SEQ ID NO 34
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 34

```
Tyr Ile Asn Pro Asn Ser Gly Tyr Thr Asn Tyr Ile Gln Lys Phe Lys
1               5                   10                  15

Asp
```

<210> SEQ ID NO 35
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 35

Gly Gly Gly Asp Arg Tyr Cys Thr Asp Cys Ala Met Asp Tyr
1               5                   10

<210> SEQ ID NO 36
<211> LENGTH: 711
<212> TYPE: DNA
<213> ORGANISM: Artificial Sequence
<220> FEATURE:
<223> OTHER INFORMATION: Synthetic Primer

<400> SEQUENCE: 36

```
atgcactccc ttgcacttct gttgagcctc ttgctgctgt gcgtgagtga cagcagagct    60
gagaccaccg tgacacagtc tcctgcctct ctgtcaatga ccatcggaga aaaggtgacc   120
atcaggtgca tgactagcat cgacattgac gatgatatga actggtacca gcagaagcca   180
ggggagcctc caaagctgct gatttccgag ggaaagacac tccgcccggg gtccccagt    240
cggttttcca gctccgggta cggcactgac tttgtcttca ctattgagaa catgctcagc   300
gaggatgtgg ccgattacta ttgtctccaa agcgacaatc tgcccttcac attcggctcc   360
ggcacaaaac tcgagatcaa acgaactgtg ctgcaccat ctgtcttcat cttcccgcca    420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctatgcct gcgaagtcac ccatcagggc   660
ctgagctcgc ccgtcacaaa gagcttcaac aggggagagt gtgctagctg a            711
```

<210> SEQ ID NO 37
<211> LENGTH: 236
<212> TYPE: PRT
<213> ORGANISM: Artificial Sequence
<220> FEATURE:
<223> OTHER INFORMATION: Synthetic Peptide

<400> SEQUENCE: 37

Met His Ser Leu Ala Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Met Thr Ile Gly Glu Lys Val Thr Ile Arg Cys Met Thr Ser Ile Asp
        35                  40                  45

Ile Asp Asp Asp Met Asn Trp Tyr Gln Gln Lys Pro Gly Glu Pro Pro
    50                  55                  60

Lys Leu Leu Ile Ser Glu Gly Lys Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Ala Ser
225                 230                 235

<210> SEQ ID NO 38
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 38

Met His Ser Leu Ala Leu Leu Leu Ser Leu Leu Leu Leu Cys Val Ser
1               5                   10                  15

Asp Ser Arg Ala
            20

<210> SEQ ID NO 39
<211> LENGTH: 103
<212> TYPE: PRT
<213> ORGANISM: Artificial Sequence
<220> FEATURE:
<223> OTHER INFORMATION: Synthetic Peptide

<400> SEQUENCE: 39

Glu Thr Thr Val Thr Gln Ser Pro Ala Ser Leu Ser Met Thr Ile Gly
1               5                   10                  15

Glu Lys Val Thr Ile Arg Cys Met Thr Ser Ile Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Lys Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Phe
                85                  90                  95

Thr Phe Gly Ser Gly Thr Lys
            100

<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide

```
<400> SEQUENCE: 40

Met Thr Ser Ile Asp Ile Asp Asp Met Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 41

Glu Gly Lys Thr Leu Arg Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Leu Gln Ser Asp Asn Leu Pro Phe Thr
1               5
```